United States Patent
Islam

(10) Patent No.: US 10,201,283 B2
(45) Date of Patent: *Feb. 12, 2019

(54) NEAR-INFRARED LASER DIODES USED IN IMAGING APPLICATIONS

(71) Applicant: OMNI MEDSCI, INC., Ann Arbor, MI (US)

(72) Inventor: Mohammed N. Islam, Ann Arbor, MI (US)

(73) Assignee: OMNI MEDSCI, INC., Ann Arbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/029,611

(22) Filed: Jul. 8, 2018

(65) Prior Publication Data

US 2018/0317776 A1  Nov. 8, 2018

Related U.S. Application Data

(63) Continuation of application No. 15/888,052, filed on Feb. 4, 2018, which is a continuation of application
(Continued)

(51) Int. Cl.
*G01J 3/00* (2006.01)
*A61B 5/00* (2006.01)
(Continued)

(52) U.S. Cl.
CPC .......... *A61B 5/0088* (2013.01); *A61B 5/0013* (2013.01); *A61B 5/0022* (2013.01);
(Continued)

(58) Field of Classification Search
CPC ...... G01J 3/02; G01J 3/28; G01J 3/42; G01N 21/31; G01N 21/552
(Continued)

(56) References Cited

U.S. PATENT DOCUMENTS 4,063,106 A  12/1977  Ashkin et al.
4,158,750 A  6/1979  Sakoe et al.
(Continued)

FOREIGN PATENT DOCUMENTS

CN  101849821 B  7/2013
DE  102010012987 A1  10/2010
(Continued)

OTHER PUBLICATIONS

Notice of Allowance for U.S. Appl. No. 14/875,709 dated Jan. 10, 2017.
(Continued)

*Primary Examiner* — Md M Rahman
(74) *Attorney, Agent, or Firm* — Brooks Kushman P.C.

(57) ABSTRACT

A smart phone or tablet includes pulsed laser diodes generating light with near-infrared wavelengths between 700-2500 nanometers. First lenses direct light from the laser diodes to tissue. An array of pulsed laser diodes generates light with near-infrared wavelengths between 700-2500 nanometers. Second lenses form light from the array into spots directed on the tissue. An infrared camera synchronized to the laser diodes and the array generates data based on light reflected from the tissue. The smart phone or tablet generates a two-dimensional or three-dimensional image using the data from the infrared camera. The smart phone or tablet includes a wireless receiver, a wireless transmitter, a display, a voice input module, and a speaker.

20 Claims, 32 Drawing Sheets

Related U.S. Application Data

No. 15/212,549, filed on Jul. 18, 2016, now Pat. No. 9,885,698, which is a continuation of application No. 14/650,897, filed as application No. PCT/US2013/075700 on Dec. 17, 2013, now Pat. No. 9,494,567.

(60) Provisional application No. 61/747,472, filed on Dec. 31, 2012.

(51) Int. Cl.

| | | |
|---|---|---|
| *A61B 5/145* | (2006.01) | |
| *A61B 5/1455* | (2006.01) | |
| *G01J 3/02* | (2006.01) | |
| *G01J 3/10* | (2006.01) | |
| *G01J 3/14* | (2006.01) | |
| *G01J 3/28* | (2006.01) | |
| *G01J 3/42* | (2006.01) | |
| *G01J 3/453* | (2006.01) | |
| *G01N 21/35* | (2014.01) | |
| *G01N 21/3563* | (2014.01) | |
| *G01N 21/359* | (2014.01) | |
| *G01N 21/39* | (2006.01) | |
| *G01N 21/88* | (2006.01) | |
| *G01N 33/02* | (2006.01) | |
| *G01N 33/15* | (2006.01) | |
| *G01N 33/44* | (2006.01) | |
| *G01N 33/49* | (2006.01) | |
| *G01J 3/18* | (2006.01) | |
| *G01J 3/12* | (2006.01) | |
| *G01M 3/38* | (2006.01) | |
| *G01N 21/85* | (2006.01) | |
| *G01N 21/95* | (2006.01) | |
| *H01S 3/00* | (2006.01) | |
| *H01S 3/067* | (2006.01) | |
| *H01S 3/30* | (2006.01) | |

(52) U.S. Cl.
CPC .......... *A61B 5/0075* (2013.01); *A61B 5/0086* (2013.01); *A61B 5/1455* (2013.01); *A61B 5/14532* (2013.01); *A61B 5/14546* (2013.01); *A61B 5/4547* (2013.01); *A61B 5/6801* (2013.01); *A61B 5/7257* (2013.01); *A61B 5/742* (2013.01); *A61B 5/7405* (2013.01); *G01J 3/0218* (2013.01); *G01J 3/108* (2013.01); *G01J 3/14* (2013.01); *G01J 3/28* (2013.01); *G01J 3/2823* (2013.01); *G01J 3/42* (2013.01); *G01J 3/453* (2013.01); *G01N 21/35* (2013.01); *G01N 21/359* (2013.01); *G01N 21/3563* (2013.01); *G01N 21/39* (2013.01); *G01N 21/88* (2013.01); *G01N 33/02* (2013.01); *G01N 33/025* (2013.01); *G01N 33/15* (2013.01); *G01N 33/442* (2013.01); *G01N 33/49* (2013.01); *A61B 2562/0233* (2013.01); *A61B 2562/0238* (2013.01); *A61B 2562/146* (2013.01); *A61B 2576/02* (2013.01); *G01J 3/1838* (2013.01); *G01J 2003/104* (2013.01); *G01J 2003/1208* (2013.01); *G01J 2003/2826* (2013.01); *G01M 3/38* (2013.01); *G01N 21/85* (2013.01); *G01N 21/9508* (2013.01); *G01N 2021/3595* (2013.01); *G01N 2021/399* (2013.01); *G01N 2201/061* (2013.01); *G01N 2201/062* (2013.01); *G01N 2201/06113* (2013.01); *G01N 2201/08* (2013.01); *G01N 2201/12* (2013.01); *G01N 2201/129* (2013.01); *H01S 3/0092* (2013.01); *H01S 3/06758* (2013.01); *H01S 3/302* (2013.01)

(58) Field of Classification Search
USPC ........................................................ 356/300
See application file for complete search history.

(56) References Cited

U.S. PATENT DOCUMENTS

| | | |
|---|---|---|
| 4,221,997 A | 9/1980 | Flemming |
| 4,275,266 A | 6/1981 | Lasar |
| 4,374,618 A | 2/1983 | Howard |
| 4,403,605 A | 9/1983 | Tanikawa |
| 4,462,080 A | 7/1984 | Johnstone et al. |
| 4,516,207 A | 5/1985 | Moriyama et al. |
| 4,523,884 A | 6/1985 | Clement et al. |
| 4,605,080 A | 8/1986 | Lemelson |
| 4,641,292 A | 2/1987 | Tunnell et al. |
| 4,704,696 A | 11/1987 | Reimer et al. |
| 4,728,974 A | 3/1988 | Nio et al. |
| 4,762,455 A | 8/1988 | Coughlan et al. |
| 4,776,016 A | 10/1988 | Hansen |
| 4,958,910 A | 9/1990 | Taylor et al. |
| 4,989,253 A | 1/1991 | Liang et al. |
| 5,078,140 A | 1/1992 | Kwoh |
| 5,084,880 A | 1/1992 | Esterowitz et al. |
| 5,086,401 A | 2/1992 | Glassman et al. |
| 5,134,620 A | 7/1992 | Huber |
| 5,142,930 A | 9/1992 | Allen et al. |
| 5,180,378 A | 1/1993 | Kung et al. |
| 5,191,628 A | 3/1993 | Byron |
| 5,218,655 A | 6/1993 | Mizrahi |
| 5,230,023 A | 7/1993 | Nakano |
| 5,246,004 A | 9/1993 | Clarke et al. |
| 5,267,152 A | 11/1993 | Yang et al. |
| 5,267,256 A | 11/1993 | Saruwatari et al. |
| 5,267,323 A | 11/1993 | Kimura |
| 5,300,097 A | 4/1994 | Lemer et al. |
| 5,303,148 A | 4/1994 | Mattson et al. |
| 5,305,427 A | 4/1994 | Nagata |
| 5,313,306 A | 5/1994 | Kuban et al. |
| 5,323,404 A | 6/1994 | Grubb |
| 5,345,538 A | 9/1994 | Narayannan et al. |
| 5,368,224 A | 11/1994 | Richardson et al. |
| 5,400,165 A | 3/1995 | Gnauck et al. |
| 5,408,409 A | 4/1995 | Glassman et al. |
| 5,458,122 A | 10/1995 | Hethuin |
| 5,544,654 A | 8/1996 | Murphy et al. |
| 5,572,999 A | 11/1996 | Funda et al. |
| 5,617,871 A | 4/1997 | Burrows |
| 5,631,758 A | 5/1997 | Knox et al. |
| 5,687,734 A | 11/1997 | Dempsey et al. |
| 5,695,493 A | 12/1997 | Nakajima et al. |
| 5,696,778 A | 12/1997 | MacPherson |
| 5,704,351 A | 1/1998 | Mortara et al. |
| 5,718,234 A | 2/1998 | Warden et al. |
| 5,746,206 A | 5/1998 | Mannheimer |
| 5,747,806 A | 5/1998 | Khalil |
| 5,748,103 A | 5/1998 | Flach et al. |
| 5,792,204 A | 8/1998 | Snell |
| 5,795,300 A | 8/1998 | Bryars |
| 5,812,978 A | 9/1998 | Nolan |
| 5,855,550 A | 1/1999 | Lai et al. |
| 5,862,803 A | 1/1999 | Besson et al. |
| 5,867,305 A | 2/1999 | Waarts et al. |
| 5,912,749 A | 6/1999 | Harstead et al. |
| 5,919,134 A | 7/1999 | Diab |
| 5,944,659 A | 8/1999 | Flach et al. |
| 5,950,629 A | 9/1999 | Taylor et al. |
| 5,957,854 A | 9/1999 | Besson et al. |
| 5,970,457 A | 10/1999 | Brant et al. |
| 6,014,249 A | 1/2000 | Fermann et al. |
| 6,031,603 A | 2/2000 | Fine et al. |
| 6,043,927 A | 3/2000 | Islam |
| 6,115,673 A | 9/2000 | Malin |
| 6,181,414 B1 | 1/2001 | Raz et al. |
| 6,185,535 B1 | 2/2001 | Hedin et al. |
| 6,200,309 B1 | 3/2001 | Rice et al. |
| 6,212,310 B1 | 4/2001 | Waarts et al. |

(56) References Cited

U.S. PATENT DOCUMENTS

| | | |
|---|---|---|
| 6,224,542 B1 | 5/2001 | Chang et al. |
| 6,246,707 B1 | 6/2001 | Yin et al. |
| 6,246,896 B1 | 6/2001 | Dumoulin |
| 6,273,858 B1 | 8/2001 | Fox et al. |
| 6,278,975 B1 | 8/2001 | Brant et al. |
| 6,281,471 B1 | 8/2001 | Smart |
| 6,285,897 B1 | 9/2001 | Kilcoyne |
| 6,289,238 B1 | 9/2001 | Besson et al. |
| 6,301,271 B1 | 10/2001 | Sanders et al. |
| 6,301,273 B1 | 10/2001 | Sanders et al. |
| 6,325,978 B1 | 12/2001 | Labuda et al. |
| 6,333,803 B1 | 12/2001 | Kurotori et al. |
| 6,337,462 B1 | 1/2002 | Smart |
| 6,340,806 B1 | 1/2002 | Smart et al. |
| 6,350,261 B1 | 2/2002 | Domankevitz et al. |
| 6,364,834 B1 | 4/2002 | Reuss et al. |
| 6,374,006 B1 | 4/2002 | Islam et al. |
| 6,381,391 B1 | 4/2002 | Islam et al. |
| 6,402,691 B1 | 6/2002 | Peddicord et al. |
| 6,407,853 B1 | 6/2002 | Samson et al. |
| 6,436,107 B1 | 8/2002 | Wang et al. |
| 6,441,747 B1 | 8/2002 | Khair et al. |
| 6,442,430 B1 | 8/2002 | Ferek-Petric |
| 6,443,890 B1 | 9/2002 | Schulze et al. |
| 6,450,172 B1 | 9/2002 | Hartlaub et al. |
| 6,453,201 B1 | 9/2002 | Daum et al. |
| 6,454,705 B1 | 9/2002 | Cosentino et al. |
| 6,458,120 B1 | 10/2002 | Shen et al. |
| 6,462,500 B1 | 10/2002 | L'Hegarat et al. |
| 6,463,361 B1 | 10/2002 | Wang et al. |
| 6,480,656 B1 | 11/2002 | Islam et al. |
| 6,512,936 B1 | 1/2003 | Monfre |
| 6,534,012 B1 | 4/2003 | Viswanathan |
| 6,549,702 B2 | 4/2003 | Islam et al. |
| 6,567,431 B2 | 5/2003 | Tabirian et al. |
| 6,587,702 B1 | 7/2003 | Ruchti |
| 6,603,910 B2 | 8/2003 | Islam et al. |
| 6,605,080 B1 | 8/2003 | Altshuler et al. |
| 6,611,643 B2 | 8/2003 | Birk |
| 6,619,835 B2 | 9/2003 | Kita |
| 6,625,180 B2 | 9/2003 | Bufetov et al. |
| 6,631,025 B2 | 10/2003 | Islam et al. |
| 6,640,117 B2 | 10/2003 | Makarewicz |
| 6,659,947 B1 | 12/2003 | Carter et al. |
| 6,659,999 B1 | 12/2003 | Anderson et al. |
| 6,701,170 B2 | 3/2004 | Stetson |
| 6,708,048 B1 | 3/2004 | Chance |
| 6,731,967 B1 | 5/2004 | Turcott |
| 6,738,652 B2 | 5/2004 | Mattu |
| 6,760,148 B2 | 7/2004 | Islam |
| 6,773,922 B2 | 8/2004 | Jeng |
| 6,788,965 B2 | 9/2004 | Ruchti |
| 6,802,811 B1 | 10/2004 | Slepian |
| 6,816,241 B2 | 11/2004 | Grubisic |
| 6,847,336 B1 | 1/2005 | Lemelson |
| 6,864,978 B1 | 3/2005 | Hazen |
| 6,885,498 B2 | 4/2005 | Islam |
| 6,885,683 B1 | 4/2005 | Fermann et al. |
| 6,916,096 B2 | 7/2005 | Eberl et al. |
| 6,943,936 B2 | 9/2005 | Islam et al. |
| 6,990,364 B2 | 1/2006 | Ruchti |
| 7,010,336 B2 | 3/2006 | Lorenz |
| 7,027,467 B2 | 4/2006 | Baev et al. |
| 7,060,061 B2 | 6/2006 | Altshuler et al. |
| 7,105,823 B2 | 9/2006 | Abrahamsson et al. |
| 7,133,710 B2 | 11/2006 | Acosta |
| 7,167,300 B2 | 1/2007 | Fermann et al. |
| 7,184,148 B2 | 2/2007 | Alphonse |
| 7,209,657 B1 | 4/2007 | Islam |
| 7,233,816 B2 | 6/2007 | Blank |
| 7,259,906 B1 | 8/2007 | Islam |
| 7,263,288 B1 | 8/2007 | Islam |
| 7,294,105 B1 | 11/2007 | Islam |
| 7,299,080 B2 | 11/2007 | Acosta |
| 7,317,938 B2 | 1/2008 | Lorenz |
| 7,332,784 B2 | 2/2008 | Mills et al. |
| 7,356,364 B1 | 4/2008 | Bullock et al. |
| 7,395,158 B2 | 7/2008 | Monfre |
| 7,433,116 B1 | 10/2008 | Islam |
| 7,468,036 B1 | 12/2008 | Rulkov et al. |
| 7,519,253 B2 | 4/2009 | Islam |
| 7,519,406 B2 | 4/2009 | Blank |
| 7,620,674 B2 | 11/2009 | Ruchti |
| 7,648,463 B1 | 1/2010 | Elhag et al. |
| 7,697,966 B2 | 4/2010 | Monfre |
| 7,771,320 B2 | 8/2010 | Riley et al. |
| 7,787,503 B2 | 8/2010 | Wadsworth |
| 7,787,924 B2 | 8/2010 | Acosta |
| 7,800,818 B2 | 9/2010 | Mattsson |
| 7,807,718 B2 | 10/2010 | Hashim |
| 7,848,605 B2 | 12/2010 | Ridder et al. |
| 7,890,158 B2 | 2/2011 | Rowe et al. |
| 8,000,574 B2 | 8/2011 | Buchter |
| 8,145,286 B2 | 3/2012 | Arai |
| 8,157,730 B2 | 4/2012 | LeBoeuf et al. |
| 8,158,493 B2 | 4/2012 | Shah et al. |
| 8,172,761 B1 | 5/2012 | Rulkov et al. |
| 8,180,422 B2 | 5/2012 | Rebec |
| 8,180,591 B2 | 5/2012 | Yuen et al. |
| 8,213,007 B2 | 7/2012 | Wang et al. |
| 8,310,336 B2 | 11/2012 | Muhsin et al. |
| 8,315,682 B2 | 11/2012 | Such et al. |
| 8,430,310 B1 | 4/2013 | Ho et al. |
| 8,463,576 B2 | 6/2013 | Yuen et al. |
| 8,472,108 B2 | 6/2013 | Islam |
| 8,475,367 B1 | 7/2013 | Yuen et al. |
| 8,509,882 B2 | 8/2013 | Albert et al. |
| RE44,875 E | 4/2014 | Kiani et al. |
| 8,755,871 B2 | 6/2014 | Weng et al. |
| 8,788,002 B2 | 7/2014 | LeBoeuf et al. |
| 8,945,017 B2 | 2/2015 | Venkatraman et al. |
| 8,948,832 B2 | 2/2015 | Hong et al. |
| 8,954,135 B2 | 2/2015 | Yuen et al. |
| 9,142,117 B2 | 9/2015 | Muhsin et al. |
| 9,164,032 B2 | 10/2015 | Islam |
| 9,179,876 B2 | 11/2015 | Ochs et al. |
| 9,192,329 B2 | 11/2015 | Al-Ali |
| 9,241,676 B2 | 1/2016 | Lisogurski et al. |
| 9,326,712 B1 | 5/2016 | Kiani |
| 9,596,990 B2 | 3/2017 | Park et al. |
| 9,651,533 B2 | 5/2017 | Islam |
| 9,675,250 B2 | 6/2017 | Tverskoy |
| 9,757,040 B2 | 9/2017 | Islam |
| 9,820,658 B2 | 11/2017 | Tran |
| 9,861,286 B1 | 1/2018 | Islam |
| 9,885,698 B2 | 2/2018 | Islam |
| 2002/0013518 A1 | 1/2002 | West et al. |
| 2002/0019584 A1 | 2/2002 | Schulze et al. |
| 2002/0032468 A1 | 3/2002 | Hill et al. |
| 2002/0082612 A1 | 6/2002 | Moll et al. |
| 2002/0109621 A1 | 8/2002 | Khair et al. |
| 2002/0115914 A1 | 8/2002 | Russ |
| 2002/0128846 A1 | 9/2002 | Miller |
| 2002/0178003 A1 | 11/2002 | Gehrke et al. |
| 2003/0022126 A1 | 1/2003 | Buchalla |
| 2004/0174914 A1 | 9/2004 | Fukatsu |
| 2004/0240037 A1 | 12/2004 | Harter |
| 2005/0049468 A1 | 3/2005 | Carlson et al. |
| 2005/0111500 A1 | 5/2005 | Harter et al. |
| 2005/0133691 A1 | 6/2005 | Doppke et al. |
| 2005/0209516 A1 | 9/2005 | Fraden |
| 2006/0058683 A1 | 3/2006 | Chance |
| 2006/0198397 A1 | 9/2006 | Korolev et al. |
| 2006/0223032 A1 | 10/2006 | Fried |
| 2006/0245461 A1 | 11/2006 | Islam |
| 2006/0268393 A1 | 11/2006 | Islam |
| 2006/0281982 A1 | 12/2006 | Grata et al. |
| 2006/0283931 A1 | 12/2006 | Polli et al. |
| 2007/0021670 A1 | 1/2007 | Mandelis et al. |
| 2007/0078348 A1 | 4/2007 | Holman |
| 2008/0086318 A1 | 4/2008 | Gilley et al. |
| 2008/0105665 A1 | 5/2008 | Kondo |
| 2009/0028193 A1 | 1/2009 | Islam |
| 2009/0105605 A1 | 4/2009 | Abreu |

(56) References Cited

U.S. PATENT DOCUMENTS

| | | |
|---|---|---|
| 2009/0204110 A1 | 8/2009 | Islam |
| 2009/0244288 A1 | 10/2009 | Fujimoto et al. |
| 2009/0287067 A1 | 11/2009 | Dorogusker et al. |
| 2010/0046067 A1 | 2/2010 | Fermann et al. |
| 2010/0160794 A1 | 6/2010 | Banet et al. |
| 2010/0160798 A1 | 6/2010 | Banet et al. |
| 2010/0217102 A1 | 8/2010 | LeBoeuf et al. |
| 2010/0322490 A1 | 12/2010 | Pan |
| 2010/0331637 A1 | 12/2010 | Ting |
| 2011/0040197 A1 | 2/2011 | Welch et al. |
| 2011/0143364 A1 | 6/2011 | Kim |
| 2011/0208015 A1 | 8/2011 | Welch et al. |
| 2011/0237911 A1 | 9/2011 | Lamego et al. |
| 2011/0267688 A1 | 11/2011 | Kleppe et al. |
| 2011/0282167 A1 | 11/2011 | Ridder et al. |
| 2011/0292376 A1 | 12/2011 | Kukushkin et al. |
| 2012/0013722 A1 | 1/2012 | Wong |
| 2012/0203077 A1 | 8/2012 | He et al. |
| 2012/0239013 A1 | 9/2012 | Islam |
| 2012/0245439 A1 | 9/2012 | Andre et al. |
| 2012/0310062 A1 | 12/2012 | Li et al. |
| 2012/0316455 A1 | 12/2012 | Rahman et al. |
| 2013/0274569 A1 | 10/2013 | Islam |
| 2013/0281795 A1 | 10/2013 | Varadan |
| 2013/0303921 A1 | 11/2013 | Chu et al. |
| 2013/0327966 A1 | 12/2013 | Fidler et al. |
| 2014/0078510 A1 | 3/2014 | Rubio Guivernau et al. |
| 2014/0081100 A1 | 3/2014 | Muhsin et al. |
| 2014/0236021 A1 | 8/2014 | Islam |
| 2014/0249427 A1 | 9/2014 | Liu |
| 2014/0275852 A1 | 9/2014 | Hong et al. |
| 2014/0275854 A1 | 9/2014 | Venkatraman et al. |
| 2015/0011851 A1 | 1/2015 | Mehta et al. |
| 2016/0045118 A1 | 2/2016 | Kiani |
| 2016/0327476 A1 | 11/2016 | Islam |

FOREIGN PATENT DOCUMENTS

| | | |
|---|---|---|
| EP | 1148666 | 10/2001 |
| JP | 2005270544 A | 10/2005 |
| WO | WO09715240 | 5/1997 |
| WO | WO97049340 | 12/1997 |
| WO | WO01150959 | 7/2001 |
| WO | 200189362 | 11/2001 |
| WO | 200227640 | 4/2002 |
| WO | 200228123 | 4/2002 |
| WO | 2005013843 A2 | 2/2005 |
| WO | 2007061772 A2 | 5/2007 |
| WO | 2009130464 A1 | 10/2009 |
| WO | 2012135952 A1 | 10/2012 |
| WO | 2013012938 | 1/2013 |
| WO | 2015084376 | 6/2015 |

OTHER PUBLICATIONS

Ooi ET, Zhang XQ, Chen JH, Soh PH, Ng K, Yeo JH, "Non-invasive glucose measurement using multiple laser diodes," Optical Diagnostic and Sensing VII, edited by Gerard L. Cote, Alexander V. Priezzhev, Proc. of SPIE vol. 6445, 64450K , (2007).

Schulz, I., J. Putzger, A. Niklas, M. Brandt, A. Jager, A. Hardt, S. Knorzer, K.A. Hiller, S. Loffler, G. Schmalz, S.N. Danilov, S. Giglberger, M. Hirmer, S.D. Ganichev, G. Monkman, "PPG signal acquisition and analysis on in vitro tooth model for dental pulp vitality assessment," ARC Submission 16, (2012).

Drexler, C., Hirmer, M., Danilov, S., Giglberger, S., Putzger, J., Niklas, A., Jager, A., Hiller, K., Loffler, S., Schmalz, G., Redlich, B., Schulz, I., Monkman, G., Ganichev, S. "Infrared spectroscopy for clinical diagnosis of dental pulp vitality." Infrared, Millimeter, and Terahertz Waves (IRMMW-THz), 2012 37th International Conference on. IEEE (2012).

Hirmer, Marion, Danilov, Sergey, Giglberger, Stephan, Putzger, Jurgen, Niklas, Andreas, Jager, Andreas, Hiller, Karl-Anton, Loffler, Susanne, Schmalz, Gottfried, Redlich, Britta, Schulz, Irene, Monkman, Gareth, Ganichev, Sergey. "Spectroscopic Study of Human Teeth and Blood from Visible to Terahertz Frequencies for Clinical Diagnosis of Dental Pulp Vitality." Journal of Infrared, Millimeter, and Terahertz Waves 33.3 (2012): 366-375.

Na, J, J.H. Baek, S.Y. Ryu, C. Lee, B.H. Lee, "Tomographic imaging of incipient dental-caries using optical coherence tomography and comparison with various modalities," Optical Review, vol. 16, No. 4, pp. 426-431 (2009).

Vinay V. Alexander et al.; Modulation Instability High Power All-Fiber Supercontinuum Lasers and Their Applications; Optical Fiber Technology 18; 2012; pp. 349-374.

Robert S. Jones et al.; Near-Infrared Transillumination at 1310-nm for the Imaging of Early Dental Decay; vol. 11; No. 18; Optics Express 2259; Sep. 8, 2003.

Extended European Search Report for European Application No. 13867874.3 dated Jul. 15, 2016.

Extended European Search Report for European Application No. 13867892.5 dated Jul. 22, 2016.

U.S. Appl. No. 61/350,673; titled: Opticoustic Sensor; Inventor: Massi Joe E. Kiani; filed Jun. 2, 2010.

Non-Final Office Action for U.S. Appl. No. 14/875,709 dated May 26, 2016.

Final Office Action dated Oct. 21, 2016 for U.S. Appl. No. 14/875,709.

Extended European Search Report for European Application No. 17156625.0 dated Mar. 20, 2017.

Islam, M. N., et al., "Broad bandwidths from frequency-shifting solitons in fibers", Optics Letters, vol. 14, No. 7, Apr. 1, 1989, pp. 370-372.

Islam, M. N., et al., "Femtosecond distributed soliton spectrum in fibers", J. Opt. Soc. Am. B, vol. 6, No. 6, Jun. 1989, pp. 1149-1158.

Busse, Lynda E., et al., "Design Parameters for Fluoride Multimode Fibers", Journal of Lightwave Technology, vol. 9, No. 7, Jul. 1991, pp. 828-831.

Wuthrich, Stefan, et al., "Optical damage thresholds at 2.94 um in fluoride glass fibers", Applied Optics, vol. 31, No. 27, Sep. 20, 1992, pp. 5833-5837.

Inoue, H., et al., "Computer simulation of the vibrational spectra and properties of fluoride glasses based on ZrF4", Journal of Non-Crystalline Solids, vol. 161, 1993, pp. 118-122.

Mizunami, Toru, et al., "Gain saturation characteristics of Raman amplification in silica and fluoride glass optical fibers", Optics Communications 97, 1993, pp. 74-78.

Desthieux, B., et al., "111 κW (0. 5 mJ) pulse amplification at 1.5 um using a gated cascade of three erbium-doped fiber amplifiers," Appl. Phys. Lett. vol. 63, Aug. 2, 1993, pp. 586-588.

Edwards, Glenn, et al., Tissue ablation by a free-electron laser tuned to the amide II band, Nature, vol. 371, Sep. 29, 1994, pp. 416-419.

Borrelli, N. F., et al., "Resonant and non-resonant effects in photonic glasses", Journal of Non-Crystalline Solids 185, 1995, pp. 109-122.

Asobe, Masaki, et al., "Third-order nonlinear spectroscopy in As2S3 chalcogenide glass fibers", J. Appl. Phys. 77 (11), Jun. 1, 1995, pp. 5518-5523.

Jarman, Richard H., "Novel optical fiber lasers", Current Opinion in Solid State and Materials Science, 1996, pp. 199-203.

Iatridis, James C., et al., "Is the Nucleus Pulposus a Solid or a Fluid? Mechanical Behaviors of the Nucleus Pulposus of the Human Intervertebral Disc", Spine, vol. 21(10), May 15, 1996, pp. 1174-1184.

Asobe, Masaki, "Nonlinear Optical Properties of Chalcogenide Glass Fibers and Their Application to All-Optical Switching", Optical Fiber Technology, vol. 3, Article No. OF970214, 1997, pp. 142-148.

Smektala, F., et al., "Chalcogenide glasses with large non-linear refractive indices", Journal of Non-Crystalline Solids 239, 1998, pp. 139-142.

Hamilton, James D., et al., "High Frequency Ultrasound Imaging with Optical Arrays", IEEE Transactions on Ultrasonics, Ferroelectrics, and Frequency Control, vol. 45, No. 1, Jan. 1998, pp. 216-235.

(56) References Cited

OTHER PUBLICATIONS

Hamilton, James D., et al., "High Frequency Ultrasound Imaging Using an Active Optical Detector", IEEE Transactions on Ultrasonics, Ferroelectrics, and Frequency Control, vol. 45, No. 3, May 1998, pp. 719-727.
Nowak, G. A., et al., "Low-power high-efficiency wavelength conversion based on modulational instability in high-nonlinearity fiber," Optics Letters, vol. 23, No. 12, Jun. 15, 1998, pp. 936-938.
Cardinal, T., et al., "Non-linear optical properties of chalcogenide glasses in the system As-S-Se", Journal of Non-Crystalline Solids 256 & 257, 1999, pp. 353-360.
Lucas, Jacques, "Infrared glasses", Current Opinion in Solid State & Materials Science 4, 1999. pp. 181-187.
Sanghera, J. S., et al., Active and passive chalcogenide glass optical fibers for IR applications: a review, Journal of Non-Crystalline Solids 256 & 257, 1999, pp. 6-16.
Nishida, Yoshiki, et al., "Reliability of Fluoride Fiber Module for Optical Amplifier Use", IEEE Photonics Technology Letters, vol. 11, No. 12, Dec. 1999, pp. 1596-1598.
Nowak, George A., et al., "Stable supercontinuum generation in short lengths of conventional dispersion-shifted fiber", Applied Optics, vol. 38, No. 36, Dec. 20, 1999, pp. 7364-7369.
Urban, J. P. G., et al., "The Nucleus of the Intervertebral Disc from Development to Degeneration" Amer. Zool., vol. 40, 2000, pp. 53-61.
Hamilton, James D., et al., "High Frequency Optoacoustic Arrays Using Etalon Detection", IEEE Transactions on Ultrasonics, Ferroelectrics, and Frequency Control, vol. 47, No. 1, Jan. 2000, pp. 160-169.
Ranka, Jinendra K., et al., "Visible continuum generation in airsilica microstructure optical fibers with anomalous dispersion at 800 nm", Optics Letters, vol. 25, No. 1, Jan. 1, 2000, pp. 25-27.
Boult, Maggi, et al., "Systematic Review of Percutaneous Endoscopic Laser Discectomy: Update and Re-appraisal", Australian Safety and Efficacy Register of New Interventional Procedures—Surgical Report No. 5, Feb. 2000, 49 pages.
Boult, Maggi, et aL, "Percutaneous Endoscopic Laser Discectomy", Systematic Review, Aust. N.Z.J. Surg., vol. 70, Apr. 7, 2000, pp. 475-479.
Camacho, Nancy P., et al., "FTIR Microscopic Imaging of Collagen and Proteoglycan in Bovine Cartilage," Biopolymers (Biospectroscopy), vol. 62, 2001, pp. 1-8.
Choi, Joon Y., et al, "Thermal, Mechanical, Optical, and Morphologic Changes in Bovine Nucleus Pulposus Induced by Nd:YAG ($\lambda$=1.32 um) Laser Irradiation", Lasers in Surgery and Medicine, vol. 28, 2001, pp. 248-254.
Hafez, M. I., et al., "The Effect of Irrigation on Peak Temperatures in Nerve Root, Dura, and Intervertebral Disc During Laser-Assisted Foraminoplasty", Lasers in Surgery and Medicine, vol. 29, 2001, pp. 33-37.
Jackson, Stuart D., et al., "Theory and numerical simulation of nth-order cascaded Raman fiber lasers", J. Opt. Soc. Am. B, vol. 18, No. 9, Sep. 2001, pp. 1297-1306.
Werle, Peter, et al., "Near- and mid-infrared laser-optical sensors for gas analysis", Optics and Lasers in Engineering 37, 2002, pp. 101-114.
Beck, Mattias, et al., "Continuous Wave Operation of a Mid-Infrared Semiconductor Laser at Room Temperature," Science vol. 295, www.sciencemag.org, Jan. 11, 2002, pp. 301-305.
Harbold, J. M., et al., "Highly nonlinear As—S—Se glasses for all-optical switching", Optics Letters, vol. 27, No. 2, Jan. 15, 2002, pp. 119-121.
Coen, Stephane, et al., "Supercontinuum generation by stimulated Raman scattering and parametric four-wave mixing in photonic crystal fibers", J. Opt. Soc. Am. B, vol. 19, No. 4, Apr. 2002, pp. 753-764.
Dudley, John M., et al., "Supercontinuum generation in air-silica microstructured fibers with nanosecond and femtosecond pulse pumping", J. Opt. Soc. Am. B, vol. 19, No. 4, Apr. 2002, pp. 765-771.

Harbold, Jeffrey M., et al., "Highly Nonlinear Ge—As—Se and Ge—As—S—Se Glasses for All-Optical Switching", IEEE Photonics Technology Letters, vol. 14, No. 6, Jun. 2002, pp. 822-824.
Husakou, Anton V., et al, "Supercontinuum generation, four-wave mixing, and fission of higher-order solitons in photonic-crystal fibers", J. Opt. Soc. Am. B, vol. 19, No. 9, Sep. 2002, pp. 2171-2182.
Wadsworth, William J., et al., "Supercontinuum generation in photonic crystal fibers and optical fiber tapers: a novel light source", J. Opt. Soc. Am. B, vol. 19, No. 9, Sep. 2002, pp. 2148-2155.
Kumar, V.V. Ravi Kanth, et al, "Extruded soft glass photonic crystal fiber for ultrabroad supercontinuum generation", Optics Express, vol. 10, No. 25, Dec. 16, 2002, pp. 1520-1525.
Edwards, Glenn S., et al., "Advantage of the Mark-III FEL for biophysical research and biomedical applications", J. Synchrotron Rad. vol. 10, 2003, pp. 354-357.
Nicholson, J. W., et al., "Pulsed and continuous-wave supercontinuum generation in highly nonlinear, dispersion-shifted fibers", Applied Physics B 77, 2003, pp. 211-218.
Sobol, Emil, et al., "Time-resolved, light scattering measurements of cartilage and cornea denaturation due to free electron laser radiation", Journal of Biomedical Optics, vol. 8, No. 2, Apr. 2003, pp. 216-222.
Nicholson, J. W., et al., "All-fiber, octave-spanning supercontinuum", Optics Letters, vol. 28, No. 8, Apr. 15, 2003, pp. 643-645.
Faralli, S., et al., "Impact of Double Rayleigh Scattering Noise in Distributed Higher Order Raman Pumping Schemes", IEEE Photonics Technology Letters, vol. 15, No. 6, Jun. 2003, pp. 804-806.
"New and Emerging Techniques—Surgical, Rapid Review, Laser Discectomy", Australian Safety and Efficacy Register of New Interventional Procedures—Surgical, Jun. 2003, 12 pages.
Avdokhin, A. V., et al, "Continuous-wave, high-power, Raman continuum generation in holey fibers", Optics Letters, vol. 28, No. 15, Aug. 1, 2003, pp. 1353-1355.
Mussot, Arnaud, et al., "Generation of a broadband single-mode supercontinuum in a conventional dispersion-shifted fiber by use of a subnanosecond microchip laser", Optics Letters, vol. 28, No. 19, Oct. 1, 2003, pp. 1820-1822.
Slusher, Richard, et al., "Highly nonlinear composite chalcogenide/polymer fibers", OSA 2004, 1 page.
Thongtrangan, Issada, et al., "Minimally invasive spinal surgery: a historical perspective", Neurosurg. Focus, vol. 16, Article 13, Jan. 2004, pp. 1-10.
Extended European Search Report for European Application No. 17155541.0 dated May 24, 2017.
Hori, Takashi, et al., "Flatly broadened, wideband and low noise supercontinuum generation in highly nonlinear hybrid fiber", Optics Express, vol. 12, No. 2, Jan. 26, 2004, pp. 317-324.
Wadsworth, W. J., et al., "Supercontinuum and four-wave mixing with Q-switched pulses in endlessly single-mode photonic crystal fibres", Optics Express, vol. 12, No. 2, Jan. 26, 2004, pp. 299-309.
Hilligsoe, Karen Marie, et al., "Supercontinuum generation in a photonic crystal fiber with two zero dispersion wavelengths", Optics Express, vol. 12, No. 6, Mar. 22, 2004, pp. 1045-1054.
Venugopalan, V., "Optical Society of America BIOMED Topical Meeting Tutorial on Tissue Optics", Apr. 27, 2004, pp. 1-32.
Slusher, Richart E., et al., "Large Raman gain and nonlinear phase shifts in high-purity As2So3 chalcogenide fibers", J. Opt. Soc. Am. B, vol. 21, No. 6, Jun. 2004, pp. 1146-1155.
Leon-Saval, S. G., et al., "Supercontinuum generation in submicron fibre waveguides", Optics Express, vol. 12, No. 13, Jun. 28, 2004, pp. 2864-2869.
Nicholson, J. W., et al., "High power, single mode, all-fiber source of femtosecond pulses at 1550 nm and its use in supercontinuum generation", Optics Express, vol. 12, No. 13, Jun. 28, 2004, pp. 3025-3034.
Genty, G., et al., "Enhanced bandwidth of supercontinuum generated m microstructured fibers", Optics Express, vol. 12, No. 15, Jul. 26, 2004, pp. 3471-3480.
Champert, Pierre-Alain, et al., "White-light supercontinuum generation in normally dispersive optical fiber using original multiwavelength pumping system", Optics Express, vol. 12, No. 19, Sep. 20, 2004, pp. 4366-4371.

(56) References Cited

OTHER PUBLICATIONS

Nicholson, J. W., "Supercontinuum generation in ultraviolet-irradiated fibers", Optics Letters, vol. 29, No. 20, Oct. 15, 2004, pp. 2363-2365.
Hori, Takashi, et al., "Experimental and numerical analysis of widely broadened supercontinuum generation in highly nonlinear dispersion-shifted fiber with a femtosecond pulse", J. Opt. Soc. Am. B, vol. 21, No. 11, Nov. 2004, pp. 1969-1980.
Demircan, Ayhan, et al., "Supercontinuum generation by the modulation instability", Optics Communications 244, 2005, pp. 181-185.
Papernyi, S. B., et al., "Sixth-Order Cascaded Raman Amplification", OFC/NFOEC, 2005, 3 pages.
Tanaka, Keiji, "Optical nonlinearity in photonic glasses", Journal of Materials Science: Materials in Electronics 16, 2005, pp. 633-643.
Westbrook, Paul S., "Improved Supercontinuum Generation Through UV Processing of Highly Nonlinear Fibers", Journal of Lightwave Technology, vol. 23, No. 1, Jan. 2005, pp. 13-18.
Abeeluck, Akheelesh K., et al., "Continuous-wave pumping in the anomalous- and normal dispersion regimes of nonlinear fibers for supercontinuum generaffon", Optics Letters, vol. 30, No. 1, Jan. 1, 2005, pp. 61-63.
Kutz, J. Nathan, et al., Enhanced Supercontinuum Generation through Dispersion-Management, Optics Express, vol. 13, No. 11, May 30, 2005, pp. 3989-3998.
Lee, Ju Han, et al., "Experimental performance comparison for various continuous-wave supercontinuum schemes: ring cavity and single pass structures", Optics Express, vol. 13, No. 13, Jun. 27, 2005, pp. 4848-4853.
Saliminia, A., et al., "Ultra-broad and coherent white light generation in silica glass by focused femtosecond pulses at 1.5pm", Optics Express, vol. 13, No. 15, Jul. 25, 2005, pp. 5731-5738.
Takushima, Yuichi, High average power, depolarized supercontinuum generation using a 1.55-um ASE noise source, Optics Express, vol. 13, No. 15, Jul. 25, 2005, pp. 5871.-5877.
Travers, J. C., et al., "Extended continuous-wave supercontinuum generation in a low-water-loss holey fiber", Optics Letters, vol. 30, No. 15, Aug. 1, 2005, pp. 1938-1940.
Kobtsev, Serguei M., et al., "Modelling of high-power supercontinuum generation in highly nonlinear, dispersion shifted fibers at CW pump", Optics Express, vol. 13, No. 18, Sep. 5, 2005, pp. 6912-6918.
Falk, Peter, et al., "Supercontinuum generation in a photonic crystal fiber with two zero-dispersion wavelengths tapered to normal dispersion at all wavelengths", Optics Express, vol. 13, No. 19, Sep. 19, 2005, pp. 7535-7540.
Tombelaine, Vincent, et al., "Ultra wide band supercontinuum generation in air-silica holey fibers by SHG-induced modulation instabilities", Optics Express, vol. 13, No. 19, Sep. 19, 2005, pp. 7399-7404.
Hazen, K.H., M.A. Arnold, G.W. Small, "Measurement of glucose and other analytes in undiluted human serum with near-infrared transmission spectroscopy," Analytica Chimica Acta, vol. 371, pp. 255-267 (1998).
Malin, S.F., T.L. Ruchti, T.B. Blank, S.N. Thennadil, S.L. Monfre, "Noninvasive prediction of glucose by near-infrared diffuse reflectance spectroscopy," Clinical Chemistry, vol. 45, No. 9, pp. 1651-1658 (1999).
Thennadil, S.N., J.L. Rennert, B.J. Wenzel, K.H. Hazen, T.L. Ruchti, M.B. Block, "Comparison of glucose concentration in interstitial fluid, and capillary and venous blood during rapid changes in blood glucose levels," Diabetes Technology & Therapeutics, vol. 3, No. 3, pp. 357-365 (2001).
Troy, T.L., S.N. Thennadil, "Optical properties of human skin in the near infrared wavelength range of 1000 to 2200nm," Journal of Biomedical Optics, vol. 6, No. 2, pp. 167-176, (2001).
Blank, T.B., T.L. Ruchti, A.D. Lorenz, S.L. Monfre, M.R. Makarewicz, M. Mattu, K.H. Hazen, "Clinical results from a non-invasive blood glucose monitor," Optical Diagnostics and Sensing of Biological Fluids and Glucose and Cholesterol Monitoring II, A.V. Priezzhev and G.L. Cote, Editors, Proceedings of SPIE, vol. 4624, pp. 1019 (2002).
Yeh, S-J, C.F. Hanna, O.S. Khalil, "Monitoring blood glucose changes in cutaneous tissue by temperature-modulated localized reflectance measurements," Clinical Chemistry, vol. 49, No. 6, pp. 924-934 (2003).
Marbach, R., T. Koschinsky, F.A. Gries, H.M. Heise, "Noninvasive blood glucose assay by near-infrared diffuse reflectance spectroscopy of the human inner lip," Applied Spectroscopy, vol. 47, No. 7, pp. 875-881 (1993).
Enejder, A.M.K., T.G. Scecina, J. Oh, M. Hunter, W.C. Shih, S. Sasic, G.L. Horowitz, M.S. Feld, "Raman spectroscopy for noninvasive glucose measurements," Journal of Biomedical Optics, vol. 10, No. 3, 031114 (2005).
Olesberg, J.T., L. Liu, V.V. Zee, M.A. Arnold, "In vivo near-infrared spectroscopy of rat skin tissue with varying blood glucose levels," Analytic Chemistry, vol. 78, No. 1, pp. 215-223 (2006).
Olesberg, J.T., M.A. Arnold, C. Mermelstein, J. Schmitz, J. Wagner, "Tunable laser diode system for noninvasive blood glucose measurements," Applied Spectroscopy, vol. 59, No. 12, pp. 1480-1484 (2005).
Harman-Boehm, I. A. Gal, A.M. Raykhman, J.D. Zahn, E. Naidis, Y. Mayzel, "Noninvasive glucose monitoring: a novel approach," Journal of Diabetes Science and Technology, vol. 3, No. 2 pp. 253-260 (2009).
Kim-K.D., G.S. Son, S.S. Lim, S.S. Lee, "Measurement of glucose level exploiting a relative optical absorption at discrete probe wavelengths," Japanese Journal of Applied Physics, vol. 48, 077001 (2009).
Smith, J.L., "The Pursuit of Noninvasive Glucose: Hunting the Deceitful Turkey," 2nd Edition, pp. 1-141 (2011).
Pezzaniti, J.L., T.W. Jeng, L. McDowell, G.M. Oosta, "Preliminary investigation of near-infrared spectroscopic measurements of urea, creatinine, glucose, protein and ketone in urine," Clinical Biochemistry, vol. 34, pp. 239-246 (2001).
Lussi, A., R. Hibst, R. Paulus, "Diagnodent: An optical method for caries detection," Journal of Dental Research, vol. 83, special issue C, pp. C80-C83 (2004).
Reese, E.L, E.E. Fisher, D.A. Horowitz, "Photoelectric densitometry of the circulation of the human dental pulp," The Journal of the Baltimore College of Dental Surgery, vol. 26, No. 1, pp. 6-18 (1971).
Zakian, C. I. Pretty, R. Ellwood, "Near-infrared hyperspectral imaging of teeth for dental canes detection," Journal of Biomedical Optics, vol. 16, No. 6, 064047 (2009).
Belikov, A.V., A.V. Skripnik, K.V. Shatilova, "Study of the dynamics of the absorption spectra of human tooth enamel and dentine under heating and ablation by submillisecond pulse radiation of an erbium laser with a generation wavelength of 2.79 um," Optics and Spectroscopy, vol. 109, No. 2, pp. 211-216 (2010).
Karlsson, L. "Caries detection methods based on changes in optical properties between healthy and carious tissue," International Journal of Dentistry, vol. 2010, Article ID 270729, 9 pages (2010).
Fried, D. M. Staninec, C.L. Darling, "Near-infrared imaging of dental decay at 1310nm," Journal of Laser Dentistry, vol. 18, No. 1, pp. 8-16 (2010).
Burmen, M. P. Usenik, A. Fidler, F. Pernus, B. Likar, "A construction of standardized near infrared hyper-spectral teeth database—a first step in the development of reliable diagnostic tool for quantification and early detection of caries," Lasers in Dentistry XVII, edited by P. Rechmann, D. Fried, Proceedings of SPIE, vol. 7884, Paper 78840E (2011).
Maia, A., L. Karlsson, W. Margulis, A. Gomes, "Evaluation of two imaging techniques: near-infrared transillumination and dental radiographs for the detection of early approximal enamel canes," Dentomaxillofacial Radiology, vol. 40, pp. 429-433 (2011).
Chung, S., D. Fried, M. Staninec, C.L. Darling, "Multispectral near-IR reflectance and transillumination imaging of teeth," Biomedical Optics Express, vol. 2, No. 10, pp. 2804-2814 (2011).

(56) References Cited

OTHER PUBLICATIONS

Chung, S., D. Fried, M. Staninec, C.L. Darling, "Near infrared imaging of teeth at wavelengths between 1200 and 1600nm," Proceedings of the Society of Photo Optical Instrument Engineering, paper 7884 (2011).
Staninec, M., S.M. Douglas, C.L. Darling, K. Chan, H. Kang, R. C. Lee, D. Fried, "Nondestructive clinical assessment of occlusal caries lesions using near-IR imaging methods," Lasers in Surgery and Medicine, vol. 43, No. 10, pp. 951-959 (2011).
Nishizawa, N., "Generation and application of high-quality supercontinuum sources," Optical Fiber Technology, vol. 18, pp. 394-402 (2012).
Istepanian, Robert H., "The Comparative Performance of Mobile Telemedical Systems based on the IS-54 and GSM Cellular Telephone Standards"; Journal of Telemedicine and Telecare 1999; pp. 97-104.
Aris, Ishak Bin, "An Internet-Based Blood Pressure Monitoring System for Patients"; Journal of Telemedicine and Telecare 2001; pp. 51-53.
Sun, Y., C.F. Booker, S. Kumari, R.N. Day, M. Davidson, A. Periasamy, "Characterization of an orange acceptor fluorescent protein for sensitized spectral fluorescence resonant energy transfer microscopy using a white-light laser," Journal of Biomedical Optics, vol. 14, No. 5, paper 054009 (2009).
Borlinghaus, R., "Colours Count: how the challenge of fluorescence was solved in confocal microscopy," in Modern Research and Educational Topics in Microscopy, A. Mendez-Vilas and J. Diaz, eds, pp. 890-899, Formatex (2007).
Borlinghaus, R., "The White Confocal: Continuous Spectral Tuning in Excitation and Emission," in Optical Fluorescence Microscopy, A. Diaspro (Ed), Chapter 2, pp. 37-54, ISBN 978-3-642-15174-3, Springer-Verlag, Berlin (2011).
Borlinghaus, R.T., L. Kuschel, "White Light Laser: The Ultimate Source for Confocal Microscopy," http://www.leica-microsystems.com/science-lab/white-light-laser (Jun. 27, 2012).
Ziegler, U., A.G. Bittermann, M. Hoechli, "Introduction to Confocal Laser Scanning Microscopy (LEICA)," www.zmb.unizh.ch, May 29, 2013.
"Application Brief the role of infrared microprobe analysis in forensic drug analysis," www.smithsdetection.com, Jun. 27, 2005.
Jasco Application Note No. 200DR0188-E, "Rapid Identification of illegal drug using NIR (identification of MDMA tablet)", Sep. 4, 2008.
Palou, A. J. Cruz, M. Blanco, J. Tomas, J. De Los Rios, M. Alcala, "Determination of drug, excipients and coating distribution in pharmaceutical tablets using NIR-CI," Journal of Pharmaceutical Analysis, vol. 2, No. 2, pp. 90-97 (2012).
Arnold, T., M. De Biasio, R. Leitner, "Near-Infrared Imaging Spectroscopy for Counterfeit Drug Detection," Next Generation Spectroscopic Technologies IV, edited by M. A. Druy, R.A. Crocombe, Proceedings of SPIE, vol. 8032, 80320Y-1 to 7, (2011).
Wedding, B.B., C. Wright, S. Grauf, R.D. White, "The application of near infrared spectroscopy for the assessment of avocado quality attributes," Infrared Spectroscopy—Life and Biomedical Sciences, pp. 211-230 (2011).
Michaels, C.A., T. Masiello, P.M. Chu, "Fourier transform spectrometry with a near infrared supercontinuum source," Optical Society of America, CLEO/IQEC Conference, paper CMDD6 (2009).
Michaels, C.A., T. Masiello, P.M. Chu, "Fourier transform spectrometry with a near-infrared supercontinuum source," Applied Spectroscopy, vol. 63, No. 5, pp. 538-543 (2009).
Moros,J., J. Kuligowski, G. Quintas, S. Garrigues, M. DeLa Guardia, "New cut-off criterion for uninformative variable elimination in multivariate calibration of near-infrared spectra for the determination of heroin in illicit street drugs," Analytica Chimica Acta, vol. 630, pp. 150-160 (2008).
Moros, J. N. Gallpienso, R. Vilches, S. Garrigues, M. DeLa Guardia, "Nondestructive direct determination of heroin in seized illicit street drugs by diffuse reflectance near-infrared spectroscopy," Analytical Chemistry, vol. 80, No. 19, pp. 7257-7265 (Oct. 1, 2008).
Roggo, Y. P. Chalus, L. Maurer, C. Lema-Martinez, A. Edmond, N. Jent, "A review of near infrared spectroscopy and chemometrics in pharmaceutical technologies," Journal of Pharmaceutical and Biomedical Analysis, vol. 44, pp. 683-700 (2007).
Pojic, M. J. Mastilovic, N. Majcen, "The application of near infrared spectroscopy in wheat quality control," Infrared Spectroscopy—Life and Biomedical Sciences, pp. 167-184 (2012).
Reich, G. "Near-infrared spectroscopy and imaging: basic principles and pharmaceutical applications," Advanced Drug Delivery Reviews, vol. 57, pp. 1109-1143 (2005).
Rodionova, O.Y., L.P. Houmoller, A.L. Pomerantsev, P. Geladi, J. Burger, V.L. Dorofeyev, A.P. Arzamastsev, "NIR spectrometry for counterfeit drug detection: a feasibility study," Analytica Chimica Acta, vol. 549, pp. 151-158 (2005).
Schneider, R.C., K.A. Kovar, "Analysis of ecstasy tablets: comparison of reflectance and transmittance near infrared spectroscopy," Forensic Science International, vol. 134, pp. 187-195 (2003).
Olsen, B.A., M.W. Borer, F.M. Perry, R.A. Forbes, "Screening for counterfeit drugs using near-infrared spectroscopy," Pharmaceutical Technology, pp. 62-71 (Jun. 2002).
Scafi, S.H.F., C. Pasquini, "Identification of counterfeit drugs using near-infrared spectroscopy," Analyst, vol. 126, pp. 2218-2224 (2001).
Sondermann, N., K.A. Kovar, "Identification of ecstasy in complex matrices using near-infrared spectroscopy," Forensic Science International, vol. 102, pp. 133-147 (1999).
Rambla, F.J., S. Garrigues, M. DeLa Guardia, "PLS-NIR determination of total sugar, glucose, fructose and sucrose in aqueous solutions of fruit juices," Analytica Chimica Acta, vol. 344, pp. 41-53 (1997).
Bizheva, K, et al., "Compact, broad-bandwidth fiberlaserforsub-2-pm axial resolution optical coherence tomography in the 1300-nm wavelength region," Optics Letters, vol. 28, No. 9, May 1, 2003, pp. 707-709.
Wang, Yimin, et al., "Ultrahigh-resolution optical coherence tomography by broadband continuum generation from a photonic crystal fiber", Optics Letters, vol. 28, No. 3, Feb. 1, 2003, pp. 182-184.
Seefeldt, Michael, et al., "Compact white-light source with an average output power of 2.4 Wand 900 nm spectral bandwidth", Optics Communications 216, pp. 199-202.
Xie, T.-Q., et al., "Detection of tumorigenesis in urinary bladder with optical coherence tomography: optical characterization of morphological changes", Optics Express, vol. 10, No. 24, Dec. 2, 2002, 2003, pp. 1431-1443.
Povazay, B., et al., "Submicrometer axial resolution optical coherence tomography", Optical Letters, vol. 27, No. 20, Oct. 15, 2002, pp. 1800-1802.
Kowalevicz, Andrew M., et al., "Ultrahigh resolution optical coherence tomography using a superluminescent light source" Optics Express 349, vol. 10, No. 7, Apr. 8, 2002, pp. 349-353.
Oughstun, Kurt E., "Influence of precursor fields on ultrashort pulse autocorrelation measurements and pulse width evolution", Optics Express, vol. 8, No. 8, Apr. 9, 2001, pp. 481-491.
Li Xingde, et al., "Imaging needle for optical coherence tomography", Optics Letters, vol. 25, No. 20, Oct. 15, 2000, pp. 1520-1522.
D'Amico, Anthony V., et al., "Optical Coherence Tomography as a Method for Identifying Benign and Malignant Microscopic Structures in the Prostate Gland", Basic Science, Urology 55 (5), 2000, pp. 783-787.
Rollins, Andrew M., et al., "Real-time in vivo imaging of human gastrointestinal ultrastructure by use of endoscopic optical coherence tomography with a novel efficient interferometer design", Optics Letters, vol. 24, No. 19, Oct. 1, 1999, pp. 1358-1360.
De Boer, Johannes F., et al., "Determination of the depth-resolved Stokes parameters of light backscattered from turbid media by use of polarization-sensitive optical coherence omography", Optics Letters, vol. 24, No. 5; Mar. 1, 1999, pages 300-302.
Roggan, Andre, et al., "Optical Properties of Circulating Human Blood in the Wavelength Range 400-2500 NM", Journal of Biomedical Optics, vol. 4, No. 1, Jan. 1999, pp. 36-46.
De Boer, Johannes F., et al., "Imaging thermally damaged tissue by polarization sensitive optical coherence tomography", Optics Express 212, vol. 3, No. 6, Sep. 14, 1998, pp. 212-218.

(56) References Cited

OTHER PUBLICATIONS

Tearney, Guillermo J., et al., "In vivo Endoscopic Optical Biopsy with Optical Coherence Tomography", Science, New Series, vol. 276, Jun. 27, 1997, pp. 2037-2039.
Boppart, Stephen A., et al., "Noninvasive assessment of the developing Xenopus cardiovascular system using optical coherence tomography", Prec. Natl. Acad. Sci. USA, vol. 94, Apr. 1997, pp. 4256-4261.
Boppart, Stephen A., et al., "Imaging developing neural morphology using optical coherence tomography", Journal of Neuroscience Methods 70, 1996, pp. 65-72.
Aaviksoo, J., et al., "Observation of optical precursors at pulse propagation in GaAs", Physical Review A, vol. 44, No. 9, Nov. 1, 1991, pp. R5353-R5356.
Harrington, James A., "Infrared Fiber Optics", OSA Handbook, vol. III, white paper, to be published by McGraw Hill, Undated, 13 pages.
Fedotova, O., et al., "Supercontinuum generation in planar rib waveguides enabled by anomalous dispersion", Optics Express, vol. 14, No. 4, Feb. 20, 2006, pp. 1512-1517.
Moon, Sucbei, et al., "Generation of octave-spanning supercontinuum with I550-nm amplified diode-laser pulses and a dispersion-shifted fiber", Optics Express, vol. 14, No. 1, Jan. 9, 2006, pp. 270-278.
Hagen, C. L., et al., "Generation of a Continuum Extending to the Midinfrared by Pumping ZBLAN Fiber With an Ultrafast 1550-nm Source", IEEE Photonics Technology Letters, vol. 18, No. 1, Jan. 1, 2006, pp. 91-93.
Travers, J. C., et al., "Extended blue supercontinuum generation in cascaded holey fibers", Optics Letters, vol. 30, No. 23, Dec. 1, 2005, pp. 3132-3134.
Schreiber, T., et al., "Supercontinuum generation by femtosecond single and dual wavelength pumping in photonic crystal fibers with two zero dispersion wavelengths", Optics Express, vol. 13, No. 23, Nov. 14, 2005, pp. 9556-9569.
Genty, G., et al., "Supercontinuum generation in large mode-area microstructured fibers", Optics Express, vol. 13, No. 21, Oct. 17, 2005, pp. 8625-8633.
Lee, Ju Han, et al., "Continuous-wave supercontinuum laser based on an erbium-doped fiber ring cavity incorporating a highly nonlinear optical fiber", Optics Letters, vol. 30, No. 19, Oct. 1, 2005, pp. 2599-2601.
J.G. Webster; Design of Pulse Oximeters; Medical Science Series; Taylor & Francis Group; CRC Press; Oct. 23, 1997; 260 pps.
H. Harry Asada et al.; Mobile Monitoring With Wearable Photoplethysmographic Biosensors; IEEE Engineering in Medicine and Biology Magazine, Jun. 2003; 13 pps.
United States District Court Eastern District of Texas Marshall Division; Defendant and Counter Claimant Apple Inc.'s Amended Answer, Affirmative Defenses, and Counterclaims to Complaint of Plaintiff and Counter Defendant Omni Medsci, Inc.; Document 38; Jul. 19, 2018; 32 pps.
Pan, Yingtian, et al., "Hand-held arthroscopic optical coherence tomography for in vivo high-resolution imaging of articular cartilage", Journal of Biomedical Optics 8(4), Oct. 2003, pp. 648-654.
Xie, Tuqiang, et al., "Endoscopic optical coherence tomography with a modified microelectromechanical systems mirror for detection of bladder cancers", Applied Optics, vol. 42, No. 31, Nov. 1, 2003, pp. 6422-6426.
Dubois, A., et al., "Three-dimensional cellular-level imaging using full-field optical coherence tomography", Physics in Medicine and Biology, Phys. Med. Biol. 49, 2004, pp. 1227-1234.
Park, Jesung, et al., "Analysis of birefringent image in the retinal nerve fiber layer by polarization sensitive optical coherence tomography", Ophthalmic Technologies XIV, Proceedings of SPIE, vol. 5314, 2004, pp. 188-194.
Unterhuber, A., et al., "Advances in broad bandwidth light sources for ultrahigh resolution optical coherence tomography", Physics in Medicine and Biology, Phys. Med. Biol. 49, 2004, pp. 1235-1246.

Drexler, Wolfgang, "Ultrahigh-resolution optical coherence tomography", Journal of Biomedical Optics, vol. 9, No. 1, Jan./Feb. 2004, pp. 47-74.
Schmitt, Joseph, et al., "Intravascular Optical Coherence Tomography Opens a Window Onto Coronary Artery Disease", Optics & Photonics News, Feb. 2004, pp. 20-25.
Nassif, N. A., et al., "In vivo high-resolution video-rate spectral-domain optical coherence tomography of the human retina and optic nerve", Optics Express, vol. 12, No. 3, Feb. 9, 2004, pp. 367-375.
Choi, Seung-Ho, et al., "Observation of Optical Precursors in Water", Physical Review Letters, vol. 92, No. 19, May 14, 2004, pp. 193903-1-193903-3.
Pierce, Mark C., et al., "Advances in Optical Coherence Tomography imaging for Dermatology", Optical Coherence Tomography Advances, The Journal of Investigative Dermatology, Sep. 3, 2004, pp. 458-463.
"State-Specific Trends in Chronic Kidney Failure—United States, 1990-2001", Morbidity and Mortality Weekly Report, Department of Health and Human Services Centers for Disease Control and Prevention, vol. 53, No. 39, copied from internet: file://C:\Documents and Settings\eturlo\Desktop\State-Specific Trends in Chronic Kidney . . . Feb. 12, 2010, Oct. 8, 2004, pp. 918-920.
I.B. Ads, A.A.E. Wagie, N.B. Mariun, A.B.E. Jammal, "An Internet-based blood pressure monitoring system for patients," Journal of Telemedicine and Telecare, 2001, pp. 51-53.
R.H. Istepanian, B. Woodward, P.A. Bales, S. Chen, B. Luk, "The comparative performance of mobile telemediCal systems based on the IS-54 and GSM cellular telephone standards," Journal of Telemedicine and Telecare, 1999, pp. 97-104.
Shaw, et al, IR Supercontinuum Generation in As—Se Photonic Crystal Fiber, Optical Society of America, Copyright 2005, 3 pages.
PCT/US06/44451, Notification of Transmittal of the International Search Report and the Written Opinion of the International Searching Authority, or the Declaration, dated Nov. 29, 2007, 12 pages.
G.S. Edwards et al., "Free-electron-laser-based biophysical and biomedical instrumentation," American Institute of Physics, vol. 74, No. 7, Jul. 2003, pp. 3207-3245.
Computer Motion, Inc., "501(k) Summary—ZEUS® MicroWrist™ Surgical System and Accessories," Sep. 24, 2002, 6 pages.
Computer Motion, Inc. "HERMES™ O.R. Control Center—510(k) Summary of Safety and Effectiveness," Oct. 11, 2002, 5 pages.
K.M. Joos, et al. "Optic Nerve Sheath Fenestration with a Novel Wavelength Produced by the Free Electron Laser (FEL)," Lasers in Surgery and Medicine, 27: 2000,191-205.
J. Sanghera, I. Aggarwal, "IR Fiber Optics at NRL," undated, 10 pages.
J. Sanghera, L.B. Shaw, I.D. Aggarwal, "Applications of chalcogenide glass optical fibers," Academic of Science, 2003, pp. 1-11.
B. Rigas, P.T.T. Wong, "Human Colon Adenocarcinoma Cell Lines Display Infrared Spectroscopic Features," Cancer Research, Jan. 1, 1992, pp. 84-88.
G. Edwards, et al., "Comparison of OPA and Mark-III FEL for Tissue Ablation at 6.45 Microns," Department of Physics and Free Electron Laser Laboratory, Duke University, 2002, 7 pages.
Glenn Edwards, "Biomedical and potential clinical applications for pulsed lasers operating near 6.45 um," Society of Photo-Optical Instrumentation Engineers, 1995, 2 pages.
Passat, "Solid-State Lasers and Optical Components," Jul. 14, 2003, 5 pages.
P.A. Thielen and L.B. Shaw, et al., "Small-core As—Se fiber for Raman amplification," Optics Leti-ers, vol. 28, No. 16, Aug. 15, 2003, 3 pages.
R.Rox Anderson, et al., "Selective Photothermolysis: Precise Microsurgery by Selective Absorption of Pulsed Radiation," Department of Dermatology, Harvard Medical School, Science, vol. 220, Apr. 29, 1983, 4 pages.
U.S. Appl. No. 10/652,276, "System and Method for Voice Control of Medical devices," by Mohammed N. Islam, abandoned filed Aug. 29, 2003.
U.S. Appl. No. 10/757,341, "System and Method for Voice Control of Medical devices," by Mohammed N. Islam, issued filed Jan. 13, 2004.

(56) References Cited

OTHER PUBLICATIONS

U.S. Appl. No. 12/206,432, "System and Method for Voice Control of Medical Devices," by Mohammed N. Islam, pending filed Sep. 8, 2008.
U.S. Patent and Trademark Office, Office Action for U.S. Appl. No. 12/206,432, filed Sep. 8, 2008, Mohammed N, Islam, Date Filed: Mar. 12, 2009.
U.S. Patent and Trademark Office, Notice of Allowance and Fee(s) Due for U.S. Appl. No. 12/206,432, filed Sep. 8, 2008, Mohammed N. Islam, Date filed: Aug. 28, 2009.
International Search Report and Written Opinion for International Application No. PCT/US2013/075700 dated Apr. 24, 2014.
International Preliminary Report on Patentability for International Application No. PCT/US2013/075700 dated Jul. 9, 2015.
Li et al, A Wireless Reflective Pulse Oximeter with Digital Baseline Control for Unfiltered Photoplethysmograms, (Jun. 2012) IEEE Transactions on Biomedical Circuits and Systems, vol. 6, No. 3, 10 pages.
Humphreys et al., Noncontact Simultaneous Dual Wavelength Photoplethysmography: A Further Step Toward Noncontact Pulse Oximetry, (2007) Review of Scientific Instruments 78, 044304, American Institute of Physics, 6 pages.
Mendelson et al., A Wearable Reflectance Pulse Oximeter for Remote Physiological Monitoring, (Aug./Sep. 2006) Proceedings of the 28th IEEE EMBS Annual International Conference New York City, Ny, 4 pages.
United States District Court Eastern District of Texas Marshall Division; *Omni Medsci, Inc.* vs. *Apple Inc.*; Civil Action No. 2:18-cv-00134 Jury Trial Demanded; Defendant's Invalidity Contentions; Aug. 28, 2018; 33 pps.
*Omni Medsci, Inc.* V. *Apple Inc.*; Case No. 2:18-cv-134-RWS (E.D. Tex.); Defendant's Invalidity Contentions, Aug. 28, 2018 (Exhibit A), 66 pps.
*Omni Medsci, Inc.* V. *Apple Inc.*; Case No. 2:18-cv-134-RWS (E.D. Tex.); Defendant's Invalidity Contentions, Aug. 28, 2018 (Exhibit B), 73 pps.
*Omni Medsci, Inc.* V. *Apple Inc.*; Case No. 2:18-cv-134-RWS (E.D. Tex.); Defendant's Invalidity Contentions, Aug. 28, 2018 (Exhibit C), 85 pps.
*Omni Medsci, Inc.* V. *Apple Inc.*; Case No. 2:18-cv-134-RWS (E.D. Tex.); Defendant's Invalidity Contentions, Aug. 28, 2018 (Exhibit D), 38 pps.
*Omni Medsci, Inc.* V. *Apple Inc.*; Case No. 2:18-cv-134-RWS (E.D. Tex.); Defendants Invalidity Contentions, Aug. 28, 2018 (Exhibit E), 120 pps.
*Omni Medsci, Inc.* V. *Apple Inc.*; Case No. 2:18-cv-134-RWS (E.D. Tex.); Defendants Invalidity Contentions, Aug. 28, 2018 (Exhibit F), 40 pps.
*Omni Medsci, Inc.* V. *Apple Inc.*; Case No. 2:18-cv-134-RWS (E.D. Tex.); Defendants Invalidity Contentions, Aug. 28, 2018 (Exhibit G), 66 pps.
*Omni Medsci, Inc.* V. *Apple Inc.*; Case No. 2:18-cv-134-RWS (E.D. Tex.); Defendants Invalidity Contentions, Aug. 28, 2018 (Exhibit H), 74 pps.
*Omni Medsci, Inc.* V. *Apple Inc.*; Case No. 2:18-cv-134-RWS (E.D. Tex.); Defendants Invalidity Contentions, Aug. 28, 2018 (Exhibit I), 102 pps.
*Omni Medsci, Inc.* V. *Apple Inc.*; Case No. 2:18-cv-134-RWS (E.D. Tex.); Defendants Invalidity Contentions, Aug. 28, 2018 (Exhibit J), 64 pps.
*Omni Medsci, Inc.* V. *Apple Inc.*; Case No. 2:18-cv-134-RWS (E.D. Tex.); Defendants Invalidity Contentions, Aug. 28, 2018 (Exhibit K), 77 pps.
*Omni Medsci, Inc.* V. *Apple Inc.*; Case No. 2:18-cv-134-RWS (E.D. Tex.); Defendants Invalidity Contentions, Aug. 28, 2018 (Exhibit L), 64 pps.
*Omni Medsci, Inc.* V. *Apple Inc.*; Case No. 2:18-cv-134-RWS (E.D. Tex.); Defendants Invalidity Contentions, Aug. 28, 2018 (Exhibit M), 119 pps.
*Omni Medsci, Inc.* V. *Apple Inc.*; Case No. 2:18-cv-134-RWS (E.D. Tex.); Defendants Invalidity Contentions, Aug. 28, 2018 (Exhibit N), 50 pps.
*Omni Medsci, Inc.* V. *Apple Inc.*; Case No. 2:18-cv-134-RWS (E.D. Tex.); Defendants Invalidity Contentions, Aug. 28, 2018 (Exhibit O), 63 pps.
*Omni Medsci, Inc.* V. *Apple Inc.*; Case No. 2:18-cv-134-RWS (E.D. Tex.); Defendants Invalidity Contentions, Aug. 28, 2018 (Exhibit P), 78 pps.
*Omni Medsci, Inc.* V. *Apple Inc.*; Case No. 2:18-cv-134-RWS (E.D. Tex.); Defendants Invalidity Contentions, Aug. 28, 2018 (Exhibit Q), 69 pps.
*Omni Medsci, Inc.* V. *Apple Inc.*; Case No. 2:18-cv-134-RWS (E.D. Tex.); Defendants Invalidity Contentions, Aug. 28, 2018 (Exhibit R), 61 pps.
*Omni Medsci, Inc.* V. *Apple Inc.*; Case No. 2:18-cv-134-RWS (E.D. Tex.); Defendants Invalidity Contentions, Aug. 28, 2018 (Exhibit S), 50 pps.
*Omni Medsci, Inc.* V. *Apple Inc.*; Case No. 2:18-cv-134-RWS (E.D. Tex.); Defendants Invalidity Contentions, Aug. 28, 2018 (Exhibit T), 174 pps.
*Omni Medsci, Inc.* V. *Apple Inc.*; Case No. 2:18-cv-134-RWS (E.D. Tex.); Defendants Invalidity Contentions, Aug. 28, 2018 (Exhibit U), 334 pps.
*Omni Medsci, Inc.* V. *Apple Inc.*; Case No. 2:18-cv-134-RWS (E.D. Tex.); Defendants Invalidity Contentions, Aug. 28, 2018 (Exhibit V), 137 pps.
*Omni Medsci, Inc.* V. *Apple Inc.*; Case No. 2:18-cv-134-RWS (E.D. Tex.); Defendants Invalidity Contentions, Aug. 28, 2018 (Exhibit W), 384 pps.
*Omni Medsci, Inc.* V. *Apple Inc.*; Case No. 2:18-cv-134-RWS (E.D. Tex.); Defendants Invalidity Contentions, Aug. 28, 2018 (Exhibit X), 291 pps.
*Omni Medsci, Inc.* V. *Apple Inc.*; Case No. 2:18-cv-134-RWS (E.D. Tex.); Defendants Invalidity Contentions, Aug. 28, 2018 (Exhibit Y), 120 pps.
*Omni Medsci, Inc.* V. *Apple Inc.*; Case No. 2:18-cv-134-RWS (E.D. Tex.); Defendants Invalidity Contentions, Aug. 28, 2018 (Exhibit Z), 53 pps.
*Omni Medsci, Inc.* V. *Apple Inc.*; Case No. 2:18-cv-134-RWS (E.D. Tex.); Defendants Invalidity Contentions, Aug. 28, 2018 (Exhibit AA), 75 pps.
*Omni Medsci, Inc.* V. *Apple Inc.*; Case No. 2:18-cv-134-RWS (E.D. Tex.); Defendants Invalidity Contentions, Aug. 28, 2018 (Exhibit BB), 65 pps.
*Omni Medsci, Inc.* V. *Apple Inc.*; Case No. 2:18-cv-134-RWS (E.D. Tex.); Defendants Invalidity Contentions, Aug. 28, 2018 (Exhibit CC), 320 pps.
*Omni Medsci, Inc.* V. *Apple Inc.*; Case No. 2:18-cv-134-RWS (E.D. Tex.); Defendants Invalidity Contentions, Aug. 28, 2018 (Exhibit DD), 240 pps.
Rhee et al., Artifact-Resistant Power-Efficient Design of Finger-Ring Plethysmographic Sensors, IEEE Transactions on Biomedical Engineering (Jul. 2001), vol. 48, No. 7, Cambridge, MA, 11 pages.
Branche et al., Signal Quality and Power Consumption of a New Prototype Reflectance Pulse Oximeter Sensor, Proceedings of the IEEE 31st Annual Northeast Bioengineering Conference (2005), Hoboken, NJ, 2 pages.
Peláez, LED Power Reduction Trade-Offs for Ambulatory Pulse Oximetry, Conference Proceedings of the 29th Annual International Conference of the IEEE EMBS (Aug. 2007) Lyon, France, 4 pages.
Luo et al., A Non-Invasive Dual-Channel Oximeter Based on Near-Infrared Spectroscopy (NIRS), Biophotonics Lab, Center of Advanced Research in Photonics (2007), The Chinese University of Hong Kong, China, 2 pages.
Asada et al., The MIT Ring: History, Technology, and Challenges of Wearable Health Monitoring, MIT Industrial Liaison Program (2010) R&D Conference, MA, 72 pages.
Asada et al., Mobile Monitoring with Wearable Photoplethysmographic Biosensors, Technical and Clinical Aspects of a Ring Sensor for Ambulatory, Telemetric, Continuous Health Monitoring in the Field, in the Hospital, and in the Home, IEEE Engineering in Medicine and Biology Magazine, (May/Jun. 2003) 13 pages.

(56) References Cited

OTHER PUBLICATIONS

Schreiner et al., Blood Oxygen Level Measurement with a Chest-Based Pulse Oximetry Prototype System, Computing in Cardiology (2010) NIBEC, University of Ulster, Newtownabbey, Northern Ireland, 4 pages.
GE Healthcare, TuffSat User's Guide and Service Manual Electromagnetic Compatibility (EMC), (Mar. 2005) Helsinki, Finland, 43 pages.
Kurylyak et al., Smartphone-Based Photoplethysmogram Measurement, Department of Electronics, Computer and System Sciences, (2012) River Publishers, University of Calabria, Italy, 30 pages.
Patterson et al., Ratiometric Artifact Reduction in Low Power Reflective Photoplethysmography, (Aug. 2011) IEEE Transactions on Biomedical Circuits and Systems, vol. 5, No. 4, 9 pages.
Cai et al., Implementation of a Wireless Pulse Oximeter Based on Wrist Band Sensor, College of Biological Science and Medical Engineering Southeast University, (2010) 3rd International Conference on Biomedical Engineering and Informatics, Nanjing, China, 4 pages.
Yamaha, BODiBEAT, Body, Music, in Sync., BF-1 Quick Guide, Player/Heart Rate Monitor: Quick Manual, 120 pages.
GE Healthcare, GE Ohmeda TufSat Oximeter for Clinicians on the go, (2012), A General Electric Co., www.gehealthcare.com, GE, Finland, 4 pages.
Wang et al., Multichannel Reflective PPG Earpiece Sensor with Passive Motion Cancellation, (Dec. 2007) IEEE Transactions on Biomedical Circuits and Systems, vol. 1, No. 4, 7 pages.
Webster, Design of Pulse Oximeters, Medical Science Series (1997), Department of Electrical and Computer Engineering, University of Wisconsin—Madison, Institute of Physics Publishing, Bristol and Philadelphia, 267 pages.
Taos, Inc., Infrared Light-to-Voltage Optical Sensors, (2006) Texas Advanced Optoelectronic Solutions Inc., The Lumenology Company, TX, 14 pages.
Jung et al., Design of a Low-Power Consumption Wearable Reflectance Pulse Oximetry for Ubiquitous Healthcare System, International Conference on Control, Automation and Systems (Oct. 2008), in COEX, Seoul, Korea, 4 pages.
Embedded-Lab, Introducing Easy Pulse: A DIY Photoplethysmographic Sensor for Measuring Hearth Rate, posted on www.Embedded-Lab.com Sep. 12, 2012, by R-B, 10 pages.
Asare et al., Analysis of Multi-Spectral Photoplethysmograph Biosensors, Proc. SPIE 8801, Novel Biophotonic Techniques and Applications II, 880106 (Jun. 2013), European Conferences on Biomedical Optics, Munich, Germany, 7 pages.
Morón et al, A Wireless Monitoring System for Pulse-Oximetry Sensors, (2005) Electronic Technology Department, University of Malaga, Spain, 6 pages.

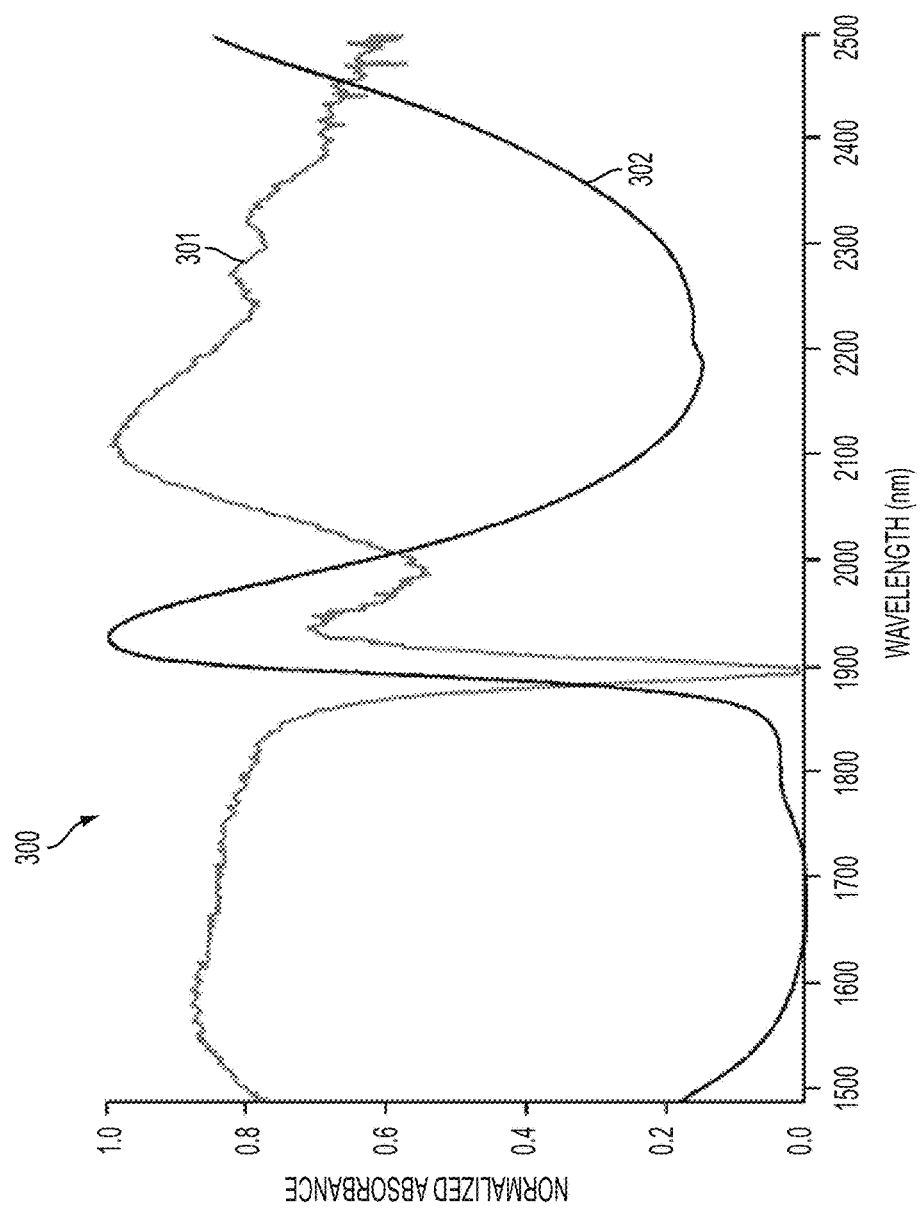

NEAR-INFRARED LASER DIODES USED IN IMAGING APPLICATIONS

CROSS-REFERENCE TO RELATED APPLICATIONS

This application is a continuation of U.S. application Ser. No. 15/888,052 filed Feb. 4, 2018, which is a continuation of U.S. application Ser. No. 15/212,549 filed Jul. 18, 2016, now U.S. Pat. No. 9,885,698 issued Feb. 6, 2018, which is a continuation of U.S. application Ser. No. 14/650,897 filed Jun. 10, 2015, now U.S. Pat. No. 9,494,567 issued Nov. 15, 2016, which is a U.S. National Phase of PCT/US2013/075700 filed Dec. 17, 2013, which claims the benefit of U.S. provisional application Ser. No. 61/747,472 filed Dec. 31, 2012, the disclosures of which are hereby incorporated in their entirety by reference herein.

This application is related to U.S. provisional application Ser. No. 61/747,477 filed Dec. 31, 2012; Ser. No. 61/747,481 filed Dec. 31, 2012; Ser. No. 61/747,485 filed Dec. 31, 2012; Ser. No. 61/747,487 filed Dec. 31, 2012; Ser. No. 61/747,492 filed Dec. 31, 2012; Ser. No. 61/747,553 filed Dec. 31, 2012; and Ser. No. 61/754,698 filed Jan. 21, 2013, the disclosures of which are hereby incorporated in their entirety by reference herein.

This application has a common priority date with International Application PCT/US2013/075736 entitled Short-Wave Infrared Super-Continuum Lasers For Early Detection Of Dental Caries; U.S. application Ser. No. 14/108,995 filed Dec. 17, 2013 entitled Focused Near-Infrared Lasers For Non-Invasive Vasectomy And Other Thermal Coagulation Or Occlusion Procedures; International Application PCT/US2013/075767 entitled Short-Wave Infrared Super-Continuum Lasers For Natural Gas Leak Detection, Exploration, And Other Active Remote Sensing Applications; U.S. application Ser. No. 14/108,986 filed Dec. 17, 2013 entitled Short-Wave Infrared Super-Continuum Lasers For Detecting Counterfeit Or Illicit Drugs And Pharmaceutical Process Control; U.S. application Ser. No. 14/108,974 filed Dec. 17, 2013 entitled Non-Invasive Treatment Of Varicose Veins; and U.S. application Ser. No. 14/109,007 filed Dec. 17, 2013 entitled Near-Infrared Super-Continuum Lasers For Early Detection Of Breast And Other Cancers, the disclosures of which are hereby incorporated in their entirety by reference herein.

BACKGROUND

With the growing obesity epidemic, the number of individuals with diabetes is also increasing dramatically. For example, there are over 200 million people who have diabetes. Diabetes control requires monitoring of the glucose level, and most glucose measuring systems available commercially require drawing of blood. Depending on the severity of the diabetes, a patient may have to draw blood and measure glucose four to six times a day. This may be extremely painful and inconvenient for many people. In addition, for some groups, such as soldiers in the battlefield, it may be dangerous to have to measure periodically their glucose level with finger pricks.

Thus, there is an unmet need for non-invasive glucose monitoring (e.g., monitoring glucose without drawing blood). The challenge has been that a non-invasive system requires adequate sensitivity and selectivity, along with repeatability of the results. Yet, this is a very large market, with an estimated annual market of over $10B in 2011 for self-monitoring of glucose levels.

One approach to non-invasive monitoring of blood constituents or blood analytes is to use near-infrared spectroscopy, such as absorption spectroscopy or near-infrared diffuse reflection or transmission spectroscopy. Some attempts have been made to use broadband light sources, such as tungsten lamps, to perform the spectroscopy. However, several challenges have arisen in these efforts. First, many other constituents in the blood also have signatures in the near-infrared, so spectroscopy and pattern matching, often called spectral fingerprinting, is required to distinguish the glucose with sufficient confidence. Second, the non-invasive procedures have often transmitted or reflected light through the skin, but skin has many spectral artifacts in the near-infrared that may mask the glucose signatures. Moreover, the skin may have significant water and blood content. These difficulties become particularly complicated when a weak light source is used, such as a lamp. More light intensity can help to increase the signal levels, and, hence, the signal-to-noise ratio.

As described in this disclosure, by using brighter light sources, such as fiber-based supercontinuum lasers, superluminescent laser diodes, light-emitting diodes or a number of laser diodes, the near-infrared signal level from blood constituents may be increased. By shining light through the teeth, which have fewer spectral artifacts than skin in the near-infrared, the blood constituents may be measured with less interfering artifacts. Also, by using pattern matching in spectral fingerprinting and various software techniques, the signatures from different constituents in the blood may be identified. Moreover, value-add services may be provided by wirelessly communicating the monitored data to a handheld device such as a smart phone, and then wirelessly communicating the processed data to the cloud for storing, processing, and transmitting to several locations.

SUMMARY OF EXAMPLE EMBODIMENTS

In one embodiment, a smart phone or tablet comprises one or more laser diodes configured to be pulsed and to generate light having one or more optical wavelengths, wherein at least a portion of the one or more optical wavelengths is a near-infrared wavelength between 700 nanometers and 2500 nanometers. A first one or more lenses is configured to receive a portion of the light from the one or more laser diodes and to direct at least some portion of the received light to tissue. An array of laser diodes is configured to be pulsed and to generate light having one or more optical wavelengths, wherein at least a portion of the one or more optical wavelengths is a near-infrared wavelength between 700 nanometers and 2500 nanometers. A second one or more lenses is configured to receive a portion of the light from the array of laser diodes, the array of laser diodes and the second one or more lenses configured to form the light into a plurality of spots and to direct at least some of the spots to tissue. An infrared camera is configured to be synchronized to the at least one of the one or more laser diodes to receive at least a portion of light reflected from the tissue from at least one of the one or more laser diodes, wherein the infrared camera generates data based at least in part on the received light. The infrared camera is further configured to be synchronized to the array of laser diodes to receive light from at least a portion of the plurality of spots reflected from the tissue, and wherein the infrared camera generates additional data based at least in part on the received light. The infrared camera is further configured to: receive light while the one or more laser diodes and the array of laser diodes are off and convert the received light into a first signal; and receive light while at least some of the one or more laser diodes or some of the array of laser diodes are on, and convert the received light into a second signal, the received light including at least a part of the portion of the light from the at least one of the one or more laser diodes reflected from the tissue, or at least a part of the portion of the light from the array of laser diodes reflected from the tissue. The smart phone or tablet is configured to generate a two-dimensional or three-dimensional image using a difference between the first signal and the second signal, and using at least part of the data or at least part of the additional data from the infrared camera. The smart phone or tablet further comprises a wireless receiver, a wireless transmitter, a display, a voice input module, and a speaker.

Embodiments may include a smart phone or tablet comprising one or more laser diodes configured to be pulsed and to generate light having one or more optical wavelengths, wherein at least a portion of the one or more optical wavelengths is a near-infrared wavelength between 700 nanometers and 2500 nanometers. A first one or more lenses is configured to receive a portion of the light from the one or more laser diodes and to direct at least some portion of the received light to tissue. An array of laser diodes is configured to be pulsed and to generate light having one or more optical wavelengths, wherein at least a portion of the one or more optical wavelengths is a near-infrared wavelength between 700 nanometers and 2500 nanometers. A second one or more lenses is configured to receive a portion of the light from the array of laser diodes, the array of laser diodes and the second one or more lenses configured to form the light into a plurality of spots and to direct at least some of the spots to tissue. An infrared camera is configured to be synchronized to the at least one of the one or more laser diodes to receive at least a portion of light reflected from the tissue from at least one of the one or more laser diodes, and wherein the infrared camera generates data based at least in part on the received light. The infrared camera is further configured to be synchronized to the array of laser diodes to receive light from at least a portion of the plurality of spots reflected from the tissue, wherein the infrared camera generates additional data based at least in part on the received light. The smart phone or tablet is configured to generate a two-dimensional or three-dimensional image using at least part of the data or part of the additional data from the infrared camera. The smart phone or tablet further comprises a wireless receiver, a wireless transmitter, a display, a voice input module, and a speaker.

In one embodiment, a smart phone or tablet comprises one or more laser diodes configured to be pulsed and to generate light having one or more optical wavelengths, wherein at least a portion of the one or more optical wavelengths is a near-infrared wavelength between 700 nanometers and 2500 nanometers. A first one or more lenses is configured to receive a portion of the light from the one or more laser diodes and to direct at least some portion of the received light to tissue. An array of laser diodes is configured to be pulsed and to generate light having one or more optical wavelengths, wherein at least a portion of the one or more optical wavelengths is a near-infrared wavelength between 700 nanometers and 2500 nanometers. A second one or more lenses is configured to receive a portion of the light from the array of laser diodes, the array of laser diodes and the second one or more lenses configured to form the light into a plurality of spots and to direct at least some of the spots to tissue, wherein the plurality of spots are also formed at least in part by using an assembly in front of the array of laser diodes. An infrared camera is configured to be synchronized to the at least one of the one or more laser diodes to receive at least a portion of light reflected from the tissue from at least one of the one or more laser diodes, wherein the infrared camera generates data based at least in part on the received light. The infrared camera is further configured to be synchronized to the array of laser diodes to receive light from at least a portion of the plurality of spots reflected from the tissue, wherein the infrared camera generates additional data based at least in part on the received light. The smart phone or tablet is configured to generate a two-dimensional or three-dimensional image using at least part of the data or part of the additional data from the infrared camera. The smart phone or tablet further comprises a wireless receiver, a wireless transmitter, a display, a voice input module, and a speaker.

BRIEF DESCRIPTION OF THE DRAWINGS

For a more complete understanding of the present disclosure, and for further features and advantages thereof, reference is now made to the following description taken in conjunction with the accompanying drawings, in which:

FIG. 3A shows the normalized absorbance of water and glucose (not drawn to scale). Water shows transmission windows between about 1500-1850 nm and 2050-2500 nm.

DETAILED DESCRIPTION

Figure 1:
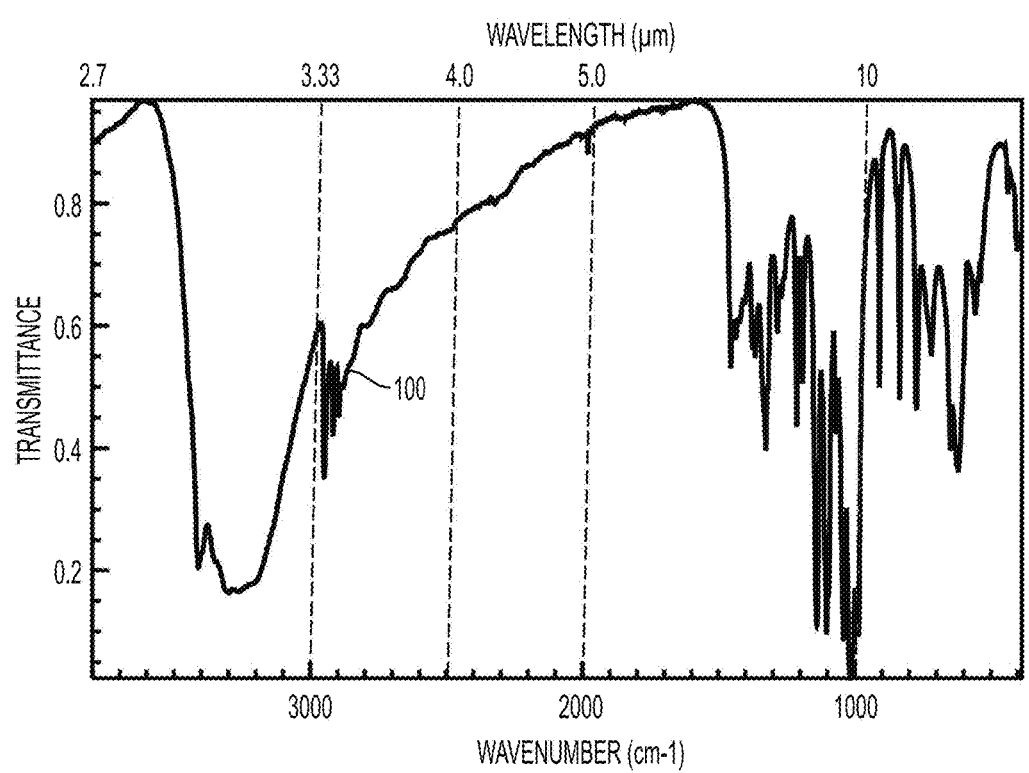
FIG. 1 plots the transmittance versus wavenumber for glucose in the mid-wave and long-wave infrared wavelengths between approximately 2.7 to 12 microns.

As required, detailed embodiments of the present disclosure are disclosed herein; however, it is to be understood that the disclosed embodiments are merely exemplary of the disclosure that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

Various ailments or diseases may require measurement of the concentration of one or more blood constituents. For example, diabetes may require measurement of the blood glucose and HbA1c levels. On the other hand, diseases or disorders characterized by impaired glucose metabolism may require the measurement of ketone bodies in the blood. Examples of impaired glucose metabolism diseases include Alzheimer's, Parkinson's, Huntington's, and Lou Gehrig's or amyotrophic lateral sclerosis (ALS). Techniques related to near-infrared spectroscopy or hyper-spectral imaging may be particularly advantageous for non-invasive monitoring of some of these blood constituents.

Hyper-spectral images may provide spectral information to identify and distinguish between spectrally similar materials, providing the ability to make proper distinctions among materials with only subtle signature differences. In the SWIR wavelength range, numerous gases, liquids and solids have unique chemical signatures, particularly materials comprising hydro-carbon bonds, O—H bonds, N—H bonds, etc. Therefore, spectroscopy in the SWIR may be attractive for stand-off or remote sensing of materials based on their chemical signature, which may complement other imaging information.

One embodiment of remote sensing that is used to identify and classify various materials is so-called "hyper-spectral imaging." Hyper-spectral sensors may collect information as a set of images, where each image represents a range of wavelengths over a spectral band. Hyper-spectral imaging may deal with imaging narrow spectral bands over an approximately continuous spectral range. As an example, in hyper-spectral imaging the sun may be used as the illumination source, and the daytime illumination may comprise direct solar illumination as well as scattered solar (skylight), which is caused by the presence of the atmosphere. However, the sun illumination changes with time of day, clouds or inclement weather may block the sun light, and the sun light is not accessible in the night time. Therefore, it would be advantageous to have a broadband light source covering the SWIR that may be used in place of the sun to identify or classify materials in remote sensing or stand-off detection applications.

In one embodiment, a SWIR camera or infrared camera system may be used to capture the images. The camera may include one or more lenses on the input, which may be adjustable. The focal plane assemblies may be made from mercury cadmium telluride material (HgCdTe), and the detectors may also include thermo-electric coolers. Alternately, the image sensors may be made from indium gallium arsenide (InGaAs), and CMOS transistors may be connected to each pixel of the InGaAs photodiode array. The camera may interface wirelessly or with a cable (e.g., USB, Ethernet cable, or fiber optics cable) to a computer or tablet or smart phone, where the images may be captured and processed. These are a few examples of infrared cameras, but other SWIR or infrared cameras may be used and are intended to be covered by this disclosure.

Described herein are just some examples of the beneficial use of near-infrared or SWIR lasers for active remote sensing or hyper-spectral imaging. However, many other spectroscopy and identification procedures can use the near-infrared or SWIR light consistent with this disclosure and are intended to be covered by the disclosure. As one example, the fiber-based super-continuum lasers may have a pulsed output with pulse durations of approximately 0.5-2 nsec and pulse repetition rates of several Megahertz. Therefore, the active remote sensing or hyper-spectral imaging applications may also be combined with LIDAR-type applications. Namely, the distance or time axis can be added to the information based on time-of-flight measurements. For this type of information to be used, the detection system would also have to be time-gated to be able to measure the time difference between the pulses sent and the pulses received. By calculating the round-trip time for the signal, the distance of the object may be judged. In another embodiment, GPS (global positioning system) information may be added, so the active remote sensing or hyper-spectral imagery would also have a location tag on the data. Moreover, the active remote sensing or hyper-spectral imaging information could also be combined with two-dimensional or three-dimensional images to provide a physical picture as well as a chemical composition identification of the materials. These are just some modifications of the active remote sensing or hyper-spectral imaging system described in this disclosure, but other techniques may also be added or combinations of these techniques may be added, and these are also intended to be covered by this disclosure.

Described herein are just some examples of the beneficial use of near-infrared or SWIR lasers for active remote sensing or hyper-spectral imaging. However, many other spectroscopy and identification procedures can use the near-infrared or SWIR light consistent with this disclosure and are intended to be covered by the disclosure. As one example, the fiber-based super-continuum lasers may have a pulsed output with pulse durations of approximately 0.5-2 nsec and pulse repetition rates of several Megahertz. Therefore, the active remote sensing or hyper-spectral imaging applications may also be combined with LIDAR-type applications. Namely, the distance or time axis can be added to the information based on time-of-flight measurements. For this type of information to be used, the detection system would also have to be time-gated to be able to measure the time difference between the pulses sent and the pulses received. By calculating the round-trip time for the signal, the distance of the object may be judged. In another embodiment, GPS (global positioning system) information may be added, so the active remote sensing or hyper-spectral imagery would also have a location tag on the data. Moreover, the active remote sensing or hyper-spectral imaging information could also be combined with two-dimensional or three-dimensional images to provide a physical picture as well as a chemical composition identification of the materials. These are just some modifications of the active remote sensing or hyper-spectral imaging system described in this disclosure, but other techniques may also be added or combinations of these techniques may be added, and these are also intended to be covered by this disclosure.

In some instances, it may be desirable to create multiple locations of focused light on the varicose vein. For example, the speed of the treatment may be increased by causing thermal coagulation or occlusion at multiple locations. Multiple collimated or focused light beams may be created in one assembly. In this embodiment, optionally a surface cooling apparatus may be used, where a cooling fluid may be flowed either touching or in close proximity to the skin. Also, in this particular embodiment a cylindrical assembly may optionally be used, where the cylindrical length may be several millimeters in length and defined by a clamp or mount placed on or near the leg. In one embodiment, a window and/or lenslet array is also shown on the cylindrical surface for permitting the light to be incident on the skin and varicose vein at multiple spots. The lenslet array may comprise circular, spherical or cylindrical lenses, depending on the type of spots desired. As before, one advantage of placing the lenslet array in close proximity to the skin and varicose vein may be that a high NA, lens may be used. Also, the input from the lens and/or mirror assembly to the lenslet array may be single large beam, or a plurality of smaller beams. In one embodiment, a plurality of spots may be created by the lenslet array to cause a plurality of locations of thermal coagulation in the varicose vein. Any number of spots may be used and are intended to be covered by this disclosure.

In a non-limiting example, a plurality of spots may be used, or what might be called a fractionated beam. The fractionated laser beam may be added to the laser delivery assembly or delivery head in a number of ways. In one embodiment, a screen-like spatial filter may be placed in the pathway of the beam to be delivered to the biological tissue. The screen-like spatial filter can have opaque regions to block the light and holes or transparent regions, through which the laser beam may pass to the tissue sample. The ratio of opaque to transparent regions may be varied, depending on the application of the laser. In another embodiment, a lenslet array can be used at or near the output interface where the light emerges. In yet another embodiment, at least a part of the delivery fiber from the infrared laser system to the delivery head may be a bundle of fibers, which may comprise a plurality of fiber cores surrounded by cladding regions. The fiber cores can then correspond to the exposed regions, and the cladding areas can approximate the opaque areas not to be exposed to the laser light. As an example, a bundle of fibers may be excited by at least a part of the laser system output, and then the fiber bundle can be fused together and perhaps pulled down to a desired diameter to expose to the tissue sample near the delivery head. In yet another embodiment, a photonic crystal fiber may be used to create the fractionated laser beam. In one non-limiting example, the photonic crystal fiber can be coupled to at least a part of the laser system output at one end, and the other end can be coupled to the delivery head. In a further example, the fractionated laser beam may be generated by a heavily multi-mode fiber, where the speckle pattern at the output may create the high intensity and low intensity spatial pattern at the output. Although several exemplary techniques are provided for creating a fractionated laser beam, other techniques that can be compatible with optical fibers are also intended to be included by this disclosure.

Although the output from a fiber laser may be from a single or multi-mode fiber, different spatial spot sizes or spatial profiles may be beneficial for different applications. For example, in some instances it may be desirable to have a series of spots or a fractionated beam with a grid of spots. In one embodiment, a bundle of fibers or a light pipe with a plurality of guiding cores may be used. In another embodiment, one or more fiber cores may be followed by a lenslet array to create a plurality of collimated or focused beams. In yet another embodiment, a delivery light pipe may be followed by a grid-like structure to divide up the beam into a plurality of spots. These are specific examples of beam shaping, and other apparatuses and methods may also be used and are consistent with this disclosure.

As used throughout this document, the term "couple" and or "coupled" refers to any direct or indirect communication between two or more elements, whether or not those elements are physically connected to one another. As used throughout this disclosure, the term "spectroscopy" means that a tissue or sample is inspected by comparing different features, such as wavelength (or frequency), spatial location, transmission, absorption, reflectivity, scattering, refractive index, or opacity. In one embodiment, "spectroscopy" may mean that the wavelength of the light source is varied, and the transmission, absorption or reflectivity of the tissue or sample is measured as a function of wavelength. In another embodiment, "spectroscopy" may mean that the wavelength dependence of the transmission, absorption or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this document, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or light-pipe. In one embodiment, the gain fiber may be doped with rare earth material, such as ytterbium, erbium, and/or thulium. In another embodiment, the mid-infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam is coupled to a gain medium to excite the gain medium, which in turn may amplify another input optical signal or beam. In one particular example, the gain medium may be a doped fiber, such as a fiber doped with ytterbium, erbium or thulium. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and or "supercontinuum" and or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth of at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, the Raman effect, modulational instability, and self-phase modulation.

As used throughout this disclosure, the terms "optical light" and or "optical beam" and or "light beam" refer to photons or light transmitted to a particular location in space. The "optical light" and or "optical beam" and or "light beam" may be modulated or unmodulated, which also means that they may or may not contain information. In one embodiment, the "optical light" and or "optical beam" and or "light beam" may originate from a fiber, a fiber laser, a laser, a light emitting diode, a lamp, a pump laser, or a light source. In general, the "near-infrared (NIR)" region of the electromagnetic spectrum covers between approximately 0.7 microns (700 nm) to about 2.5 microns (2500 nm). However, it may also be advantageous to use just the short-wave infrared between approximately 1.4 microns (1400 nm) and about 2.5 microns (2500 nm). One reason for preferring the SWIR over the entire NIR may be to operate in the so-called "eye-safe" window, which corresponds to wavelengths longer than about 1400 nm. Therefore, for the remainder of the disclosure the SWIR will be used for illustrative purposes. However, it should be clear that the discussion that follows could also apply to using the NIR wavelength range, or other wavelength bands.

Spectrum for Glucose

One molecule of interest is glucose. The glucose molecule has the chemical formula $C_6H_{12}O_6$, so it has a number of hydro-carbon bonds. An example of the infrared transmittance of glucose 100 is illustrated in FIG. 1. The vibrational spectroscopy shows that the strongest lines for bending and stretching modes of C—H and O—H bonds lie in the wavelength range of approximately 6-12 microns. However, light sources and detectors are more difficult in the mid-wave infrared and long-wave infrared, and there is also strongly increasing water absorption in the human body beyond about 2.5 microns. Although weaker, there are also nonlinear combinations of stretching and bending modes between about 2 to 2.5 microns, and first overtone of C—H stretching modes between approximately 1.5-1.8 microns. These signatures may fall in valleys of water absorption, permitting non-invasive detection through the body. In addition, there are yet weaker features from the second overtones and higher-order combinations between about 0.8-1.2 microns; in addition to being weaker, these features may also be masked by absorption in the hemoglobin. Hence, the short-wave infrared (SWIR) wavelength range of approximately 1.4 to 2.5 microns may be an attractive window for near-infrared spectroscopy of blood constituents.

Figure 2:
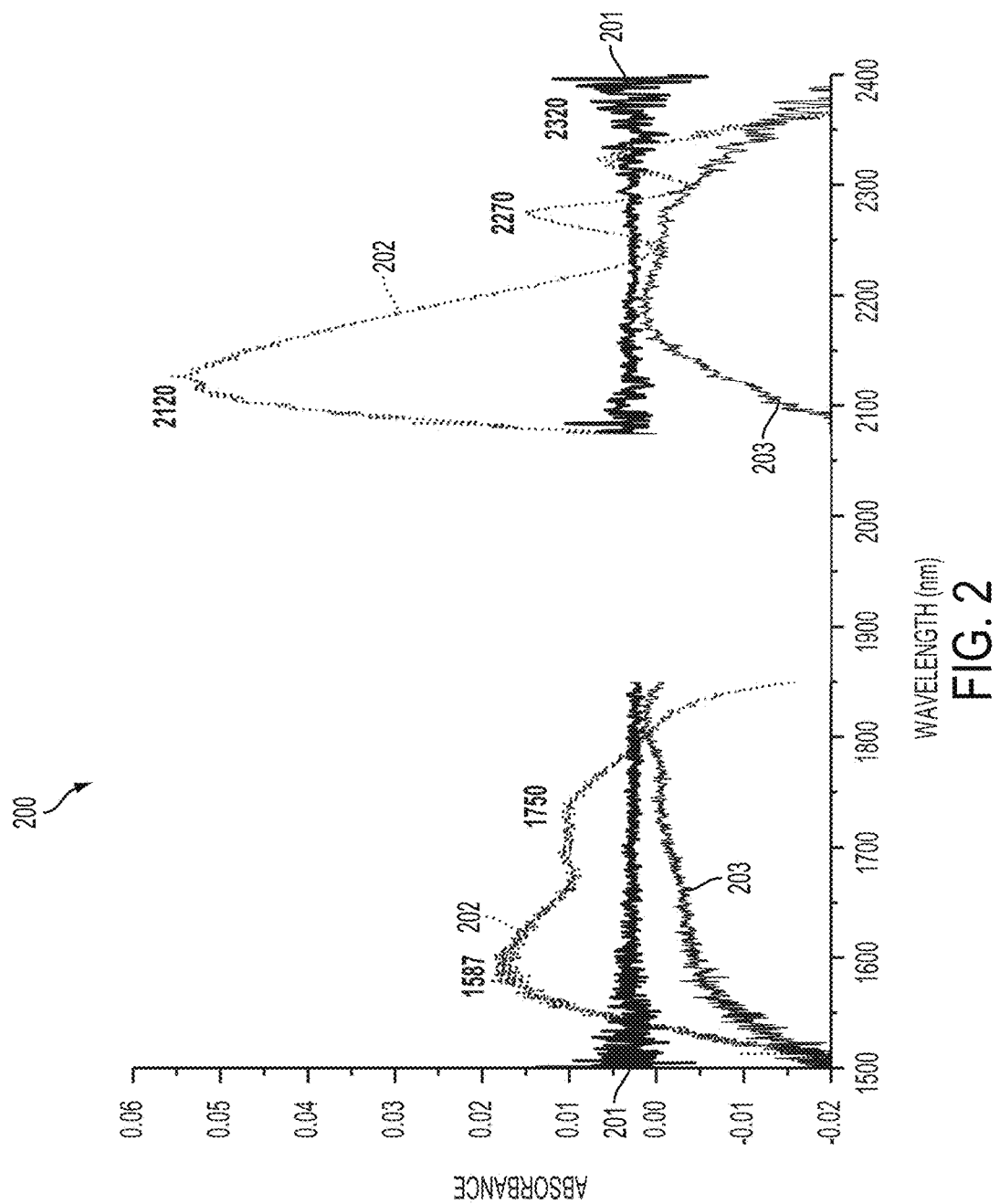
FIG. 2 illustrates measurements of the absorbance of different blood constituents, such as glucose, hemoglobin, and hemoglobin A1c. The measurements are done using an FTIR spectrometer in samples with a 1 mm path length.

As an example, measurements of the optical absorbance 200 of hemoglobin, glucose and HbA1c have been performed using a Fourier-Transform Infrared Spectrometer—FTIR. As FIG. 2 shows, in the SWIR wavelength range hemoglobin is nearly flat in spectrum 201 (the noise at the edges is due to the weaker light signal in the measurements). On the other hand, the glucose absorbance 202 has at least five distinct peaks near 1587 nm, 1750 nm, 2120 nm, 2270 nm and 2320 nm.

Figure 3B:
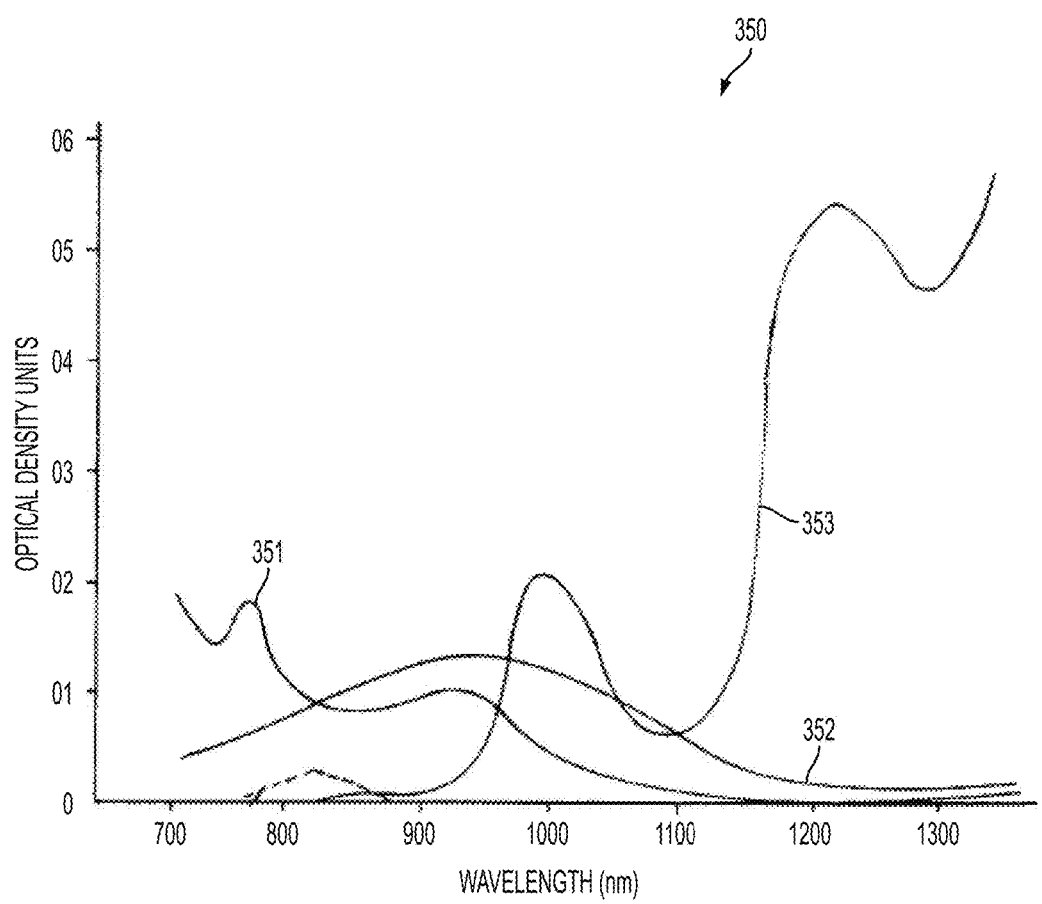
FIG. 3B illustrates the absorbance of hemoglobin and oxygenated hemoglobin overlapped with water.

FIG. 3A overlaps 300 the normalized absorbance of glucose 301 with the absorbance of water 302 (not drawn to scale). It may be seen that water has an absorbance feature between approximately 1850 nm and 2050 nm, but water 302 also has a nice transmission window between approximately 1500-1850 nm and 2050 to 2500 nm. For wavelengths less than about 1100 nm, the absorption of hemoglobin 351 and oxygenated hemoglobin 352 in FIG. 3B has a number of features 350, which may make it more difficult to measure blood constituents. Also, beyond 2500 nm the water absorption becomes considerably stronger over a wide wavelength range. Therefore, an advantageous window for measuring glucose and other blood constituents may be in the SWIR between 1500 and 1850 nm and 2050 to 2500 nm.

These are exemplary wavelength ranges, and other ranges can be used that would still fall within the scope of this disclosure.

One further consideration in choosing the laser wavelength is known as the "eye safe" window for wavelengths longer than about 1400 nm. In particular, wavelengths in the eye safe window may not transmit down to the retina of the eye, and therefore, these wavelengths may be less likely to create permanent eye damage. The near-infrared wavelengths have the potential to be dangerous, because the eye cannot see the wavelengths (as it can in the visible), yet they can penetrate and cause damage to the eye. Even if a practitioner is not looking directly at the laser beam, the practitioner's eyes may receive stray light from a reflection or scattering from some surface. Hence, it can always be a good practice to use eye protection when working around lasers. Since wavelengths longer than about 1400 nm are substantially not transmitted to the retina or substantially absorbed in the retina, this wavelength range is known as the eye safe window. For wavelengths longer than 1400 nm, in general only the cornea of the eye may receive or absorb the light radiation.

Figure 4A:
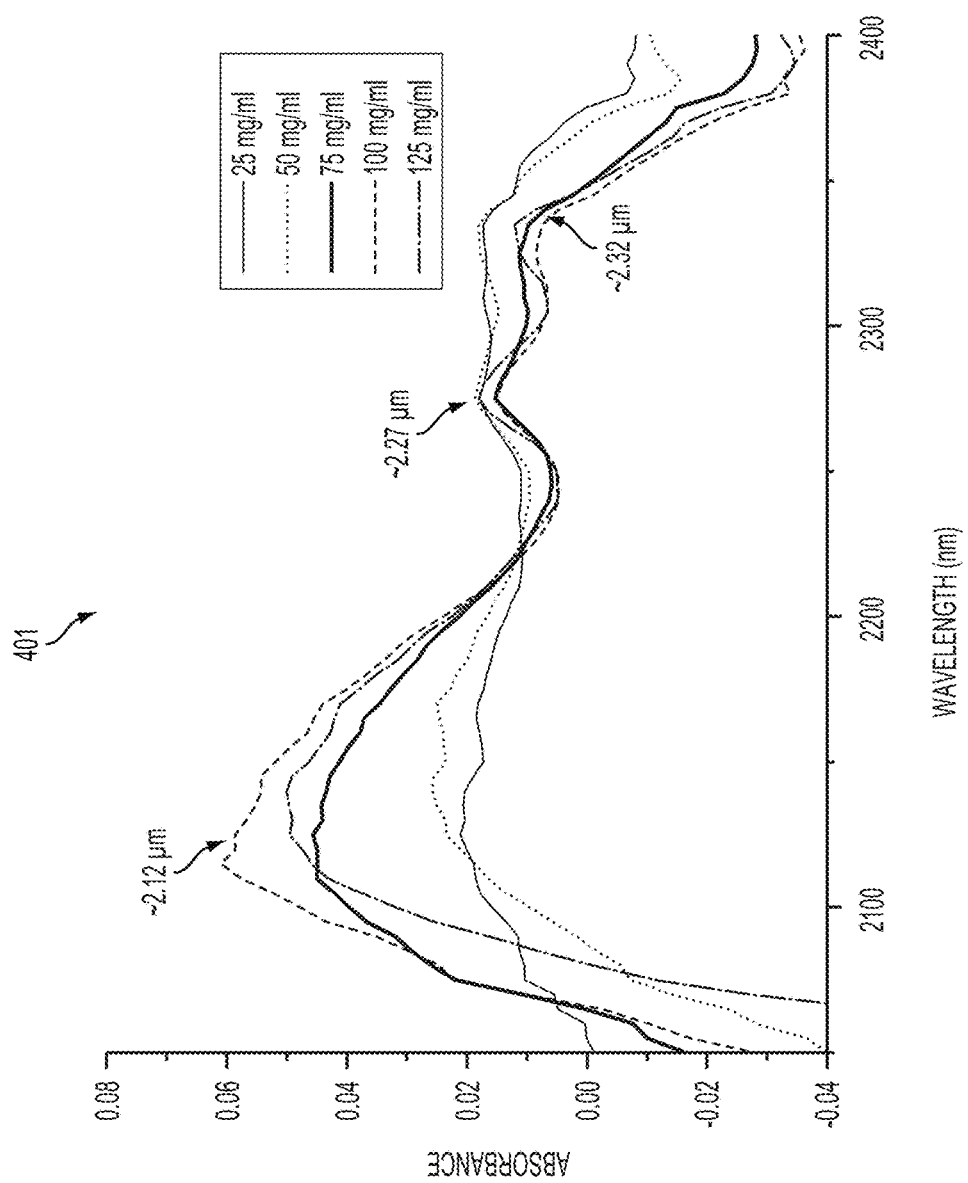
FIG. 4A shows measured absorbance in different concentrations of glucose solution over the wavelength range of about 2000 to 2400 nm. This data is collected using a SWIR super-continuum laser with the sample path length of about 1.1 mm.
Figure 4B:
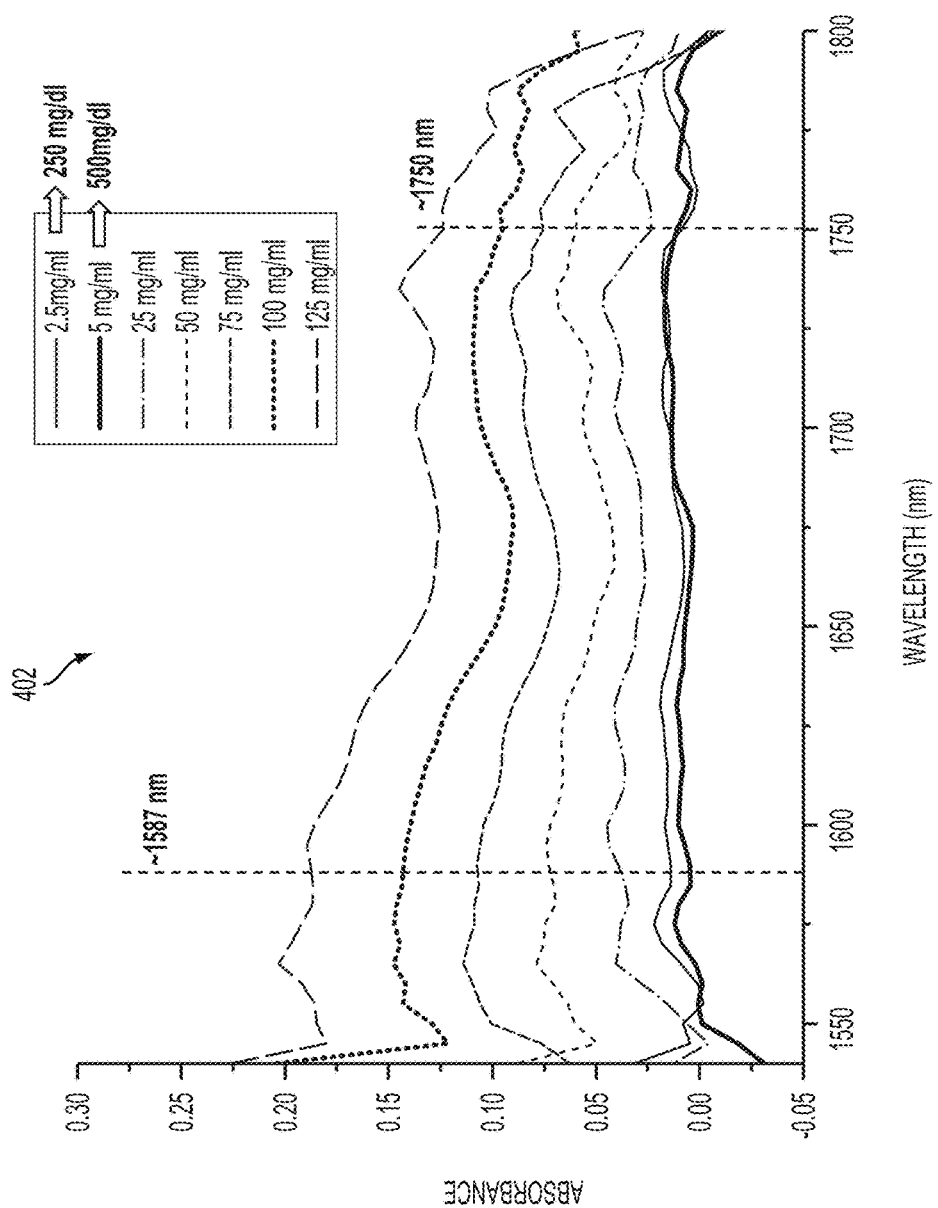
FIG. 4B illustrates measured absorbance in different concentrations of glucose solution over the wavelength range of about 1550 to 1800 nm. The data is collected using a SWIR super-continuum laser with a sample path length of about 10 mm.

Beyond measuring blood constituents such as glucose using FTIR spectrometers, measurements have also been conducted in another embodiment using super-continuum lasers, which will be described later in this disclosure. In this particular embodiment, some of the exemplary preliminary data for glucose absorbance are illustrated in FIGS. 4A and 4B. The optical spectra 401 in FIG. 4A for different levels of glucose concentration in the wavelength range between 2000 and 2400 nm show the three absorption peaks near 2120 nm (2.12 µm), 2270 nm (2.27 µm) and 2320 nm (2.32 µm). Moreover, the optical spectra 402 in FIG. 4B for different levels of glucose concentration in the wavelength range between 1500 and 1800 nm show the two broader absorption peaks near 1587 nm and 1750 nm. It should be appreciated that although data measured with FTIR spectrometers or super-continuum lasers have been illustrated, other light sources can also be used to obtain the data, such as super-luminescent laser diodes, light emitting diodes, a plurality of laser diodes, or even bright lamp sources that generate adequate light in the SWIR.

Figure 5:
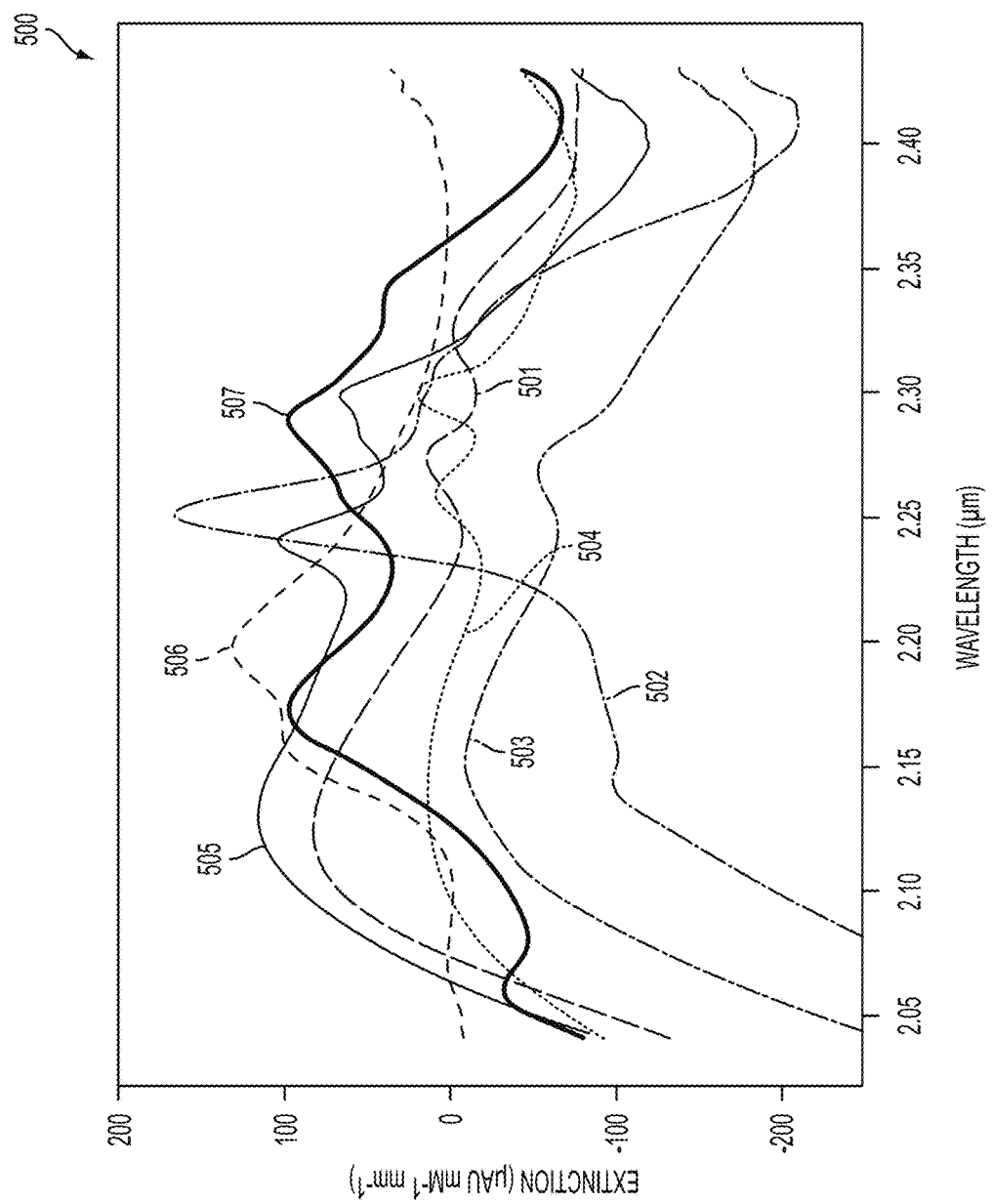
FIG. 5 illustrates the spectrum for different blood constituents in the wavelength range of about 2 to 2.45 microns (2000 to 2450 nm).

Although glucose has a distinctive signature in the SWIR wavelength range, one problem of non-invasive glucose monitoring is that many other blood constituents also have hydro-carbon bonds. Consequently, there can be interfering signals from other constituents in the blood. As an example, FIG. 5 illustrates the spectrum 500 for different blood constituents in the wavelength range of 2 to 2.45 microns. The glucose absorption spectrum 501 can be unique with its three peaks in this wavelength range. However, other blood constituents such as triacetin 502, ascorbate 503, lactate 504, alanine 505, urea 506, and BSA 507 also have spectral features in this wavelength range. To distinguish the glucose 501 from these overlapping spectra, it may be advantageous to have information at multiple wavelengths. In addition, it may be advantageous to use pattern matching algorithms and other software and mathematical methods to identify the blood constituents of interest. In one embodiment, the spectrum may be correlated with a library of known spectra to determine the overlap integrals, and a threshold function may be used to quantify the concentration of different constituents. This is just one way to perform the signal processing, and many other techniques, algorithms, and software may be used and would fall within the scope of this disclosure.

Ketone Bodies Monitoring

Beyond glucose, there are many other blood constituents that may also be of interest for health or disease monitoring. In another embodiment, it may be desirous to monitor the level of ketone bodies in the blood stream. Ketone bodies are three water-soluble compounds that are produced as by-products when fatty acids are broken down for energy in the liver. Two of the three are used as a source of energy in the heart and brain, while the third is a waste product excreted from the body. In particular, the three endogenous ketone bodies are acetone, acetoacetic acid, and beta-hydroxybutyrate or 3-hydroxybutyrate, and the waste product ketone body is acetone.

Ketone bodies may be used for energy, where they are transported from the liver to other tissues. The brain may utilize ketone bodies when sufficient glucose is not available for energy. For instance, this may occur during fasting, strenuous exercise, low carbohydrate, ketogenic diet and in neonates. Unlike most other tissues that have additional energy sources such as fatty acids during periods of low blood glucose, the brain cannot break down fatty acids and relies instead on ketones. In one embodiment, these ketone bodies are detected.

Ketone bodies may also be used for reducing or eliminating symptoms of diseases or disorders characterized by impaired glucose metabolism. For example, diseases associated with reduced neuronal metabolism of glucose include Parkinson's disease, Alzheimer's disease, amyotrophic lateral sclerosis (ALS, also called Lou Gehrig's disease), Huntington's disease and epilepsy. In one embodiment, monitoring of alternate sources of ketone bodies that may be administered orally as a dietary supplement or in a nutritional composition to counteract some of the glucose metabolism impairments is performed. However, if ketone bodies supplements are provided, there is also a need to monitor the ketone level in the blood stream. For instance, if elevated levels of ketone bodies are present in the body, this may lead to ketosis; hyperketonemia is also an elevated level of ketone bodies in the blood. In addition, both acetoacetic acid and beta-hydroxybutyric acid are acidic, and, if levels of these ketone bodies are too high, the pH of the blood may drop, resulting in ketoacidosis.

The general formula for ketones is $C_nH_{2n}O$. In organic chemistry, a ketone is an organic compound with the structure RC(=O)R', where R and R' can be a variety of carbon-containing substituents. It features a carbonyl group (C=O) bonded to two other carbon atoms. Because the ketones contain the hydrocarbon bonds, there might be expected to be features in the SWIR, similar in structure to those found for glucose.

Figure 6:
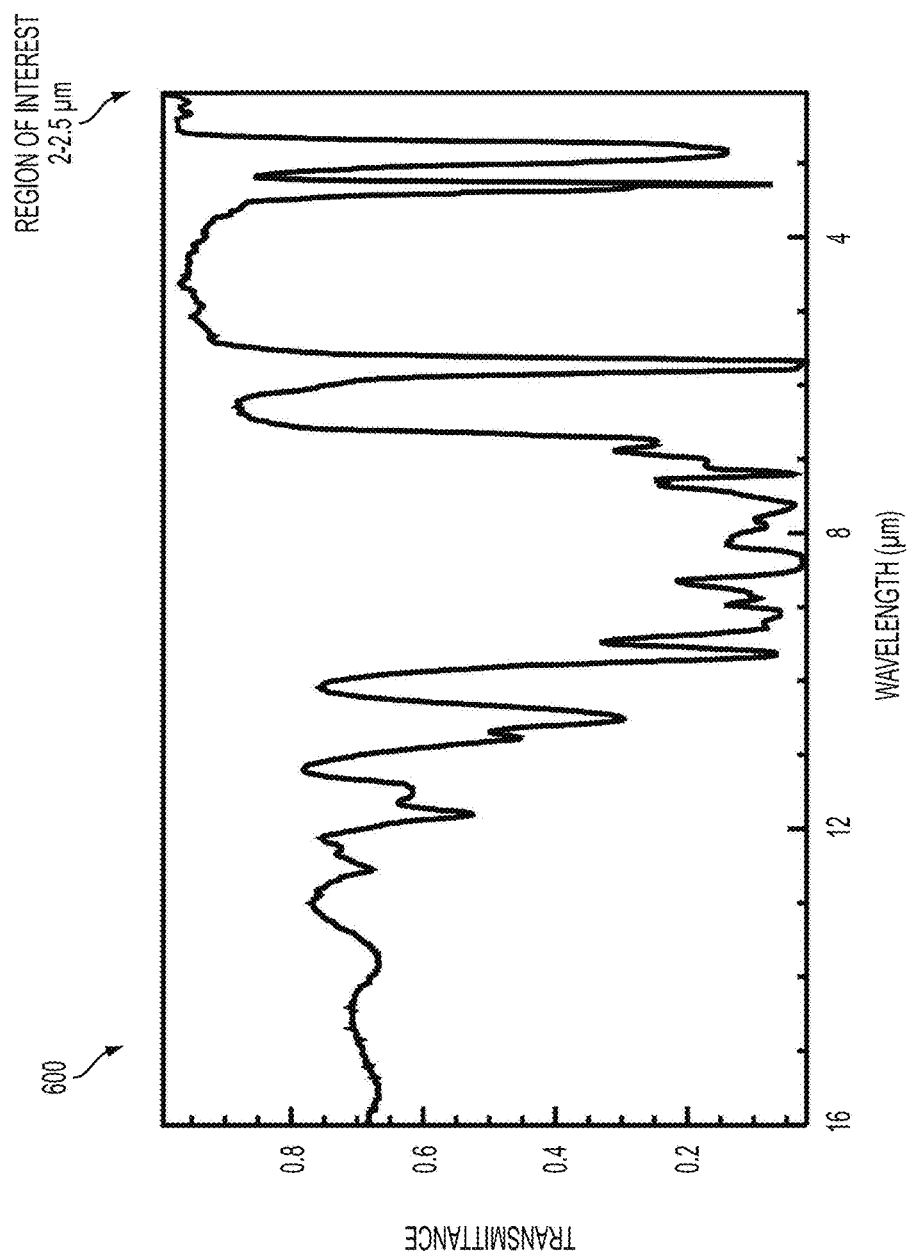
FIG. 6 shows the transmittance versus wavelength in microns for the ketone 3-hydroxybutyrate. The wavelength range is approximately 2 to 16 microns.

The infrared spectrum 600 for the ketone 3-hydroxybutyrate is illustrated in FIG. 6. Just as in glucose, there are significant features in the mid- and long-wave infrared between 6 to 12 microns, but these may be difficult to observe non-invasively. On the other hand, there are some features in the SWIR that may be weaker, but they could potentially be observed non-invasively, perhaps through blood and water.

Figure 7:
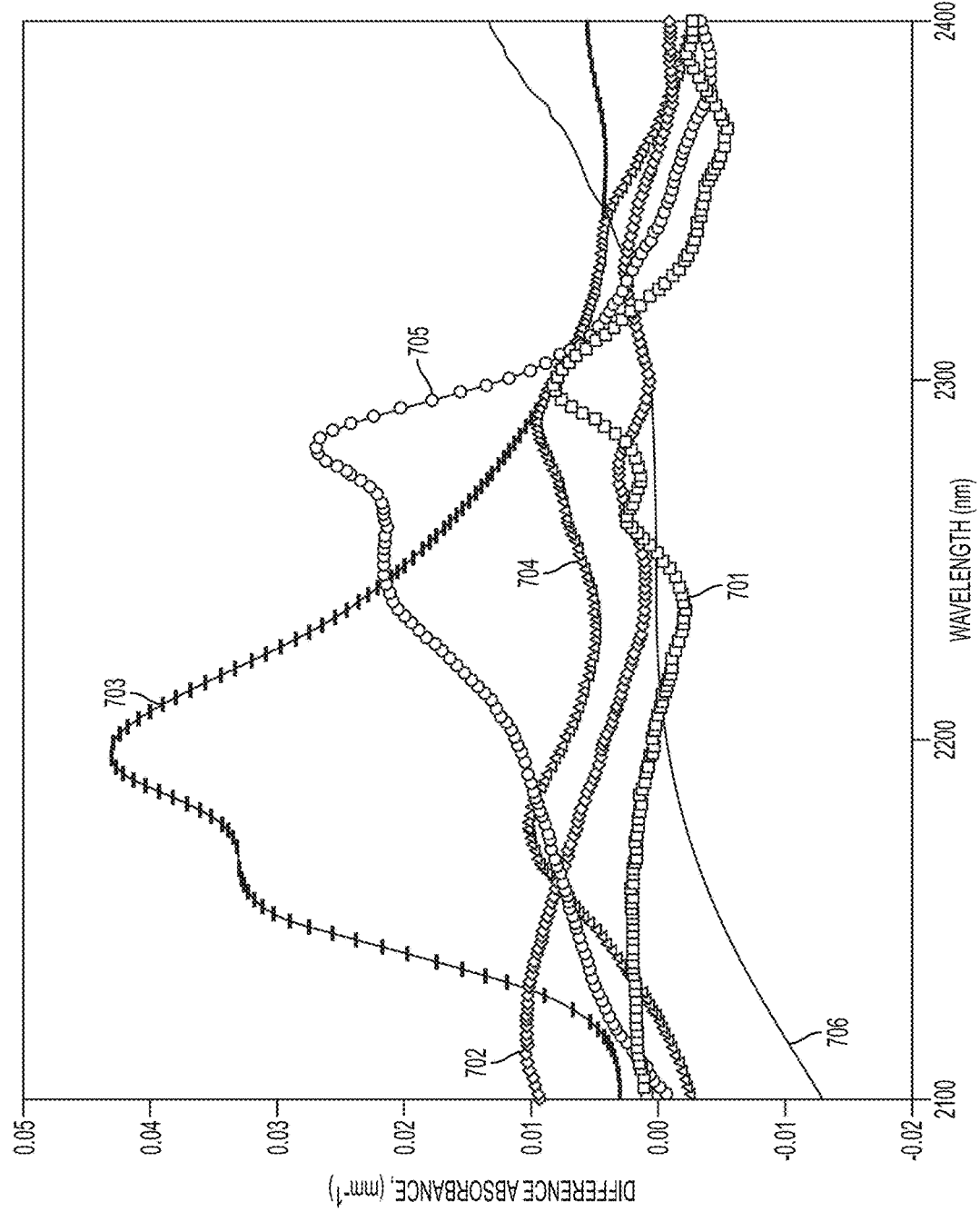
FIG. 7 illustrates the optical absorbance for ketones as well as some other blood constituents in the wavelength range of about 2100 to 2400 nm.

The optical spectra 700 for ketones as well as some other blood constituents are exemplified in FIG. 7 in the wavelength range of 2100 nm to 2400 nm. In this embodiment, the absorbance for ketones is 701, while the absorbance for glucose is 702. However, there are also features in this wavelength range for other blood constituents, such as urea 703, albumin or blood protein 704, creatinine 705, and nitrite 706. In this wavelength range of 2100 to 2400 nm, the features for ketone 701 seem more spectrally pronounced than even glucose.

Figure 8A:
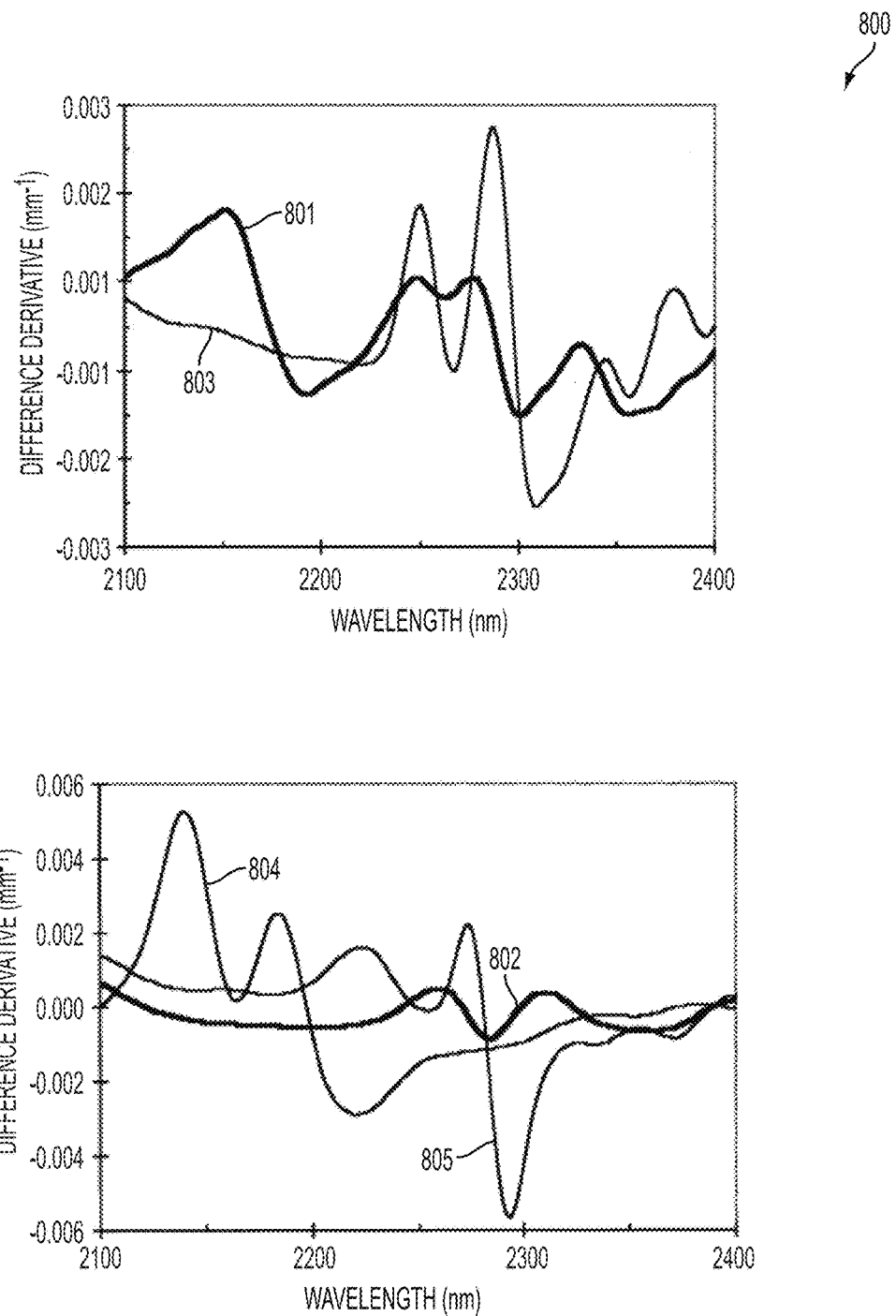
FIG. 8A shows the first derivative spectra of ketone and protein at concentrations of 10 g/L (left). In addition, the first derivative spectra of urea, creatinine, and glucose are shown on the right at concentrations of 10 g/L.

Different signal processing techniques can be used to enhance the spectral differences between different constituents. In one embodiment, the first or second derivatives of the spectra may enable better discrimination between substances. The first derivative may help remove any flat offset or background, while the second derivative may help to remove any sloped offset or background. In some instances, the first or second derivative may be applied after curve fitting or smoothing the reflectance, transmittance, or absorbance. For example, FIG. 8A illustrates the derivative spectra for ketone 801 and glucose 802, which can be distinguished from the derivative spectra for protein 803, urea 804 and creatinine 805. Based on FIG. 8A, it appears that ketones 801 may have a more pronounced difference than even glucose 802 in the wavelength range between 2100 and 2400 nm. Therefore, ketone bodies should also be capable of being monitored using a non-invasive optical technique in the SWIR, and a different pattern matching library could be used for glucose and ketones.

Hemoglobin A1c Monitoring

Another blood constituent that may be of interest for monitoring of health or diseases is hemoglobin A1c, also known as HbA1c or glycated hemoglobin (glycol-hemoglobin or glycosylated hemoglobin). HbA1c is a form of hemoglobin that is measured primarily to identify the average plasma glucose concentration over prolonged periods of time. Thus, HbA1c may serve as a marker for average blood glucose levels over the previous months prior to the measurements.

In one embodiment, when a physician suspects that a patient may be diabetic, the measurement of HbA1c may be one of the first tests that are conducted. An HbA1c level less than approximately 6% may be considered normal. On the other hand, an HbA1c level greater than approximately 6.5% may be considered to be diabetic. In diabetes mellitus, higher amounts of HbA1c indicate poorer control of blood glucose levels. Thus, monitoring the HbA1c in diabetic patients may improve treatment. Current techniques for measuring HbA1c require drawing blood, which may be inconvenient and painful. The point-of-care devices use immunoassay or boronate affinity chromatography, as an example. Thus, there is also an unmet need for non-invasive monitoring of HbA1c.

FIG. 2 illustrates the FTIR measurements of HbA1c absorbance 203 over the wavelength range between 1500 and 2400 nm for a concentration of approximately 1 mg/ml. Whereas the absorbance of hemoglobin 201 over this wavelength range is approximately flat, the HbA1c absorbance 203 shows broad features and distinct curvature. Although the HbA1c absorbance 203 does not appear to exhibit as pronounced features as glucose 202, the non-invasive SWIR measurement should be able to detect HbA1c with appropriate pattern matching algorithms. Moreover, the spectrum for HbA1c may be further enhanced by using first or second derivative data, as seen for ketones in FIG. 8A. Beyond absorption, reflectance, or transmission spectroscopy, it may also be possible to detect blood constituents such as HbA1c using Raman spectroscopy or surface-enhanced Raman spectroscopy. In general, Raman spectroscopy may require higher optical power levels.

As an illustration, non-invasive measurement of blood constituents such as glucose, ketone bodies, and HbA1c has been discussed thus far. However, other blood constituents can also be measured using similar techniques, and these are also intended to be covered by this disclosure. In other embodiments, blood constituents such as proteins, albumin, urea, creatinine or nitrites could also be measured. For instance, the same type of SWIR optical techniques might be used, but the pattern matching algorithms and software could use different library features or functions for the different constituents.

Figure 8B:
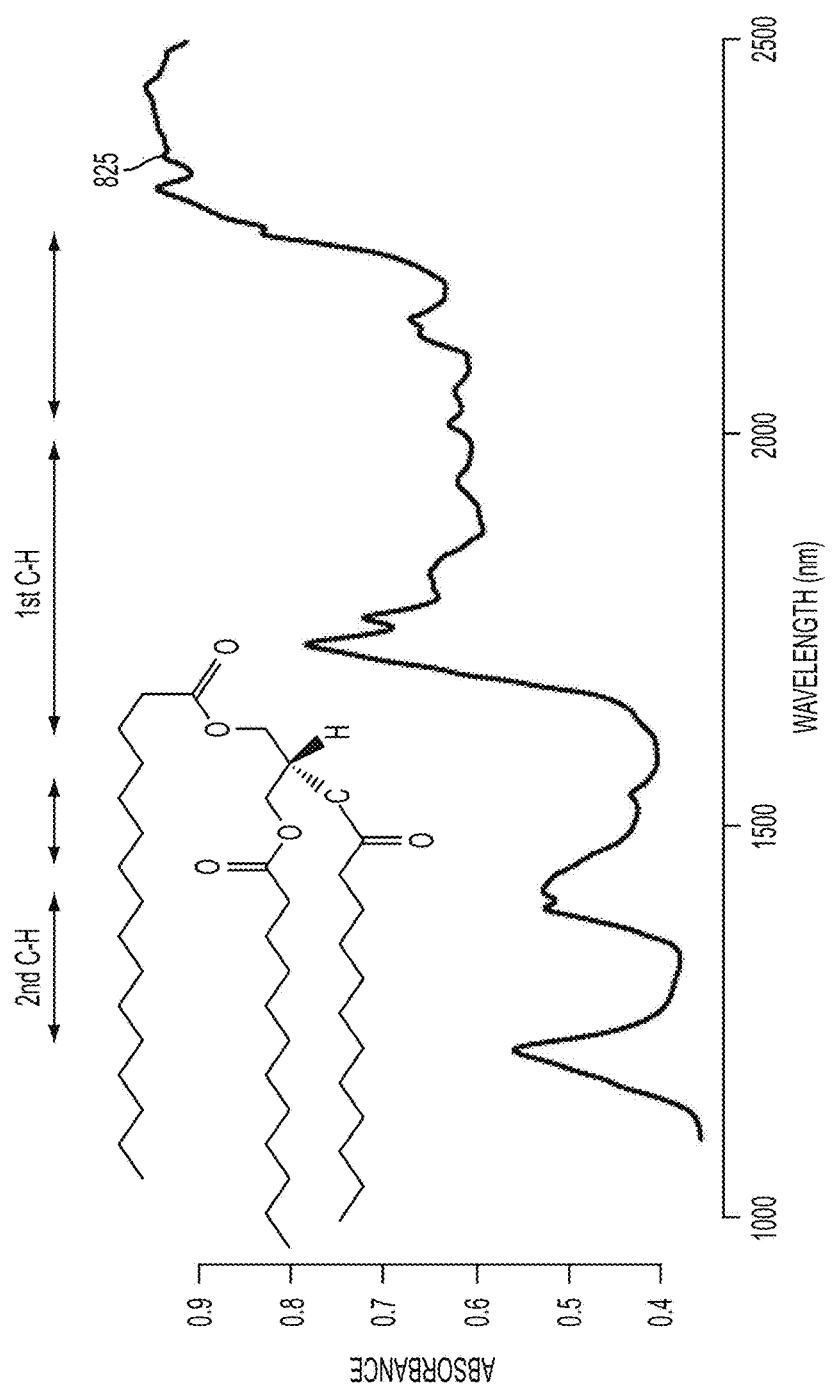
FIG. 8B illustrates the near infrared absorbance for triglyceride.

In yet another embodiment, the optical techniques described in this disclosure could also be used to measure levels of triglycerides. Triglycerides are bundles of fats that may be found in the blood stream, particularly after ingesting meals. The body manufactures triglycerides from carbohydrates and fatty foods that are eaten. In other words, triglycerides are the body's storage form of fat. Triglycerides are comprised of three fatty acids attached to a glycerol molecule, and measuring the level of triglycerides may be important for diabetics. The triglyceride levels or concentrations in blood may be rated as follows: desirable or normal may be less than 150 mg/dl; borderline high may be 150-199 mg/dl; high may be 200-499 mg/dl; and very high may be 500 mg/dl or greater. FIG. 8B illustrates one example of the near-infrared absorbance 825 for triglycerides. There are distinct absorbance peaks in the spectrum that should be measurable. The characteristic absorption bands may be assigned as follows: (a) the first overtones of C—H stretching vibrations (1600-1900 nm); (b) the region of second overtones of C—H stretching vibrations (1100-1250 nm); and, (c) two regions (2000-2200 nm and 1350-1500 nm) that comprise bands due to combinations of C—H stretching vibrations and other vibrational modes.

Figure 8C:
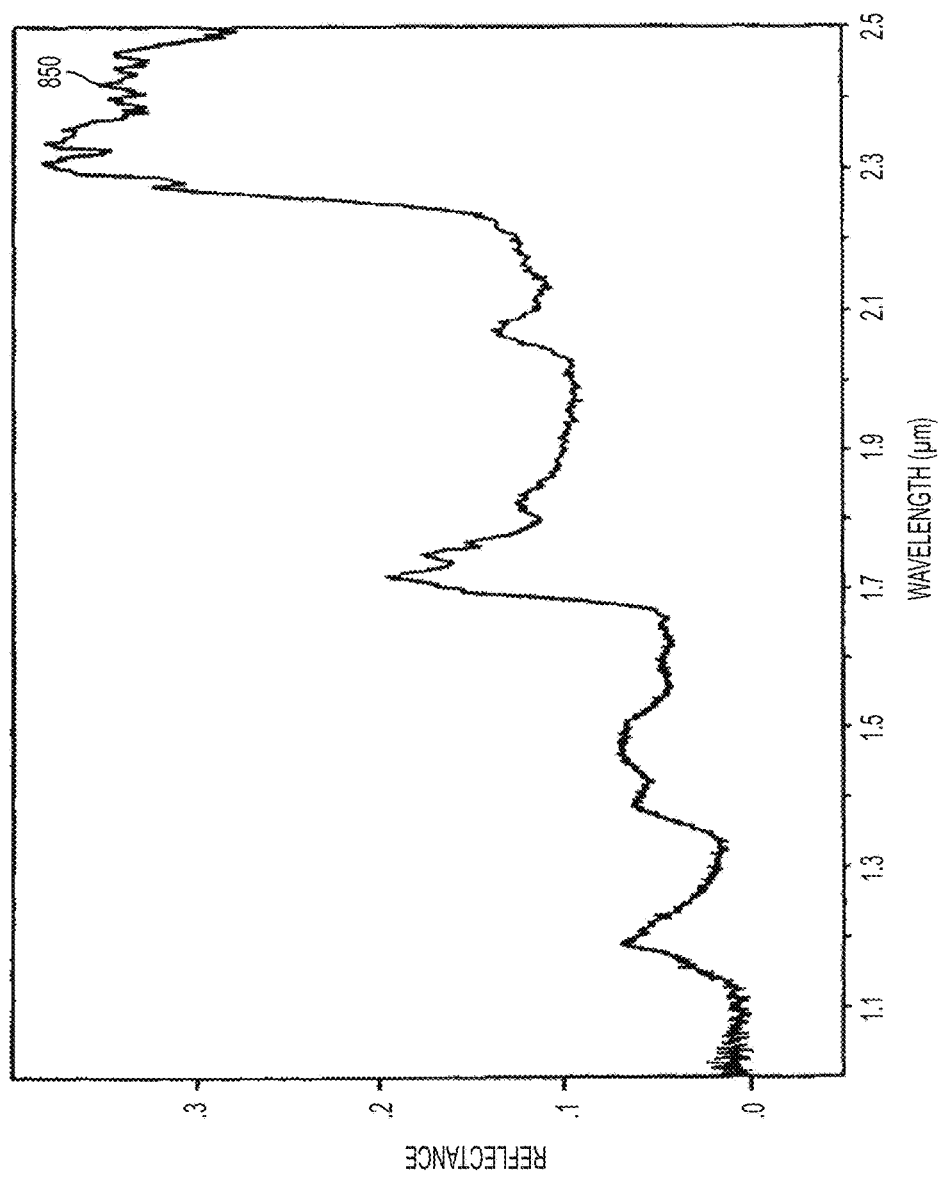
FIG. 8C shows the near-infrared reflectance spectrum for cholesterol.
Figure 8D:
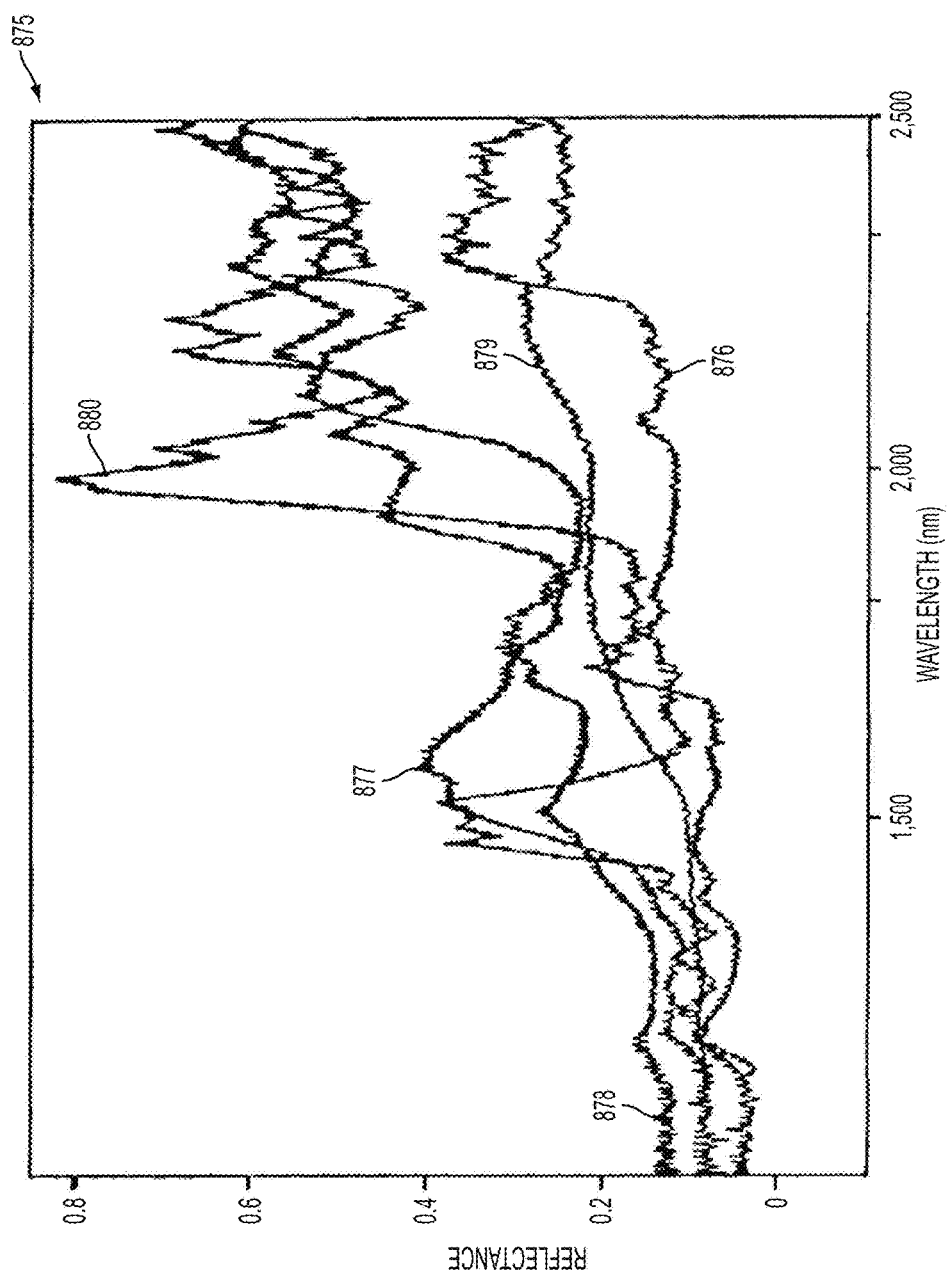
FIG. 8D illustrates the near-infrared reflectance versus wavelength for various blood constituents, including cholesterol, glucose, albumin, uric acid, and urea.

A further example of blood compositions that can be detected or measured using near-infrared light includes cholesterol monitoring. For example, FIG. 8C shows the near-infrared reflectance spectrum for cholesterol 850 with wavelength in microns (μm). Distinct absorption peaks are observable near 1210 nm (1.21 μm), 1720 nm (1.72 μm), and between 2300-2500 nm (2.3-2.5 μm). Also, there are other features near 1450 nm (1.45 μm) and 2050 nm (2.05 μm). In FIG. 8D the near-infrared reflectances 875 are displayed versus wavelength (nm) for various blood constituents. The spectrum for cholesterol 876 is overlaid with glucose 877, albumin 878, uric acid 879, and urea 880. As may be noted from FIG. 8D, at about 1720 nm and 2300 nm, cholesterol 876 reaches approximate reflectance peaks, while some of the other analytes are in a more gradual mode. Various signal processing methods may be used to identify and quantify the concentration of cholesterol 876 and/or glucose 877, or some of the other blood constituents.

As illustrated by FIGS. 5 and 7, one of the issues in measuring a particular blood constituent is the interfering and overlapping signal from other blood constituents. The selection of the constituent of interest may be improved using a number of techniques. For example, a higher light level or intensity may improve the signal-to-noise ratio for the measurement. Second, mathematical modeling and signal processing methodologies may help to reduce the interference, such as multivariate techniques, multiple linear regression, and factor-based algorithms, for example. For instance, a number of mathematical approaches include multiple linear regression, partial least squares, and principal component regression (PCR). Also, as illustrated in FIG. 8A, various mathematical derivatives, including the first and second derivatives, may help to accentuate differences between spectra. In addition, by using a wider wavelength range and using more sampling wavelengths may improve the ability to discriminate one signal from another. These are just examples of some of the methods of improving the ability to discriminate between different constituents, but other techniques may also be used and are intended to be covered by this disclosure.

In one embodiment, a SWIR camera or infrared camera system may be used to capture the images. The camera may include one or more lenses on the input, which may be adjustable. The focal plane assemblies may be made from mercury cadmium telluride material (HgCdTe), and the detectors may also include thermo-electric coolers. Alternately, the image sensors may be made from indium gallium arsenide (InGaAs), and CMOS transistors may be connected to each pixel of the InGaAs photodiode array. The camera may interface wirelessly or with a cable (e.g., USB, Ethernet cable, or fiber optics cable) to a computer or tablet or smart phone, where the images may be captured and processed. These are a few examples of infrared cameras, but other SWIR or infrared cameras may be used and are intended to be covered by this disclosure.

By use of an active illuminator, a number of advantages may be achieved. First, the variations due to sunlight and time-of-day may be factored out. The effects of the weather, such as clouds and rain, might also be reduced. Also, higher signal-to-noise ratios may be achieved. For example, one way to improve the signal-to-noise ratio would be to use modulation and lock-in techniques. In one embodiment, the light source may be modulated, and then the detection system would be synchronized with the light source. In a particular embodiment, the techniques from lock-in detection may be used, where narrow band filtering around the modulation frequency may be used to reject noise outside the modulation frequency. In an alternate embodiment, change detection schemes may be used, where the detection system captures the signal with the light source on and with the light source off. Again, for this system the light source may be modulated. Then, the signal with and without the light source is differenced. This may enable the sun light changes to be subtracted out. In addition, change detection may help to identify objects that change in the field of view. In the following some exemplary detection systems are described.

Interference from Skin

Several proposed non-invasive glucose monitoring techniques rely on transmission, absorption, and/or diffuse reflection through the skin to measure blood constituents or blood analytes in veins, arteries, capillaries or in the tissue itself. However, on top of the interference from other blood constituents or analytes, the skin also introduces significant interference. For example, chemical, structural, and physiological variations occur that may produce relatively large and nonlinear changes in the optical properties of the tissue sample. In one embodiment, the near-infrared reflectance or absorbance spectrum may be a complex combination of the tissue scattering properties that result from the concentration and characteristics of a multiplicity of tissue components including water, fat, protein, collagen, elastin, and/or glucose. Moreover, the optical properties of the skin may also change with environmental factors such as humidity, temperature and pressure. Physiological variation may also cause changes in the tissue measurement over time and may vary based on lifestyle, health, aging, etc. The structure and composition of skin may also vary widely among individuals, between different sites within an individual, and over time on the same individual. Thus, the skin introduces a dynamic interference signal that may have a wide variation due to a number of parameters.

Figure 9:
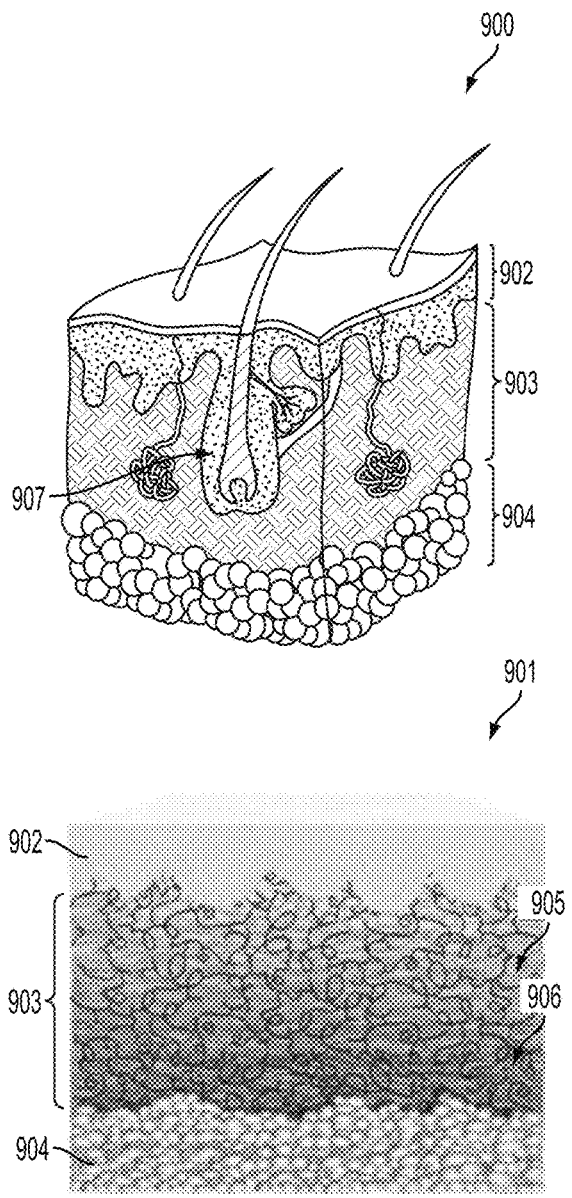
FIG. 9 shows a schematic of the human skin. In particular, the dermis may comprise significant amounts of collagen, elastin, lipids, and water.

FIG. 9 shows a schematic cross-section of human skin 900, 901. The top layer of the skin is epidermis 902, followed by a layer of dermis 903 and then subcutaneous fat 904 below the dermis. The epidermis 902, with a thickness of approximately 10-150 microns, may provide a barrier to infection and loss of moisture and other body constituents. The dermis 903 ranges in thickness from approximately 0.5 mm to 4 mm (averages approximately 1.2 mm over most of the body) and may provide the mechanical strength and elasticity of skin.

In the dermis 903, water may account for approximately 70% of the volume. The next most abundant constituent in the dermis 903 may be collagen 905, a fibrous protein comprising 70-75% of the dry weight of the dermis 903. Elastin fibers 906, also a protein, may also be plentiful in the dermis 903, although they constitute a smaller portion of the bulk. In addition, the dermis 903 may contain a variety of structures (e.g., sweat glands, hair follicles with adipose rich sebaceous glands 907 near their roots, and blood vessels) and other cellular constituents.

Below the dermis 903 lies the subcutaneous layer 904 comprising mostly adipose tissue. The subcutaneous layer 904 may be by volume approximately 10% water and may be comprised primarily of cells rich in triglycerides or fat. With this complicated structure of the skin 900, 901, the concentration of glucose may vary in each layer according to a variety of factors including the water content, the relative sizes of the fluid compartments, the distribution of capillaries, the perfusion of blood, the glucose uptake of cells, the concentration of glucose in blood, and the driving forces (e.g., osmotic pressure) behind diffusion.

Figure 10:
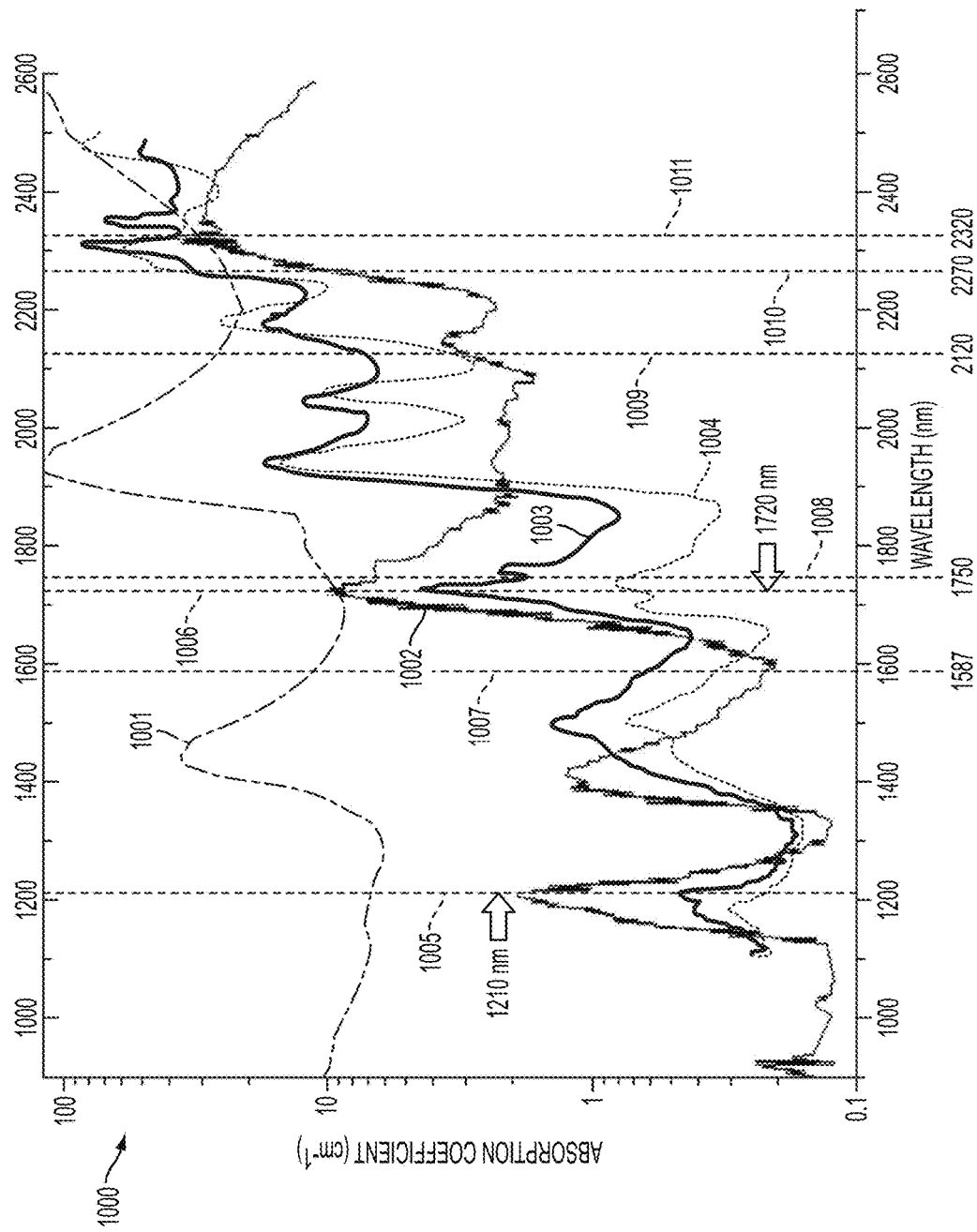
FIG. 10 illustrates the absorption coefficients for water (including scattering), adipose, collagen, and elastin.

To better understand the interference that the skin introduces when attempting to measure glucose, the absorption coefficient for the various skin constituents should be examined. For example, FIG. 10 illustrates 1000 the absorption coefficients for water (including scattering) 1001, adipose 1002, collagen 1003 and elastin 1004. Note that the absorption curves for water 1001 and adipose 1002 are calibrated, whereas the absorption curves for collagen 1003 and elastin 1004 are in arbitrary units. Also shown are vertical lines demarcating the wavelengths near 1210 nm 1005 and 1720 nm 1006. In general, the water absorption increases with increasing wavelength. With the increasing absorption beyond about 2000 nm, it may be difficult to achieve deeper penetration into biological tissue in the infrared wavelengths beyond approximately 2500 nm.

Although the absorption coefficient may be useful for determining the material in which light of a certain infrared wavelength will be absorbed, to determine the penetration depth of the light of a certain wavelength may also require the addition of scattering loss to the curves. For example, the water curve 1001 includes the scattering loss curve in addition to the water absorption. In particular, the scattering loss can be significantly higher at shorter wavelengths. In one embodiment, near the wavelength of 1720 nm (vertical line 1006 shown in FIG. 10), the adipose absorption 1002 can still be higher than the water plus scattering loss 1001. For tissue that contains adipose, collagen and elastin, such as the dermis of the skin, the total absorption can exceed the light energy lost to water absorption and light scattering at 1720 nm. On the other hand, at 1210 nm the adipose absorption 1002 can be considerably lower than the water plus scattering loss 1001, particularly since the scattering loss can be dominant at these shorter wavelengths.

The interference for glucose lines observed through skin may be illustrated by overlaying the glucose lines over the absorption curves 1000 for the skin constituents. For example, FIG. 2 illustrated that the glucose absorption 202 included features centered around 1587 nm, 1750 nm, 2120 nm, 2270 nm and 2320 nm. On FIG. 10 vertical lines have been drawn at the glucose line wavelengths of 1587 nm 1007, 1750 nm 1008, 2120 nm 1009, 2270 nm 1010 and 2320 nm 1011. In one embodiment, it may be difficult to detect the glucose lines near 1750 nm 1008, 2270 nm 1010 and 2320 nm 1011 due to significant spectral interference from other skin constituents. On the other hand, the glucose line near 1587 m 1007 may be more easily detected because it peaks while most of the other skin constituents are sloped downward toward an absorption valley. Moreover, the glucose line near 2120 nm 1009 may also be detectable for similar reasons, although adipose may have conflicting behavior due to local absorption minimum and maximum nearby in wavelength.

Thus, beyond the problem of other blood constituents or analytes having overlapping spectral features (e.g., FIG. 5), it may be difficult to observe glucose spectral signatures through the skin and its constituents of water, adipose, collagen and elastin. One approach to overcoming this difficulty may be to try to measure the blood constituents in veins that are located at relatively shallow distances below the skin. Veins may be more beneficial for the measurement than arteries, since arteries tend to be located at deeper levels below the skin. Also, in one embodiment it may be advantageous to use a differential measurement to subtract out some of the interfering absorption lines from the skin. For example, an instrument head may be designed to place one probe above a region of skin over a blood vein, while a second probe may be placed at a region of the skin without a noticeable blood vein below it. Then, by differencing the signals from the two probes, at least part of the skin interference may be cancelled out.

Figure 11:
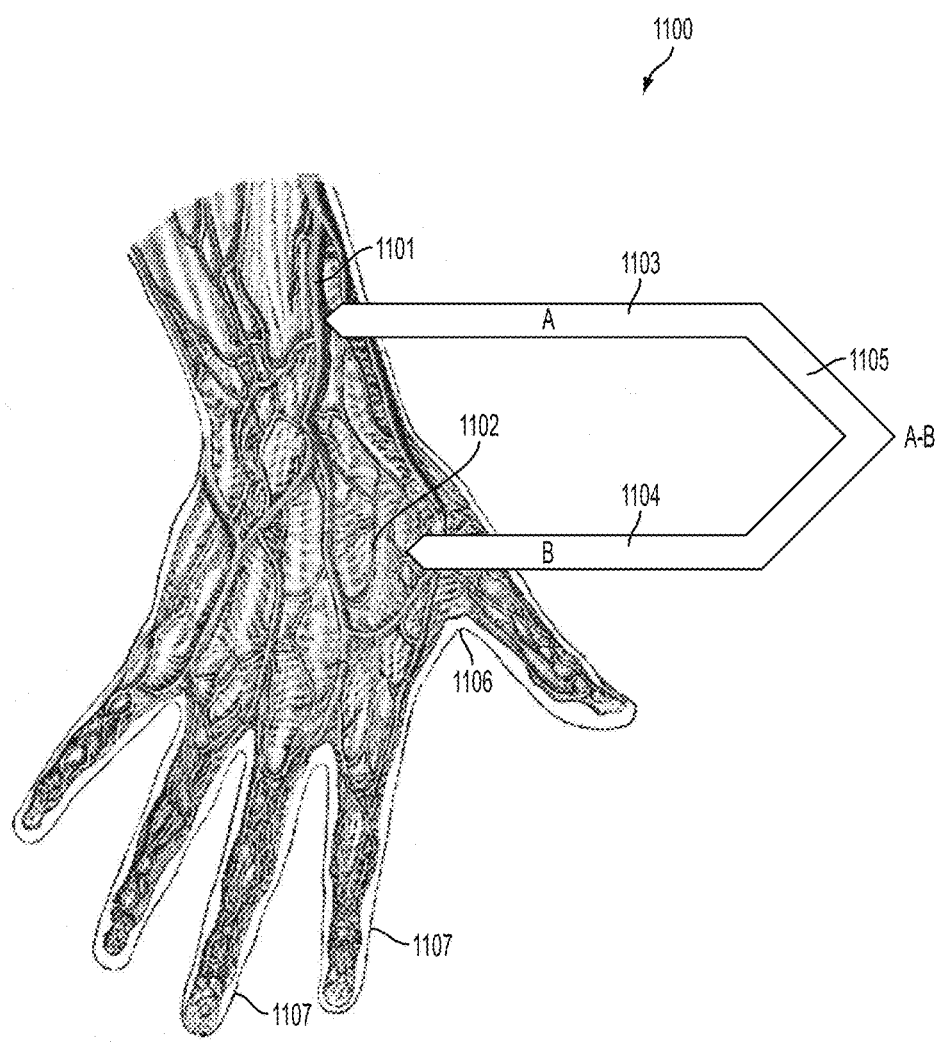
FIG. 11 shows the dorsal of the hand, where a differential measurement may be made to at least partially compensate for or subtract out the skin interference.
Figure 12:
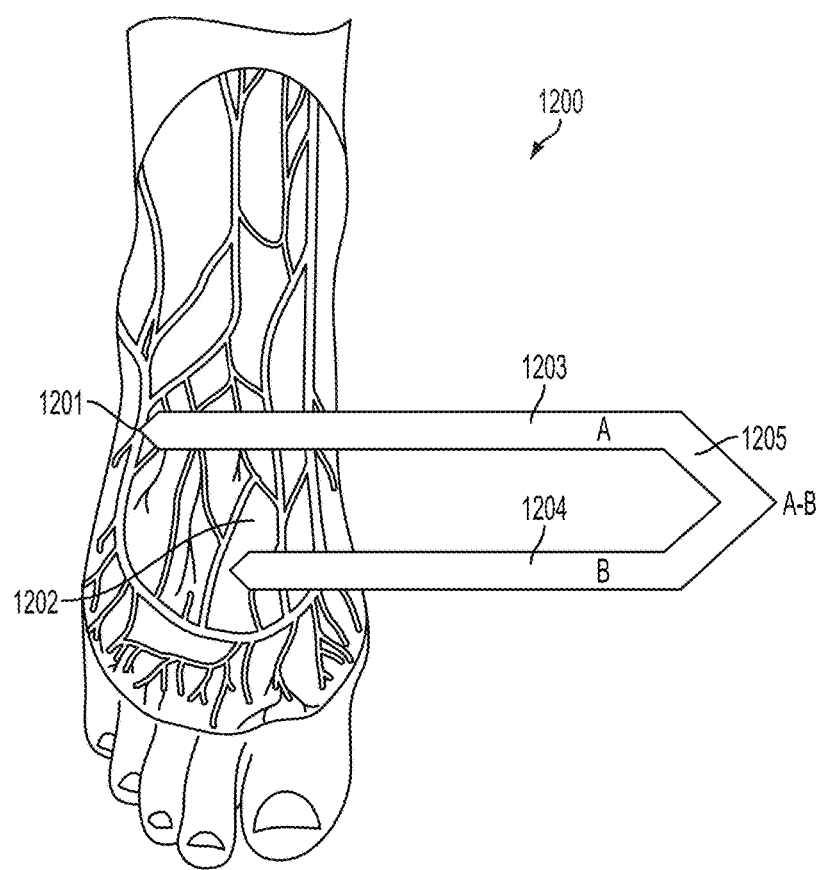
FIG. 12 shows the dorsal of the foot, where a differential measurement may be made to at least partially compensate for or subtract out the skin interference.

Two representative embodiments for performing such a differential measurement are illustrated in FIG. 11 and FIG. 12. In one embodiment shown in FIG. 11, the dorsal of the hand 1100 may be used for measuring blood constituents or analytes. The dorsal of the hand 1100 may have regions that have distinct veins 1101 as well as regions where the veins are not as shallow or pronounced 1102. By stretching the hand and leaning it backwards, the veins 1101 may be accentuated in some cases. A near-infrared diffuse reflectance measurement may be performed by placing one probe 1103 above the vein-rich region 1101. To turn this into a differential measurement, a second probe 1104 may be placed above a region without distinct veins 1102. Then, the outputs from the two probes may be subtracted 1105 to at least partially cancel out the features from the skin. The subtraction may be done preferably in the electrical domain, although it can also be performed in the optical domain or digitally/mathematically using sampled data based on the electrical and/or optical signals. Although one example of using the dorsal of the hand 1100 is shown, many other parts of the hand can be used within the scope of this disclosure. For example, alternate methods may use transmission through the webbing between the thumb and the fingers 1106, or transmission or diffuse reflection through the tips of the fingers 1107.

In another embodiment, the dorsal of the foot 1200 may be used instead of the hand. One advantage of such a configuration may be that for self-testing by a user, the foot may be easier to position the instrument using both hands. One probe 1203 may be placed over regions where there are more distinct veins 1201, and a near-infrared diffuse reflectance measurement may be made. For a differential measurement, a second probe 1204 may be placed over a region with less prominent veins 1202, and then the two probe signals may be subtracted, either electronically or optically, or may be digitized/sampled and processed mathematically depending on the particular application and implementation. As with the hand, the differential measurements may be intended to compensate for or subtract out (at least in part) the interference from the skin. Since two regions are used in close proximity on the same body part, this may also aid in removing some variability in the skin from environmental effects such as temperature, humidity, or pressure. In addition, it may be advantageous to first treat the skin before the measurement, by perhaps wiping with a cloth or treated cotton ball, applying some sort of cream, or placing an ice cube or chilled bag over the region of interest.

Although two embodiments have been described, many other locations on the body may be used using a single or differential probe within the scope of this disclosure. In yet another embodiment, the wrist may be advantageously used, particularly where a pulse rate is typically monitored. Since the pulse may be easily felt on the wrist, there is underlying the region a distinct blood flow. Other embodiments may use other parts of the body, such as the ear lobes, the tongue, the inner lip, the nails, the eye, or the teeth. Some of these embodiments will be further described below. The ear lobes or the tip of the tongue may be advantageous because they are thinner skin regions, thus permitting transmission rather than diffuse reflection. However, the interference from the skin is still a problem in these embodiments. Other regions such as the inner lip or the bottom of the tongue may be contemplated because distinct veins are observable, but still the interference from the skin may be problematic in these embodiments. The eye may seem as a viable alternative because it is more transparent than skin. However, there are still issues with scattering in the eye. For example, the anterior chamber of the eye (the space between the cornea and the iris) comprises a fluid known as aqueous humor. However, the glucose level in the eye chamber may have a significant temporal lag on changes in the glucose level compared to the blood glucose level.

In some instances, it may be desirable to create multiple locations of focused light. One way to accomplish this may be to slide the assemblies and/or the light source. In yet another embodiment shown in FIG. 13A, multiple collimated or focused light beams may be created in one assembly 1320. In this embodiment, optionally a surface cooling apparatus 1324 may be used, where a cooling fluid may be flowed either touching or in close proximity to the skin 1321. Also, in this particular embodiment a cylindrical assembly may optionally be used, where the cylindrical length may be several millimeters in length and defined by a clamp or mount 1323 placed on or near the leg. The light input 1327 may be received from a light source, which may use a fiber or fiber bundles to couple the light to the lens/mirror assembly 1326. A lens and/or mirror assembly 1326 may be used to couple the light input 1327 to the lenslet array or window 1325, either directly or indirectly. The lens and/or mirror assembly 1326 may also be coupled to the clamp or mount assembly 1323.

Figure 13A:
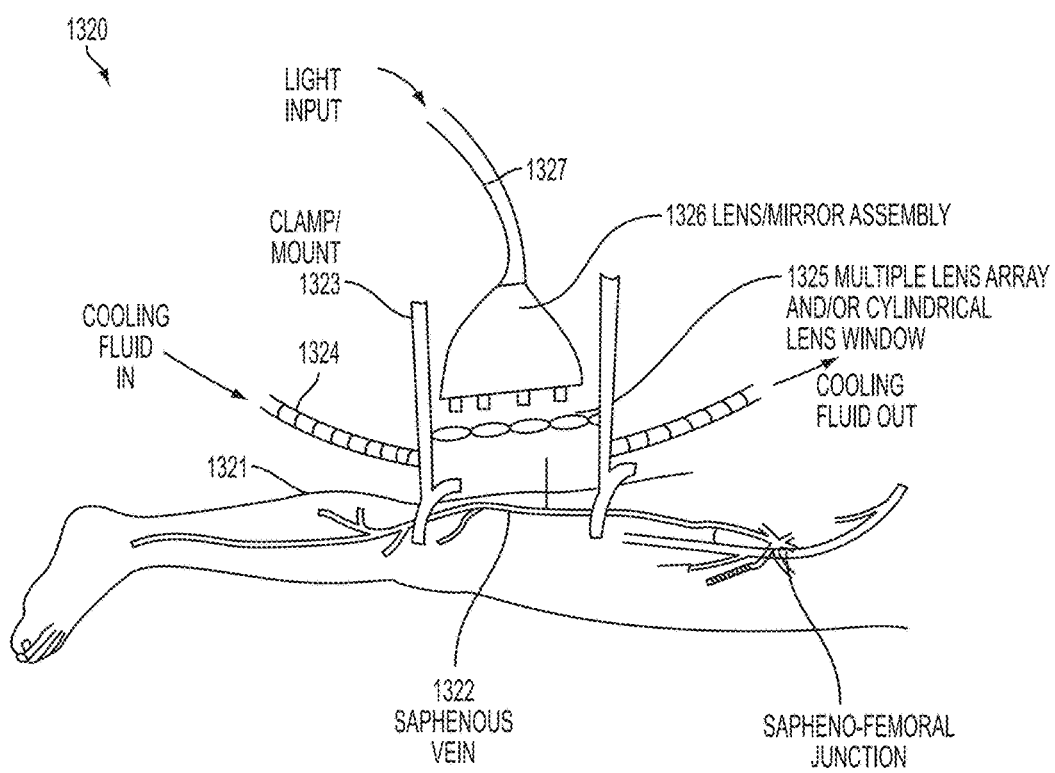
FIG. 13A shows an embodiment that may comprise multiple collimated or focused light beams.

In the embodiment of FIG. 13A, a window and/or lenslet array 1325 is also shown on the cylindrical surface for permitting the light to be incident on the skin 1321 and varicose vein 1322 at multiple spots. The lenslet array 1325 may comprise circular, spherical or cylindrical lenses, depending on the type of spots desired. As before, one advantage of placing the lenslet array 1325 in close proximity to the skin 1321 may be that a high NA lens may be used. Also, the input from the lens and/or mirror assembly to the lenslet array 1325 may be a single large beam, or a plurality of smaller beams. In one embodiment, a plurality of spots may be created by the lenslet array 1325. Although four spots are shown in FIG. 13A, any number of spots may be used and are intended to be covered by this disclosure.

Different combinations of these techniques may be employed, and other techniques may also be used and are intended to be covered by this disclosure. For example, in some instances only focused light may be used, in other instances only surface cooling or cryogenic sprays may be used, and in yet other embodiments a combination of the two may be used. Moreover, the clamps, mounts and holders are shown in simple design for illustrative purposes, but human factors engineering may be used to make these more user friendly or ergonomic design. These and other variations are also intended to be covered by this disclosure.

The lens and/or mirror assemblies may comprise one or more lenses, microscope objectives, curved or flat mirrors, lens tipped fibers, or some combination of these elements. As an example, the optics such as used in a camera may be employed in this arrangement, provided that the optics are substantially transparent at the light wavelengths being used. Moreover, reflections and losses through the optics may be reduced by applying anti-reflection coatings, and chromatic dispersion may be reduced by using reflective optics rather than refractive optics. Although a particular method of focusing the light has been described, other methods may also be used and are intended to be covered by this disclosure.

Figure 13B:
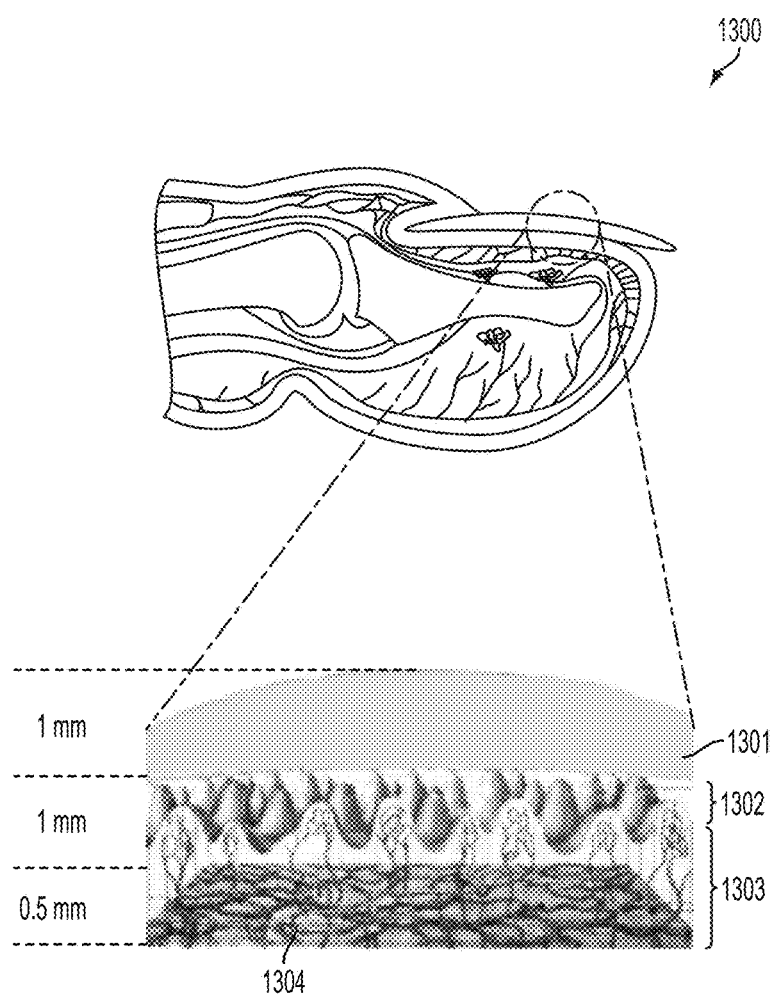
FIG. 13B illustrates a typical human nail tissue structure and the capillary vessels below it.

Because of the complexity of the interference from skin in non-invasive glucose monitoring (e.g., FIG. 10), other parts of the body without skin above blood vessels or capillaries may be alternative candidates for measuring blood constituents. One embodiment may involve transmission or reflection through human nails. As an example, FIG. 13B illustrates a typical human nail tissue structure 1300 and the capillary vessels below it. The fingernail 1301 is approximately 1 mm thick, and below this resides a layer of epidermis 1302 with a thickness of approximately 1 mm. The dermis 1304 is also shown, and within particularly the top about 0.5 mm of dermis are a significant number of capillary vessels. To measure the blood constituents, the light exposed on the top of the fingernail must penetrate about 2-2.5 mm or more, and the reflected light (round trip passage) should be sufficiently strong to measure. In one embodiment, the distance required to penetrate could be reduced by drilling a hole in the fingernail 1301.

Figure 14:
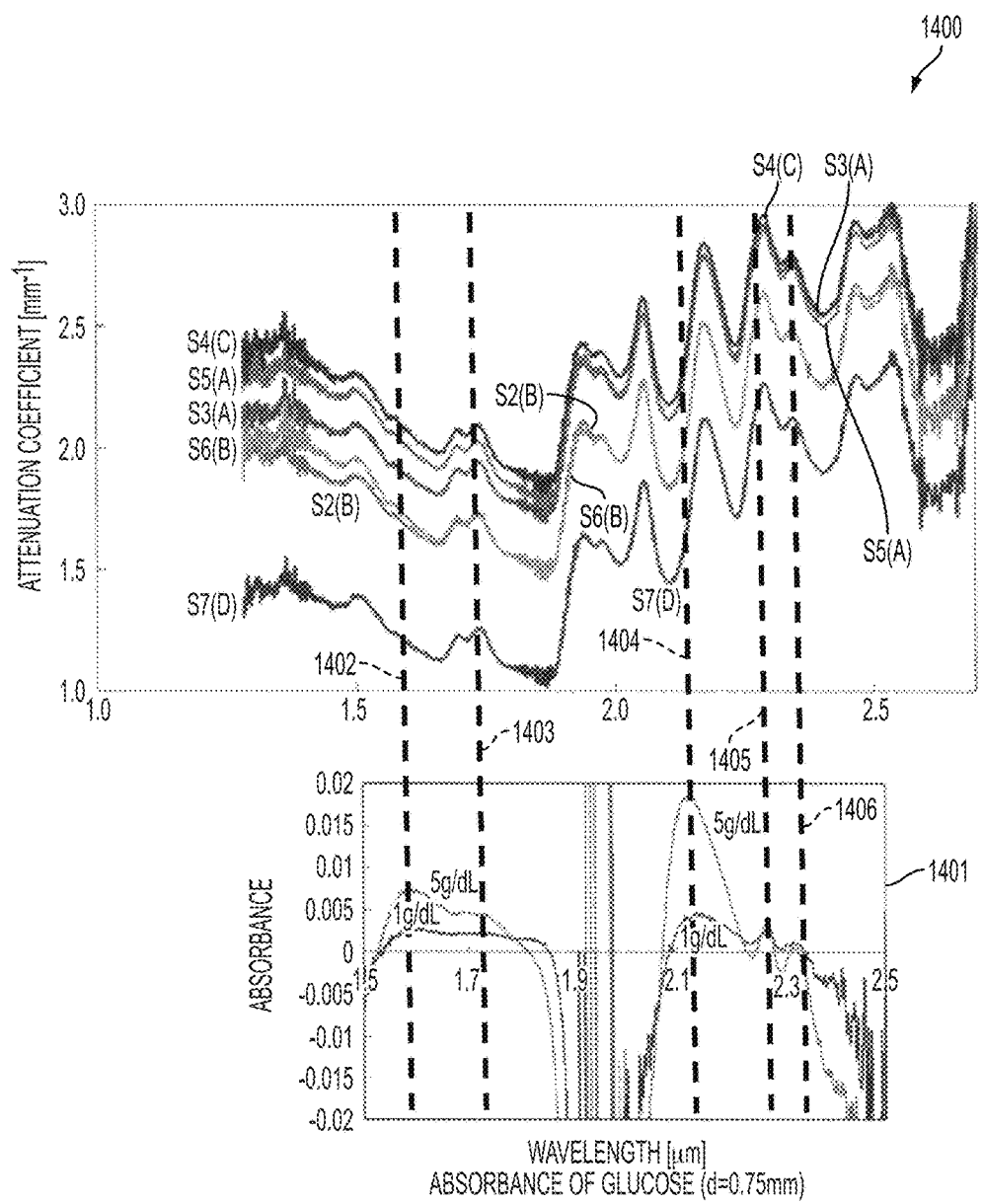
FIG. 14 shows the attenuation coefficient for seven nail samples that are allowed to stand in an environment with a humidity level of 14%. These coefficients are measured using an FTIR spectrometer over the near-infrared wavelength range of approximately 1 to 2.5 microns. Below is also included the spectrum of glucose.

In this alternative embodiment using the fingernail, there may still be interference from the nail's spectral features. For example, FIG. 14 illustrates the attenuation coefficient 1400 for seven nail samples that are allowed to stand in an environment with a humidity level of 14%. These coefficients are measured using an FTIR spectrometer over the near-infrared wavelength range of approximately 1 to 2.5 microns. These spectra are believed to correspond to the spectra of keratin contained in the nail plate. The base lines for the different samples are believed to differ because of the influence of scattering. Several of the absorption peaks observed correspond to peaks of keratin absorption, while other features may appear from the underlying epidermis and dermis. It should also be noted that the attenuation coefficients 1400 also vary considerably depending on humidity level or water content as well as temperature and other environmental factors. Moreover, the attenuation coefficient may also change in the presence of nail polish of various sorts.

Similar to skin, the large variations in attenuation coefficient for fingernails also may interfere with the absorption peaks of glucose. As an example, in FIG. 14 below the fingernail spectrum is also shown the glucose spectrum 1401 for two different glucose concentrations. The vertical lines 1402, 1403, 1404, 1405 and 1406 are drawn to illustrate the glucose absorption peaks and where they lie on the fingernail spectra 1400. As is apparent, the nail has interfering features that may be similar to skin, particularly since both have spectra that vary not only in wavelength but also with environmental factors. In one embodiment, it may be possible to see the glucose peaks 1402 and 1404 through the fingernail, but it may be much more difficult to observe the glucose peaks near 1403, 1405 and 1406.

Transmission or Reflection Through Teeth

Figure 15:
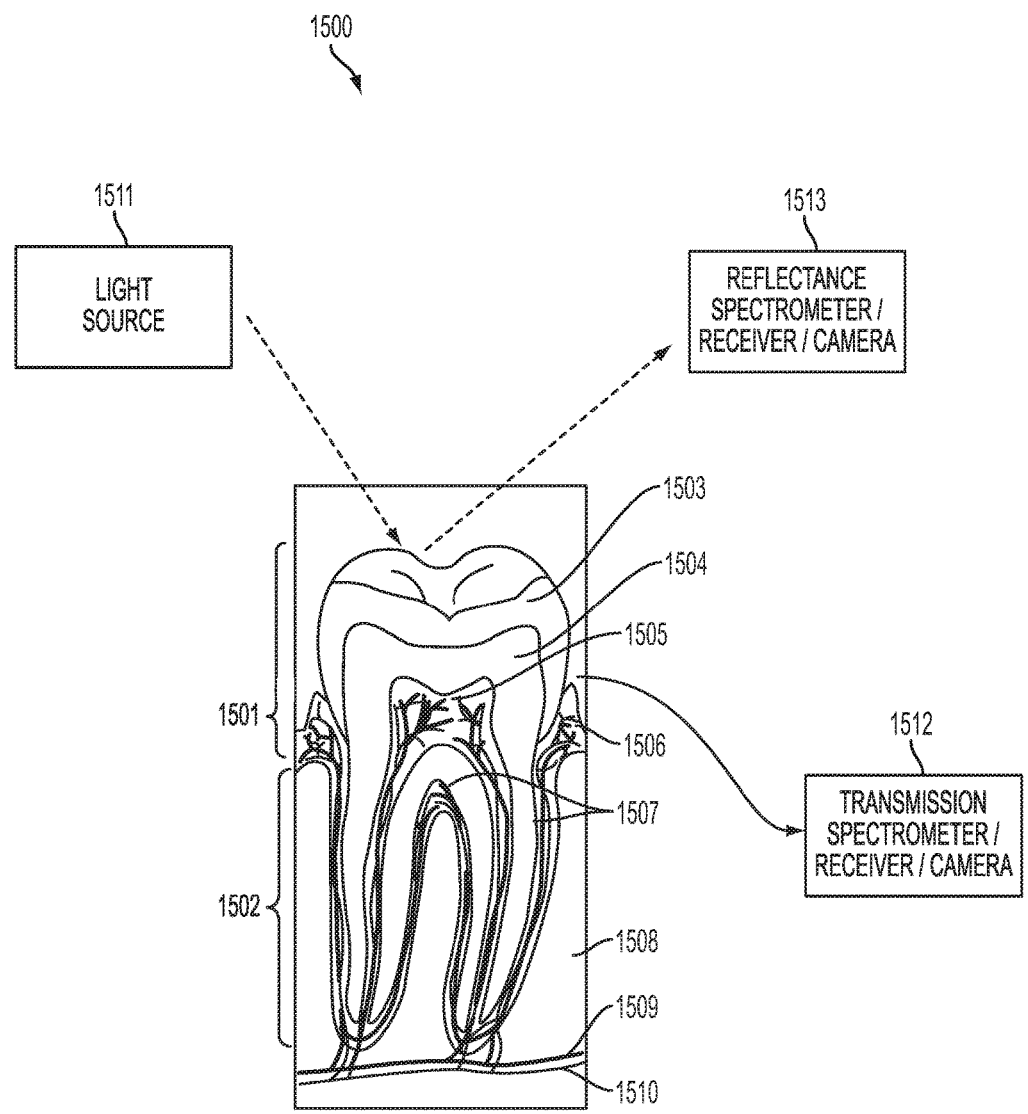
FIG. 15 illustrates the structure of a tooth.

Yet another embodiment may observe the transmittance or reflectance through teeth to measure blood constituents or analytes. FIG. 15 illustrates an exemplary structure of a tooth 1500. The tooth 1500 has a top layer called the crown 1501 and below that a root 1502 that reaches well into the gum 1506 and bone 1508 of the mouth. The exterior of the crown 1501 is an enamel layer 1503, and below the enamel is a layer of dentine 1504 that sits atop a layer of cementum 1507. Below the dentine 1504 is a pulp region 1505, which comprises within it blood vessels 1509 and nerves 1510. If the light can penetrate the enamel 1503 and dentine 1504, then the blood flow and blood constituents can be measured through the blood vessels in the dental pulp 1505. While it may be true that the amount of blood flow in the dental pulp 1505 may be less since it comprises capillaries, the smaller blood flow could still be advantageous if there is less interfering spectral features from the tooth.

Figure 16A:
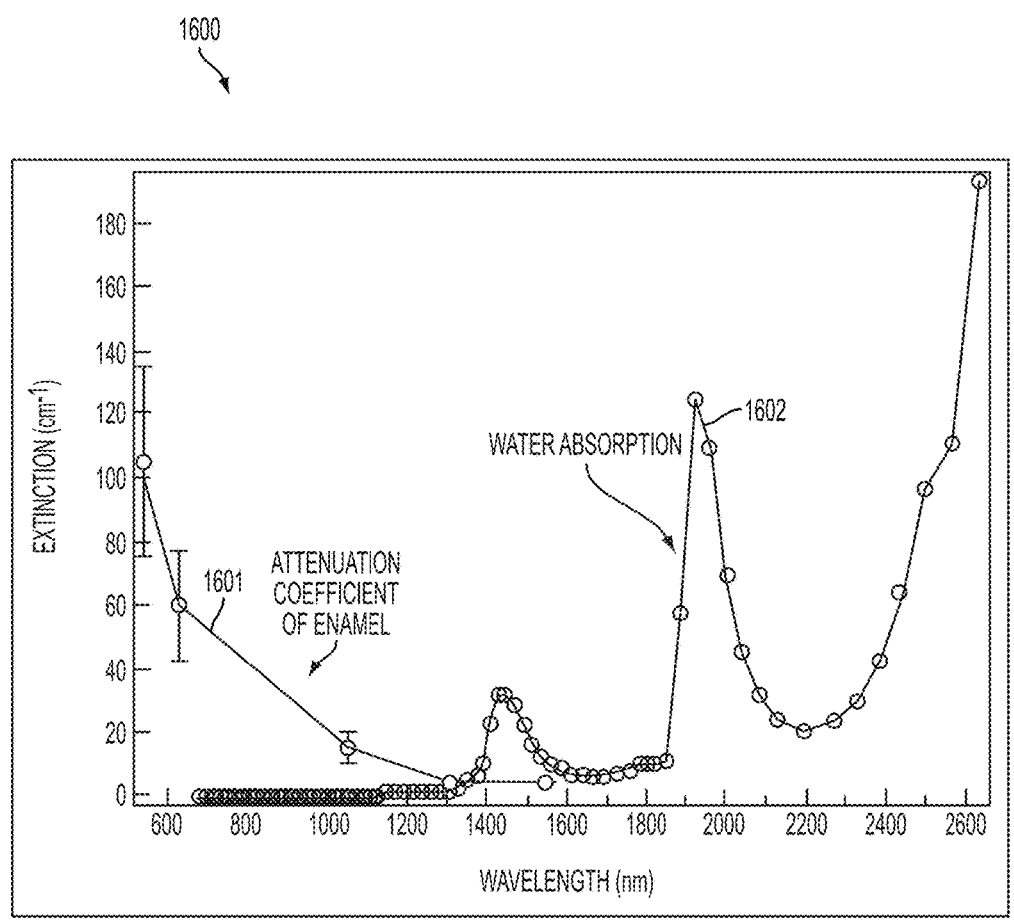
FIG. 16A shows the attenuation coefficient for dental enamel and water versus wavelength from approximately 600 nm to 2600 nm.

The transmission, absorption and reflection from teeth has been studied in the near infrared, and, although there are some features, the enamel and dentine appear to be fairly transparent in the near infrared (particularly wavelengths between 1500 and 2500 nm). For example, the absorption or extinction ratio for light transmission has been studied. FIG. 16A illustrates the attenuation coefficient 1600 for dental enamel 1601 (filled circles) and the absorption coefficient of water 1602 (open circles) versus wavelength. Near-infrared light may penetrate much further without scattering through all the tooth enamel, due to the reduced scattering coefficient in normal enamel. Scattering in enamel may be fairly strong in the visible, but decreases as approximately 1/wavelength$^3$ (i.e., inverse of the wavelength cubed) with increasing wavelength to a value of only 2-3 cm$^{-1}$ at 1310 nm and 1550 nm in the near infrared. Therefore, enamel may be virtually transparent in the near infrared with optical attenuation 1-2 orders of magnitude less than in the visible range.

Figure 16B:
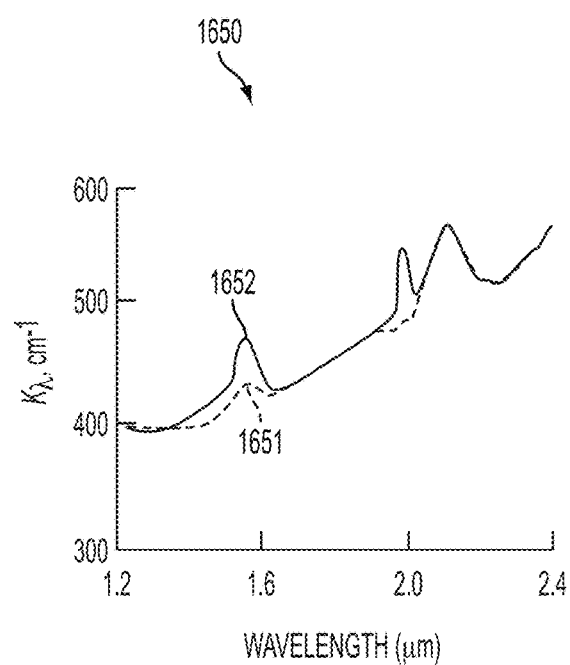
FIG. 16B illustrates the absorption spectrum of intact enamel and dentine in the wavelength range of approximately 1.2 to 2.4 microns.

As another example, FIG. 16B illustrates the absorption spectrum 1650 of intact enamel 1651 (dashed line) and dentine 1652 (solid line) in the wavelength range of approximately 1.2 to 2.4 microns. In the near infrared there are two absorption bands around 1.5 and 2 microns. The band with a peak around 1.57 microns may be attributed to the overtone of valent vibration of water present in both enamel and dentine. In this band, the absorption is greater for dentine than for enamel, which may be related to the large water content in this tissue. In the region of 2 microns, dentine may have two absorption bands, and enamel one. The band with a maximum near 2.1 microns may belong to the overtone of vibration of PO hydroxyapatite groups, which is the main substance of both enamel and dentine. Moreover, the band with a peak near 1.96 microns in dentine may correspond to water absorption (dentine may contain substantially higher water than enamel).

Figure 17:
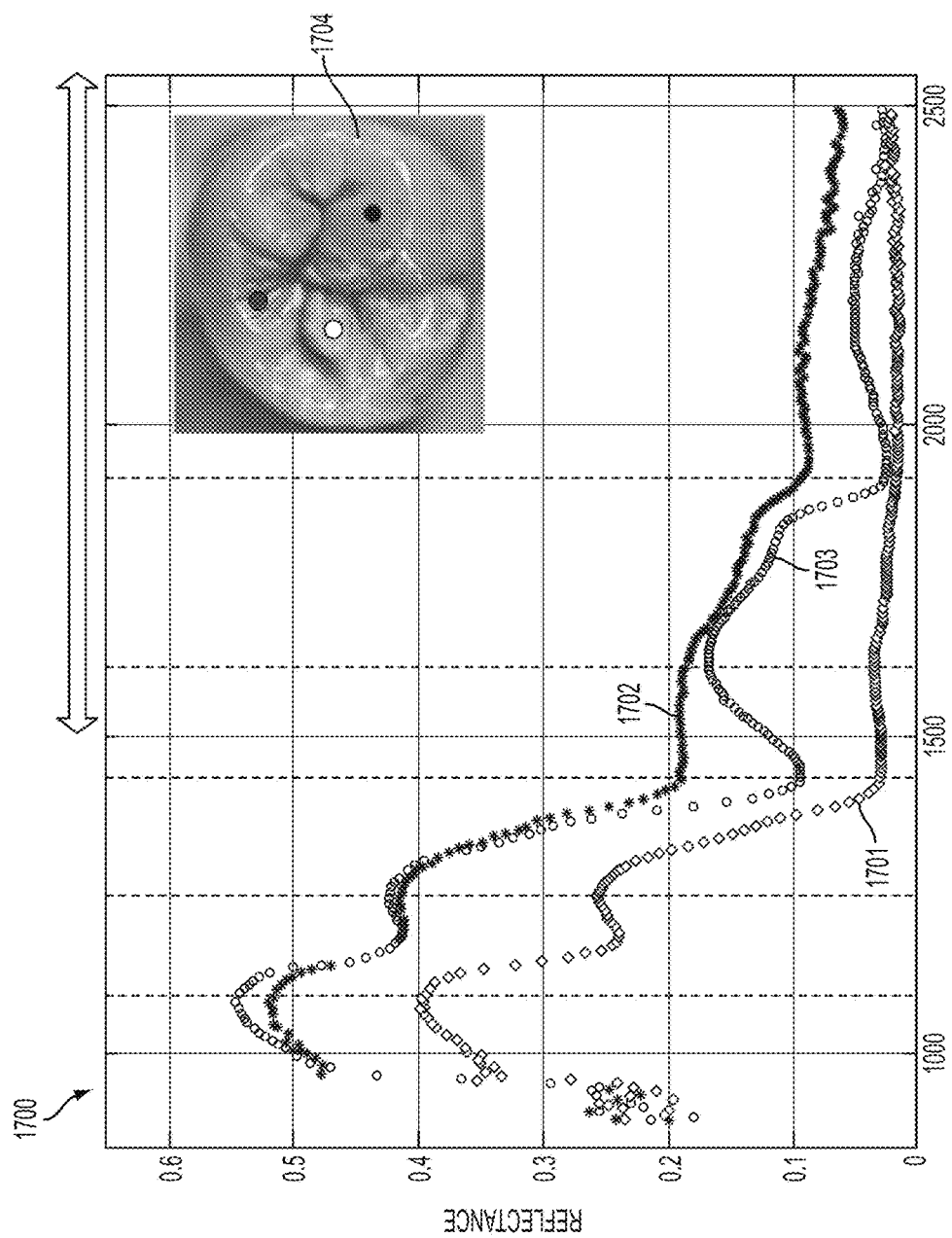
FIG. 17 shows the near infrared spectral reflectance over the wavelength range of approximately 800 nm to 2500 nm from an occlusal tooth surface. The black diamonds correspond to the reflectance from a sound, intact tooth section. The asterisks correspond to a tooth section with an enamel lesion. The circles correspond to a tooth section with a dentine lesion.

In addition to the absorption coefficient, the reflectance from intact teeth and teeth with dental caries (e.g., cavities) has been studied. In one embodiment, FIG. 17 shows the near infrared spectral reflectance 1700 over the wavelength range of approximately 800 nm to 2500 nm from an occlusal (e.g., top/bottom) tooth surface 1704. The curve with black diamonds 1701 corresponds to the reflectance from a sound, intact tooth section. The curve with asterisks * 1702 corresponds to a tooth section with an enamel lesion. The curve with circles 1703 corresponds to a tooth section with a dentine lesion. Thus, when there is a lesion, more scattering occurs and there may be an increase in the reflected light.

For wavelengths shorter than approximately 1400 nm, the shapes of the spectra remain similar, but the amplitude of the reflection changes with lesions. Between approximately 1400 nm and 2500 nm, an intact tooth 1701 has low reflectance (e.g., high transmission), and the reflectance appears to be more or less independent of wavelength. On the other hand, in the presence of lesions 1702 and 1703, there is increased scattering, and the scattering loss may be wavelength dependent. For example, the scattering loss may decrease as $1/(\text{wavelength})^3$—so, the scattering loss decreases with longer wavelengths. When there is a lesion in the dentine 1703, more water can accumulate in the area, so there is also increased water absorption. For example, the dips near 1450 nm and 1900 nm correspond to water absorption, and the reflectance dips are particularly pronounced in the dentine lesion 1703. One other benefit of the absorption, transmission or reflectance in the near infrared may be that stains and non-calcified plaque are not visible in this wavelength range, enabling better discrimination of defects, cracks, and demineralized areas.

Compared with the interference from skin 1000 in FIG. 10 or fingernails 1400 in FIG. 14, the teeth appear to introduce much less interference for non-invasive monitoring of blood constituents. The few features in FIG. 16B or 17 may be calibrated out of the measurement. Also, using an intact tooth 1701 may further minimize any interfering signals. Furthermore, since the tooth comprises relatively hard tissue, higher power from the light sources in the near infrared may be used without damaging the tissue, such as with skin.

Human Interface for Measurement System

A number of different types of measurements may be used to sample the blood in the dental pulp. The basic feature of the measurements should be that the optical properties are measured as a function of wavelength at a plurality of wavelengths. As further described below, the light source may output a plurality of wavelengths, or a continuous spectrum over a range of wavelengths. In a preferred embodiment, the light source may cover some or all of the wavelength range between approximately 1400 nm and 2500 nm. The signal may be received at a receiver, which may also comprise a spectrometer or filters to discriminate between different wavelengths. The signal may also be received at a camera, which may also comprise filters or a spectrometer. In an alternate embodiment, the spectral discrimination using filters or a spectrometer may be placed after the light source rather than at the receiver. The receiver usually comprises one or more detectors (optical-to-electrical conversion element) and electrical circuitry. The receiver may also be coupled to analog to digital converters, particularly if the signal is to be fed to a digital device.

Referring to FIG. 15, one or more light sources 1511 may be used for illumination. In one embodiment, a transmission measurement may be performed by directing the light source output 1511 to the region near the interface between the gum 1506 and dentine 1504. In one embodiment, the light may be directed using a light guide or a fiber optic. The light may then propagate through the dental pulp 1505 to the other side, where the light may be incident on one or more detectors or another light guide to transport the signal to a spectrometer, receiver or camera 1512. In another embodiment, the light source may be directed to one or more locations near the interface between the gum 1506 and dentine 1504 (in one example, could be from the two sides of the tooth). The transmitted light may then be detected in the occlusal surface above the tooth using a spectrometer, receiver, or camera 1512. In yet another embodiment, a reflectance measurement may be conducted by directing the light source output 1511 to, for example, the occlusal surface of the tooth, and then detecting the reflectance at a spectrometer, receiver or camera 1513. Although a few embodiments for measuring the blood constituents through a tooth are described, other embodiments and techniques may also be used and are intended to be covered by this disclosure.

Figure 18A:
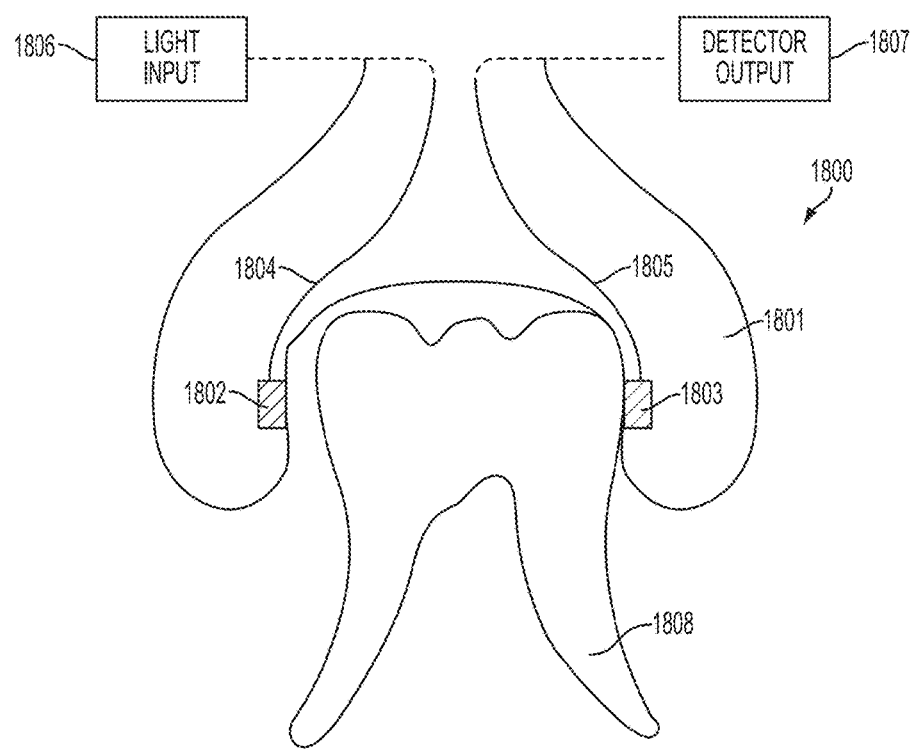
FIG. 18A illustrates a clamp design of a human interface to cap over one or more teeth and perform a non-invasive measurement of blood constituents.

The human interface for the non-invasive measurement of blood constituents may be of various forms. In one embodiment, a "clamp" design 1800 may be used cap over one or more teeth, as illustrated in FIG. 18A. The clamp design may be different for different types of teeth, or it may be flexible enough to fit over different types of teeth. For example, different types of teeth include the molars (toward the back of the mouth), the premolars, the canine, and the incisors (toward the front of the mouth). One embodiment of the clamp-type design is illustrated in FIG. 18A for a molar tooth 1808. The C-clamp 1801 may be made of a plastic or rubber material, and it may comprise a light source input 1802 and a detector output 1803 on the front or back of the tooth.

The light source input 1802 may comprise a light source directly, or it may have light guided to it from an external light source. Also, the light source input 1802 may comprise a lens system to collimate or focus the light across the tooth. The detector output 1803 may comprise a detector directly, or it may have a light guide to transport the signal to an external detector element. The light source input 1802 may be coupled electrically or optically through 1804 to a light input 1806. For example, if the light source is external in 1806, then the coupling element 1804 may be a light guide, such as a fiber optic. Alternately, if the light source is contained in 1802, then the coupling element 1804 may be electrical wires connecting to a power supply in 1806. Similarly, the detector output 1803 may be coupled to a detector output unit 1807 with a coupling element 1805, which may be one or more electrical wires or a light guide, such as a fiber optic. This is just one example of a clamp over one or more teeth, but other embodiments may also be used and are intended to be covered by this disclosure.

Figure 18B:
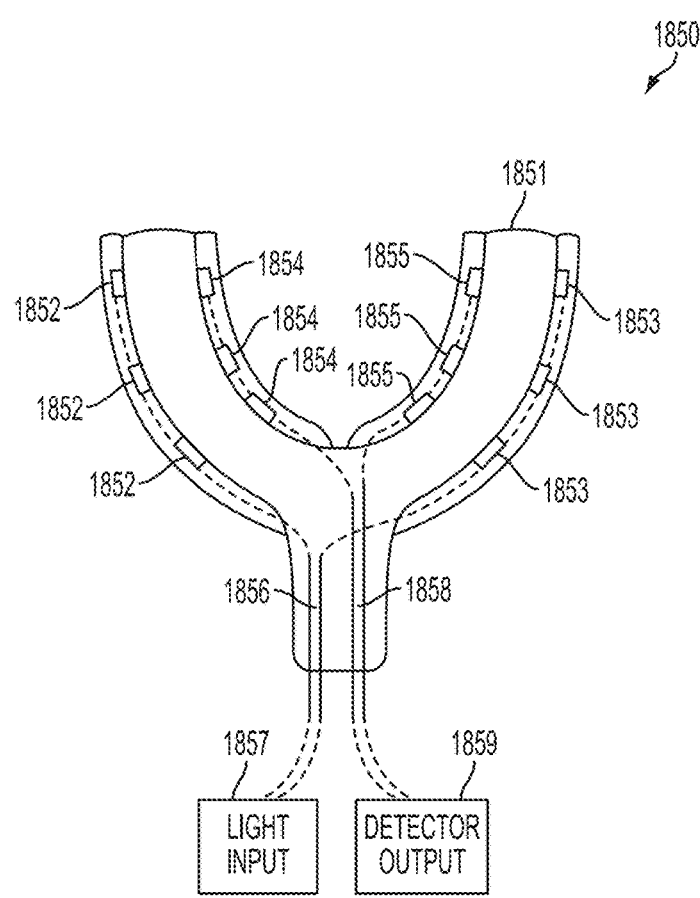
FIG. 18B shows a mouth guard design of a human interface to perform a non-invasive measurement of blood constituents.

In yet another embodiment, one or more light source ports and sensor ports may be used in a mouth-guard type design. For example, one embodiment of a dental mouth guard 1850 is illustrated in FIG. 18B. The structure of the mouth guard 1851 may be similar to mouth guards used in sports (e.g., when playing football or boxing) or in dental trays used for applying fluoride treatment, and the mouth guard may be made from plastic or rubber materials, for example. As an example, the mouth guard may have one or more light source input ports 1852, 1853 and one or more detector output ports 1854, 1855. Although six input and output ports are illustrated, any number of ports may be used.

Similar to the clamp design described above, the light source inputs 1852, 1853 may comprise one or more light sources directly, or they may have light guided to them from an external light source. Also, the light source inputs 1852, 1853 may comprise lens systems to collimate or focus the light across the teeth. The detector outputs 1854, 1855 may comprise one or more detectors directly, or they may have one or more light guides to transport the signals to an external detector element. The light source inputs 1852, 1853 may be coupled electrically or optically through 1856 to a light input 1857. For example, if the light source is external in 1857, then the one or more coupling elements 1856 may be one or more light guides, such as a fiber optic. Alternately, if the light sources are contained in 1852, 1853, then the coupling element 1856 may be one or more electrical wires connecting to a power supply in 1857. Similarly, the detector outputs 1854, 1855 may be coupled to a detector output unit 1859 with one or more coupling elements 1858, which may be one or more electrical wires or one or more light guides, such as a fiber optic. This is just one example of a mouth guard design covering a plurality of teeth, but other embodiments may also be used and are intended to be covered by this disclosure. For instance, the position of the light source inputs and detector output ports could be exchanged, or some mixture of locations of light source inputs and detector output ports could be used.

Also, if reflectance from the teeth is to be measured, then the light sources and detectors may be on the same side of the tooth. Moreover, it may be advantageous to pulse the light source with a particular pulse width and pulse repetition rate, and then the detection system can measure the pulsed light returned from or transmitted through the tooth. Using a lock-in type technique (e.g., detecting at the same frequency as the pulsed light source and also possibly phase locked to the same signal), the detection system may be able to reject background or spurious signals and increase the signal-to-noise ratio of the measurement.

Other elements may be added to the human interface designs of FIG. 18 and are also intended to be covered by this disclosure. For instance, in one embodiment it may be desirable to have replaceable inserts that may be disposable. Particularly in a doctor's office or hospital setting, the same instrument may be used with a plurality of patients. Rather than disinfecting the human interface after each use, it may be preferable to have disposable inserts that can be thrown away after each use. In one embodiment, a thin plastic coating material may enclose the clamp design of FIG. 18A or mouth guard design of FIG. 18B. The coating material may be inserted before each use, and then after the measurement is exercised the coating material may be peeled off and replaced. Such a design may save the physician or user considerable time, while at the same time provide the business venture with a recurring cost revenue source. Any coating material or other disposable device may be constructed of a material having suitable optical properties that may be considered during processing of the signals used to detect any anomalies in the teeth.

Light Sources for Near Infrared

In general, the near-infrared (NIR) region of the electromagnetic spectrum covers between approximately 0.7 microns (700 nm) to about 2.5 microns (2500 nm). However, it may also be advantageous to use just the short-wave infrared between approximately 1.4 microns (1400 nm) and about 2.5 microns (2500 nm). One reason for preferring the SWIR over the entire NIR may be to operate in the so-called "eye-safe" window, which corresponds to wavelengths longer than about 1400 nm. While the SWIR is used for illustrative purposes, it should be clear that the discussion that follows could also apply to using the NIR wavelength range, or other wavelength bands. There are a number of light sources that may be used in the near infrared. To be more specific, the discussion below will consider light sources operating in the so-called short wave infrared (SWIR), which may cover the wavelength range of approximately 1400 nm to 2500 nm. Other wavelength ranges may also be used for the applications described in this disclosure, so the discussion below is merely provided for exemplary types of light sources. The SWIR wavelength range may be valuable for a number of reasons. First, the SWIR corresponds to a transmission window through water and the atmosphere. For example, 302 in FIG. 3A and 1602 in FIG. 16A illustrate the water transmission windows. Also, through the atmosphere, wavelengths in the SWIR have similar transmission windows due to water vapor in the atmosphere. Second, the so-called "eye-safe" wavelengths are wavelengths longer than approximately 1400 nm. Third, the SWIR covers the wavelength range for nonlinear combinations of stretching and bending modes as well as the first overtone of C—H stretching modes. Thus, for example, glucose and ketones among other substances may have unique signatures in the SWIR. Moreover, many solids have distinct spectral signatures in the SWIR, so particular solids may be identified using stand-off detection or remote sensing. For instance, many explosives have unique signatures in the SWIR.

Different light sources may be selected for the SWIR based on the needs of the application. Some of the features for selecting a particular light source include power or intensity, wavelength range or bandwidth, spatial or temporal coherence, spatial beam quality for focusing or transmission over long distance, and pulse width or pulse repetition rate. Depending on the application, lamps, light emitting diodes (LEDs), laser diodes (LD's), tunable LD's, super-luminescent laser diodes (SLDs), fiber lasers or super-continuum sources (SC) may be advantageously used. Also, different fibers may be used for transporting the light, such as fused silica fibers, plastic fibers, mid-infrared fibers (e.g., tellurite, chalcogenides, fluorides, ZBLAN, etc), or a hybrid of these fibers.

Lamps may be used if low power or intensity of light is required in the SWIR, and if an incoherent beam is suitable. In one embodiment, in the SWIR an incandescent lamp that can be used is based on tungsten and halogen, which have an emission wavelength between approximately 500 nm to 2500 nm. For low intensity applications, it may also be possible to use thermal sources, where the SWIR radiation is based on the black body radiation from the hot object. Although the thermal and lamp based sources are broadband and have low intensity fluctuations, it may be difficult to achieve a high signal-to-noise ratio in a non-invasive blood constituent measurement due to the low power levels. Also, the lamp based sources tend to be energy inefficient.

In another embodiment, LED's can be used that have a higher power level in the SWIR wavelength range. LED's also produce an incoherent beam, but the power level can be higher than a lamp and with higher energy efficiency. Also, the LED output may more easily be modulated, and the LED provides the option of continuous wave or pulsed mode of operation. LED's are solid state components that emit a wavelength band that is of moderate width, typically between about 20 nm to 40 nm. There are also so-called super-luminescent LEDs that may even emit over a much wider wavelength range. In another embodiment, a wide band light source may be constructed by combining different LEDs that emit in different wavelength bands, some of which could preferably overlap in spectrum. One advantage of LEDs as well as other solid state components is the compact size that they may be packaged into.

In yet another embodiment, various types of laser diodes may be used in the SWIR wavelength range. Just as LEDs may be higher in power but narrower in wavelength emission than lamps and thermal sources, the LDs may be yet higher in power but yet narrower in wavelength emission than LEDs. Different kinds of LDs may be used, including Fabry-Perot LDs, distributed feedback (DFB) LDs, distributed Bragg reflector (DBR) LDs. Since the LDs have relatively narrow wavelength range (typically under 10 nm), in one embodiment a plurality of LDs may be used that are at different wavelengths in the SWIR. For example, in a preferred embodiment for non-invasive glucose monitoring, it may be advantageous to use LDs having emission spectra near some or all of the glucose spectral peaks (e.g., near 1587 nm, 1750 nm, 2120 nm, 2270 nm, and 2320 nm). The various LDs may be spatially multiplexed, polarization multiplexed, wavelength multiplexed, or a combination of these multiplexing methods. Also, the LDs may be fiber pig-tailed or have one or more lenses on the output to collimate or focus the light. Another advantage of LDs is that they may be packaged compactly and may have a spatially coherent beam output. Moreover, tunable LDs that can tune over a range of wavelengths are also available. The tuning may be done by varying the temperature, or electrical current may be used in particular structures, such as distributed Bragg reflector LDs. In another embodiment, external cavity LDs may be used that have a tuning element, such as a fiber grating or a bulk grating, in the external cavity.

In another embodiment, super-luminescent laser diodes may provide higher power as well as broad bandwidth. An SLD is typically an edge emitting semiconductor light source based on super-luminescence (e.g., this could be amplified spontaneous emission). SLDs combine the higher power and brightness of LDs with the low coherence of conventional LEDs, and the emission band for SLD's may be 5 to 100 nm wide, preferably in the 60 to 100 nm range. Although currently SLDs are commercially available in the wavelength range of approximately 400 nm to 1700 nm, SLDs could and may in the future be made to cover a broader region of the SWIR.

Figure 19:
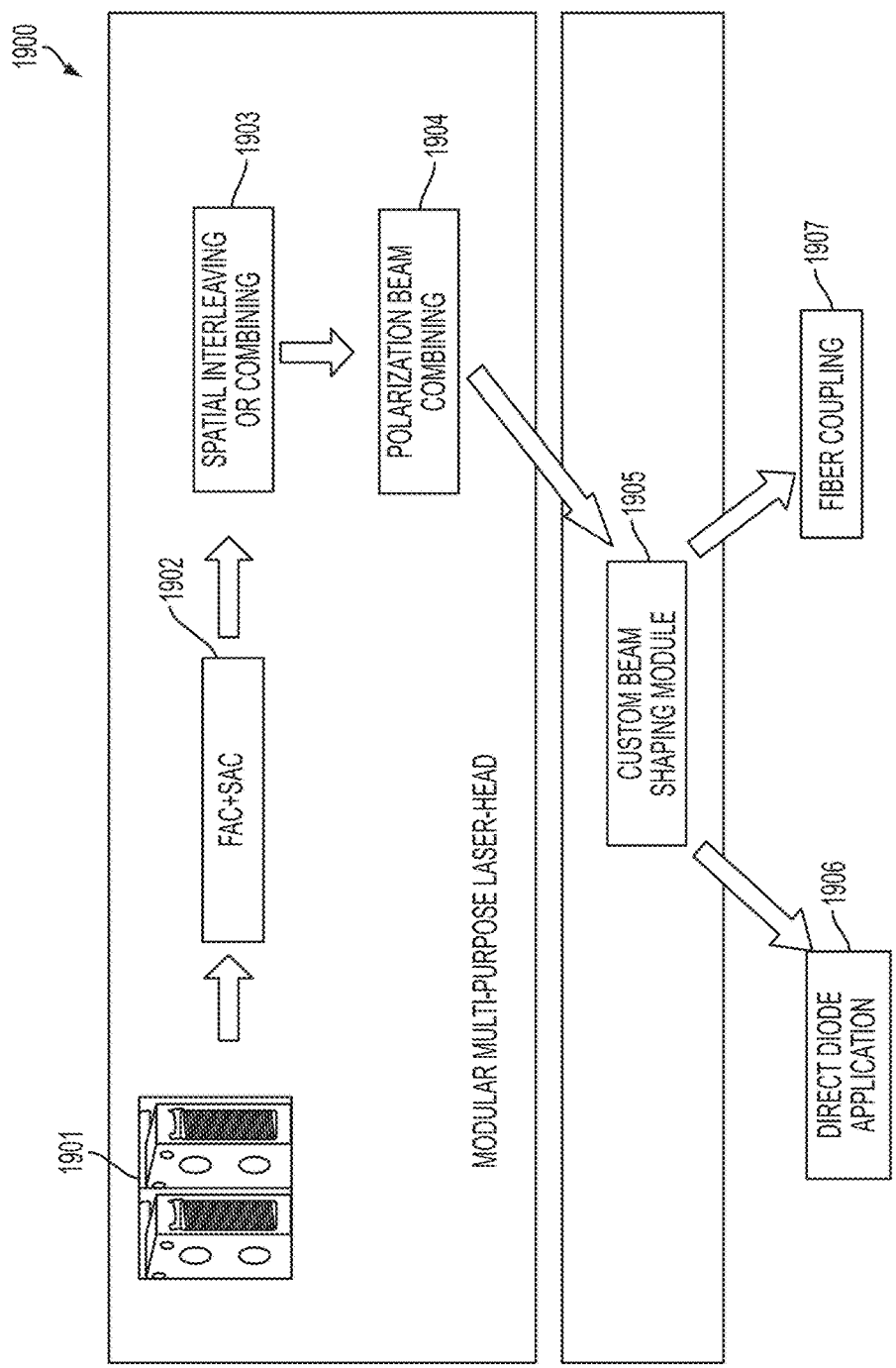
FIG. 19 illustrates a block diagram or building blocks for constructing high power laser diode assemblies.

In yet another embodiment, high power LDs for either direct excitation or to pump fiber lasers and SC light sources may be constructed using one or more laser diode bar stacks. As an example, FIG. 19 shows an example of the block diagram 1900 or building blocks for constructing the high power LDs. In this embodiment, one or more diode bar stacks 1901 may be used, where the diode bar stack may be an array of several single emitter LDs. Since the fast axis (e.g., vertical direction) may be nearly diffraction limited while the slow-axis (e.g., horizontal axis) may be far from diffraction limited, different collimators 1902 may be used for the two axes.

Then, the brightness may be increased by spatially combining the beams from multiple stacks 1903. The combiner may include spatial interleaving, it may include wavelength multiplexing, or it may involve a combination of the two. Different spatial interleaving schemes may be used, such as using an array of prisms or mirrors with spacers to bend one array of beams into the beam path of the other. In another embodiment, segmented mirrors with alternate high-reflection and anti-reflection coatings may be used. Moreover, the brightness may be increased by polarization beam combining 1904 the two orthogonal polarizations, such as by using a polarization beam splitter. In one embodiment, the output may then be focused or coupled into a large diameter core fiber. As an example, typical dimensions for the large diameter core fiber range from approximately 100 microns in diameter to 400 microns or more. Alternatively or in addition, a custom beam shaping module 1905 may be used, depending on the particular application. For example, the output of the high power LD may be used directly 1906, or it may be fiber coupled 1907 to combine, integrate, or transport the high power LD energy. These high power LDs may grow in importance because the LD powers can rapidly scale up. For example, instead of the power being limited by the power available from a single emitter, the power may increase in multiples depending on the number of diodes multiplexed and the size of the large diameter fiber. Although FIG. 19 is shown as one embodiment, some or all of the elements may be used in a high power LD, or additional elements may also be used.

SWIR Super-Continuum Lasers

Each of the light sources described above have particular strengths, but they also may have limitations. For example, there is typically a trade-off between wavelength range and power output. Also, sources such as lamps, thermal sources, and LEDs produce incoherent beams that may be difficult to focus to a small area and may have difficulty propagating for long distances. An alternative source that may overcome some of these limitations is an SC light source. Some of the advantages of the SC source may include high power and intensity, wide bandwidth, spatially coherent beam that can propagate nearly transform limited over long distances, and easy compatibility with fiber delivery.

Supercontinuum lasers may combine the broadband attributes of lamps with the spatial coherence and high brightness of lasers. By exploiting a modulational instability initiated supercontinuum (SC) mechanism, an all-fiber-integrated SC laser with no moving parts may be built using commercial-off-the-shelf (COTS) components. Moreover, the fiber laser architecture may be a platform where SC in the visible, near-infrared/SWIR, or mid-IR can be generated by appropriate selection of the amplifier technology and the SC generation fiber. But until now, SC lasers were used primarily in laboratory settings since typically large, table-top, mode-locked lasers were used to pump nonlinear media such as optical fibers to generate SC light. However, those large pump lasers may now be replaced with diode lasers and fiber amplifiers that gained maturity in the telecommunications industry.

Figure 20:
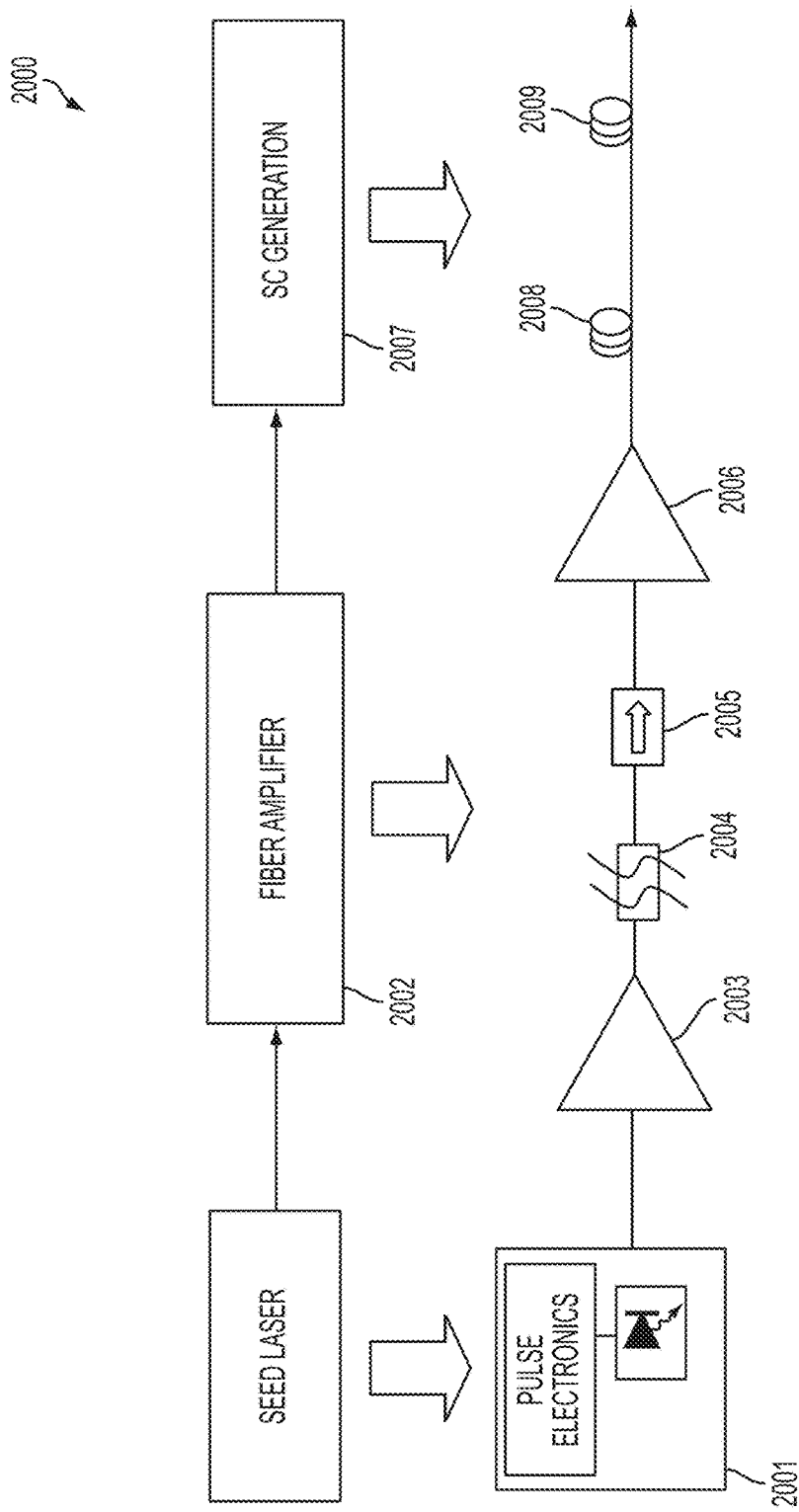
FIG. 20 shows a platform architecture for different wavelength ranges for an all-fiber-integrated, high powered, super-continuum light source.

In one embodiment, an all-fiber-integrated, high-powered SC light source 2000 may be elegant for its simplicity (FIG. 20). The light may be first generated from a seed laser diode 2001. For example, the seed LD 2001 may be a distributed feedback laser diode with a wavelength near 1542 or 1550 nm, with approximately 0.5-2.0 ns pulsed output, and with a pulse repetition rate between a kilohertz to about 100 MHz or more. The output from the seed laser diode may then be amplified in a multiple-stage fiber amplifier 2002 comprising one or more gain fiber segments. In one embodiment, the first stage pre-amplifier 2003 may be designed for optimal noise performance. For example, the pre-amplifier 2003 may be a standard erbium-doped fiber amplifier or an erbium/ytterbium doped cladding pumped fiber amplifier. Between amplifier stages 2003 and 2006, it may be advantageous to use band-pass filters 2004 to block amplified spontaneous emission and isolators 2005 to prevent spurious reflections. Then, the power amplifier stage 2006 may use a cladding-pumped fiber amplifier that may be optimized to minimize nonlinear distortion. The power amplifier fiber 2006 may also be an erbium-doped fiber amplifier, if only low or moderate power levels are to be generated.

The SC generation 2007 may occur in the relatively short lengths of fiber that follow the pump laser. In one exemplary embodiment, the SC fiber length may range from a few millimeters to 100 m or more. In one embodiment, the SC generation may occur in a first fiber 2008 where the modulational-instability initiated pulse break-up primarily occurs, followed by a second fiber 2009 where the SC generation and spectral broadening primarily occurs.

In one embodiment, one or two meters of standard single-mode fiber (SMF) after the power amplifier stage may be followed by several meters of SC generation fiber. For this example, in the SMF the peak power may be several kilowatts and the pump light may fall in the anomalous group-velocity dispersion regime—often called the soliton regime. For high peak powers in the dispersion regime, the nanosecond pulses may be unstable due to a phenomenon known as modulational instability, which is basically parametric amplification in which the fiber nonlinearity helps to phase match the pulses. As a consequence, the nanosecond pump pulses may be broken into many shorter pulses as the modulational instability tries to form soliton pulses from the quasi-continuous-wave background. Although the laser diode and amplification process starts with approximately nanosecond-long pulses, modulational instability in the short length of SMF fiber may form approximately 0.5 ps to several-picosecond-long pulses with high intensity. Thus, the few meters of SMF fiber may result in an output similar to that produced by mode-locked lasers, except in a much simpler and cost-effective manner.

The short pulses created through modulational instability may then be coupled into a nonlinear fiber for SC generation. The nonlinear mechanisms leading to broadband SC may include four-wave mixing or self-phase modulation along with the optical Raman effect. Since the Raman effect is self-phase-matched and shifts light to longer wavelengths by emission of optical photons, the SC may spread to longer wavelengths very efficiently. The short-wavelength edge may arise from four-wave mixing, and often times the short wavelength edge may be limited by increasing group-velocity dispersion in the fiber. In many instances, if the particular fiber used has sufficient peak power and SC fiber length, the SC generation process may fill the long-wavelength edge up to the transmission window.

Mature fiber amplifiers for the power amplifier stage 2006 include ytterbium-doped fibers (near 1060 nm), erbium-doped fibers (near 1550 nm), erbium/ytterbium-doped fibers (near 1550 nm), or thulium-doped fibers (near 2000 nm). In various embodiments, candidates for SC fiber 2009 include fused silica fibers (for generating SC between 0.8-2.7 μm), mid-IR fibers such as fluorides, chalcogenides, or tellurites (for generating SC out to 4.5 μm or longer), photonic crystal fibers (for generating SC between 0.4 and 1.7 μm), or combinations of these fibers. Therefore, by selecting the appropriate fiber-amplifier doping for 2006 and nonlinear fiber 2009, SC may be generated in the visible, near-IR/SWIR, or mid-IR wavelength region.

The configuration 2000 of FIG. 20 is just one particular example, and other configurations can be used and are intended to be covered by this disclosure. For example, further gain stages may be used, and different types of lossy elements or fiber taps may be used between the amplifier stages. In another embodiment, the SC generation may occur partially in the amplifier fiber and in the pig-tails from the pump combiner or other elements. In yet another embodiment, polarization maintaining fibers may be used, and a polarizer may also be used to enhance the polarization contrast between amplifier stages. Also, not discussed in detail are many accessories that may accompany this set-up, such as driver electronics, pump laser diodes, safety shut-offs, and thermal management and packaging.

Figure 21:
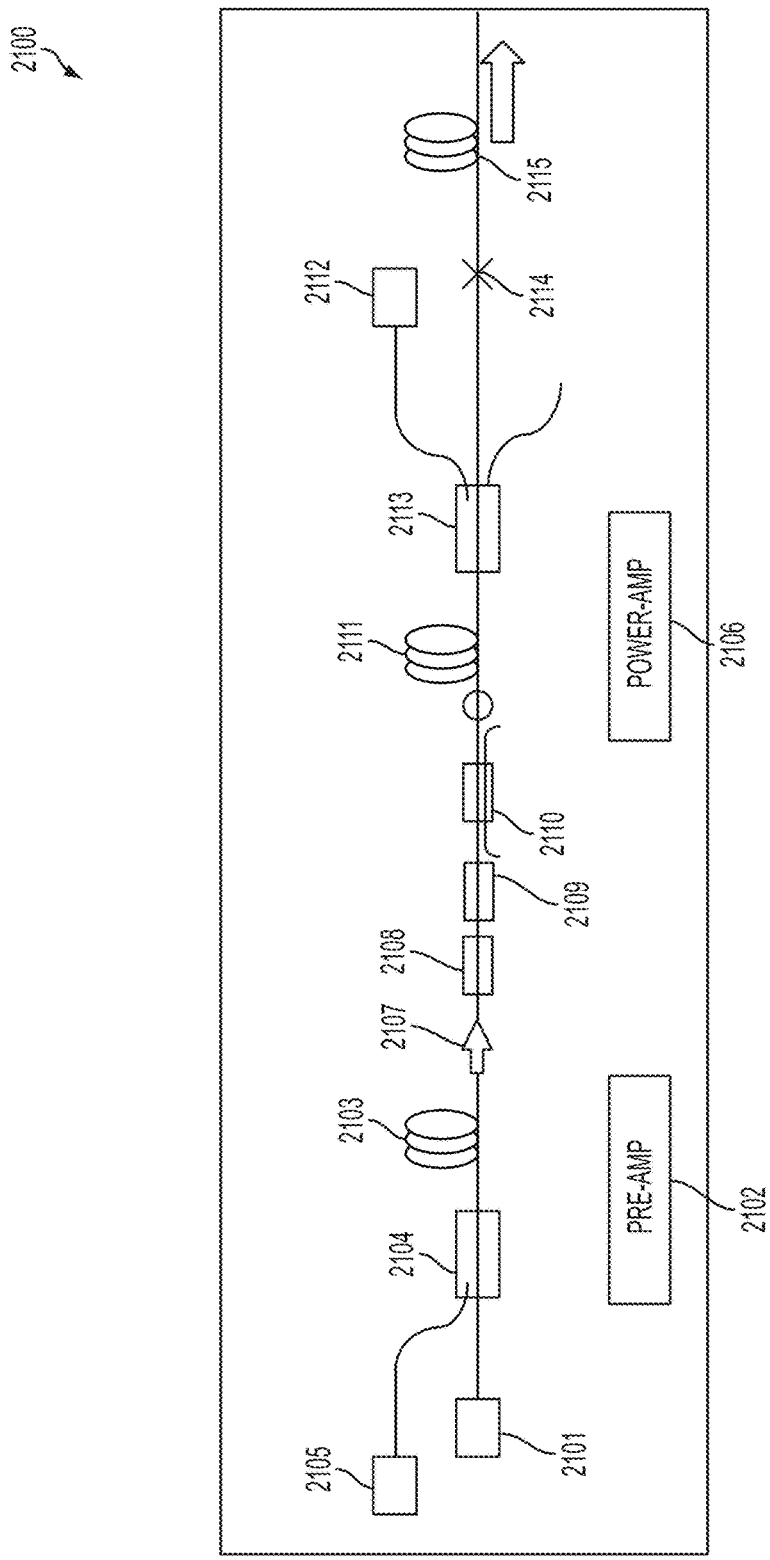
FIG. 21 illustrates one embodiment of a short-wave infrared (SWIR) super-continuum (SC) light source.

One example of an SC laser that operates in the SWIR used in one embodiment is illustrated in FIG. 21. This SWIR SC source 2100 produces an output of up to approximately 5 W over a spectral range of about 1.5 to 2.4 microns, and this particular laser is made out of polarization maintaining components. The seed laser 2101 is a distributed feedback (DFB) laser operating near 1542 nm producing approximately 0.5 nanosecond (ns) pulses at an about 8 MHz repetition rate. The pre-amplifier 2102 is forward pumped and uses about 2 m length of erbium/ytterbium cladding pumped fiber 2103 (often also called dual-core fiber) with an inner core diameter of 12 microns and outer core diameter of 130 microns. The pre-amplifier gain fiber 2103 is pumped using a 10 W 940 nm laser diode 2105 that is coupled in using a fiber combiner 2104.

In this particular 5 W unit, the mid-stage between amplifier stages 2102 and 2106 comprises an isolator 2107, a band-pass filter 2108, a polarizer 2109 and a fiber tap 2110. The power amplifier 2106 uses a 4 m length of the 12/130 micron erbium/ytterbium doped fiber 2111 that is counter-propagating pumped using one or more 30 W 940 nm laser diodes 2112 coupled in through a combiner 2113. An approximately 1-2 meter length of the combiner pig-tail helps to initiate the SC process, and then a length of PM-1550 fiber 2115 (polarization maintaining, single-mode, fused silica fiber optimized for 1550 nm) is spliced 2114 to the combiner output.

Figure 22:
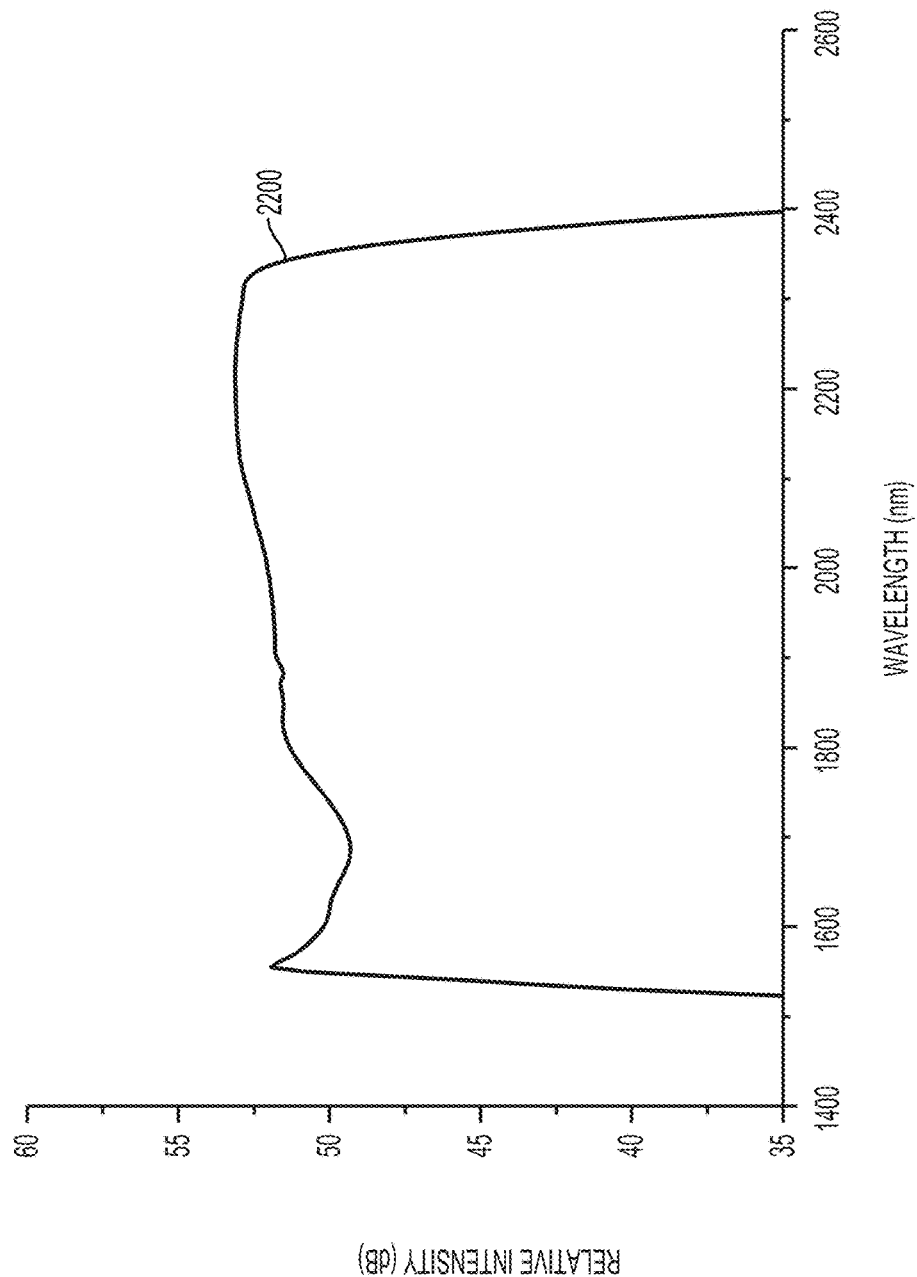
FIG. 22 shows the output spectrum from the SWIR SC laser of FIG. 21 when .about.10 m length of fiber for SC generation is used. This fiber is a single-mode, non-dispersion shifted fiber that is optimized for operation near 1550 nm.

If an output fiber of about 10 m in length is used, then the resulting output spectrum 2200 is shown in FIG. 22. The details of the output spectrum 2200 depend on the peak power into the fiber, the fiber length, and properties of the fiber such as length and core size, as well as the zero dispersion wavelength and the dispersion properties. For example, if a shorter length of fiber is used, then the spectrum actually reaches to longer wavelengths (e.g., a 2 m length of SC fiber broadens the spectrum to ~2500 nm). Also, if extra-dry fibers are used with less O—H content, then the wavelength edge may also reach to a longer wavelength. To generate more spectrum toward the shorter wavelengths, the pump wavelength (in this case .about.1542 nm) should be close to the zero dispersion wavelength in the fiber. For example, by using a dispersion shifted fiber or so-called non-zero dispersion shifted fiber, the short wavelength edge may shift to shorter wavelengths.

Although one particular example of a 5 W SWIR-SC has been described, different components, different fibers, and different configurations may also be used consistent with this disclosure. For instance, another embodiment of the similar configuration 2100 in FIG. 21 may be used to generate high powered SC between approximately 1060 and 1800 nm. For this embodiment, the seed laser 2101 may be a 1064 nm distributed feedback (DFB) laser diode, the pre-amplifier gain fiber 2103 may be a ytterbium-doped fiber amplifier with 10/125 microns dimensions, and the pump laser 2105 may be a 10 W 915 nm laser diode. In the mid-stage, a mode field adapter may be included in addition to the isolator 2107, band pass filter 2108, polarizer 2109 and tap 2110. The gain fiber 2111 in the power amplifier may be a 20 m length of ytterbium-doped fiber with 25/400 microns dimension for example. The pump 2112 for the power amplifier may be up to six pump diodes providing 30 W each near 915 nm, for example. For this much pump power, the output power in the SC may be as high as 50 W or more.

In another embodiment, it may be desirous to generate high power SWIR SC over 1.4-1.8 microns and separately 2-2.5 microns (the window between 1.8 and 2 microns may be less important due to the strong water and atmospheric absorption). For example, the top SC source of FIG. 23 can lead to bandwidths ranging from about 1400 nm to 1800 nm or broader, while the lower SC source of FIG. 23 can lead to bandwidths ranging from about 1900 nm to 2500 nm or broader. Since these wavelength ranges are shorter than about 2500 nm, the SC fiber can be based on fused silica fiber. Exemplary SC fibers include standard single-mode fiber SMF, high-nonlinearity fiber, high-NA fiber, dispersion shifted fiber, dispersion compensating fiber, and photonic crystal fibers. Non-fused-silica fibers can also be used for SC generation, including chalcogenides, fluorides, ZBLAN, tellurites, and germanium oxide fibers.

Figure 23:
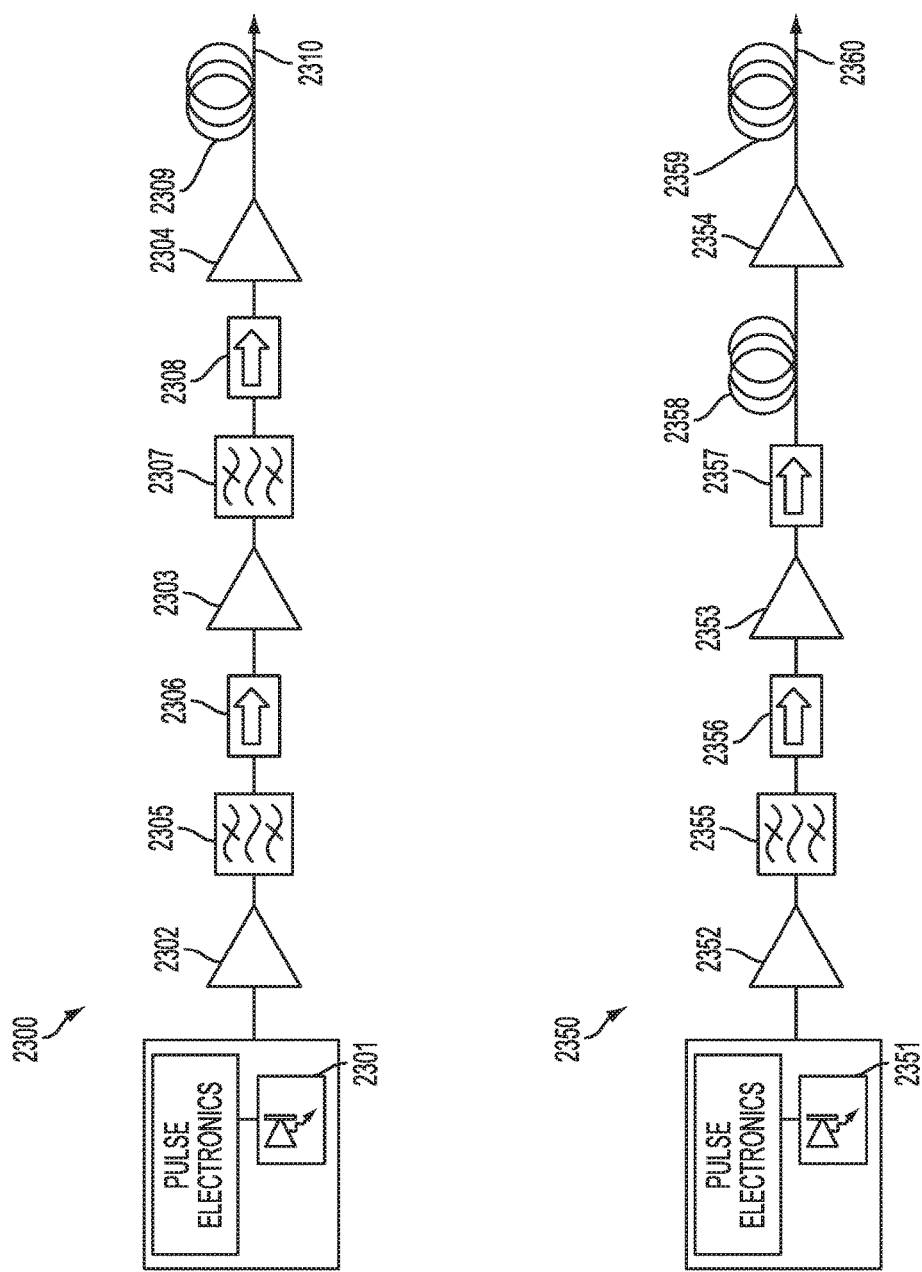
FIG. 23 illustrates high power SWIR-SC lasers that may generate light between approximately 1.4-1.8 microns (top) or approximately 2-2.5 microns (bottom).
Figure 24:
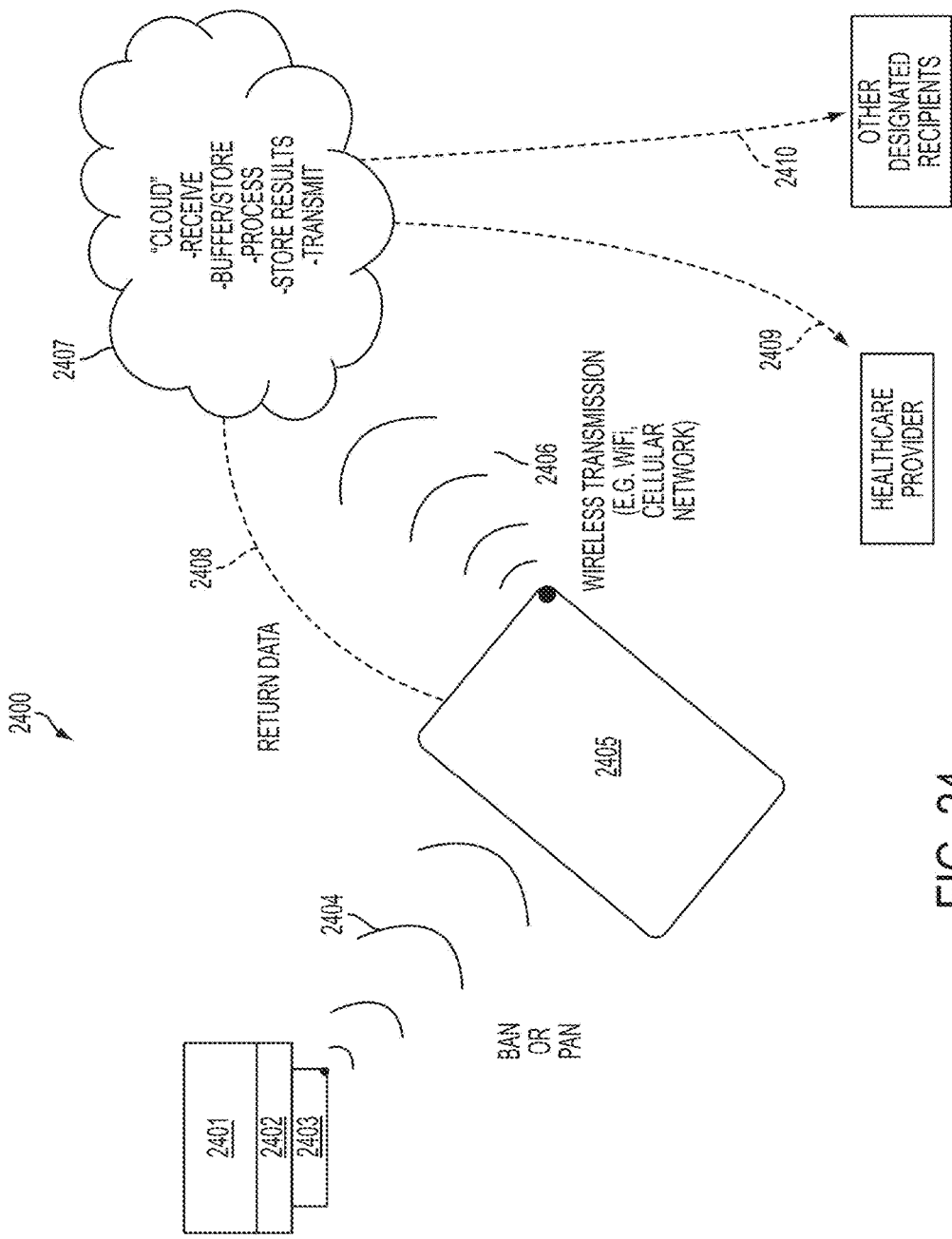
FIG. 24 schematically shows that the medical measurement device can be part of a personal or body area network that communicates with another device (e.g., smart phone or tablet) that communicates with the cloud. The cloud may in turn communicate information with the user, healthcare providers, or other designated recipients.

In one embodiment, the top of FIG. 23 illustrates a block diagram for an SC source 2300 capable of generating light between approximately 1400 and 1800 nm or broader. As an example, a pump fiber laser similar to FIG. 21 can be used as the input to a SC fiber 2309. The seed laser diode 2301 can comprise a DFB laser that generates, for example, several milliwatts of power around 1542 or 1553 nm. The fiber pre-amplifier 2302 can comprise an erbium-doped fiber amplifier or an erbium/ytterbium doped double clad fiber. In this example a mid-stage amplifier 2303 can be used, which can comprise an erbium/ytterbium doped double-clad fiber. A bandpass filter 2305 and isolator 2306 may be used between the pre-amplifier 2302 and mid-stage amplifier 2303. The power amplifier stage 2304 can comprise a larger core size erbium/ytterbium doped double-clad fiber, and another bandpass filter 2307 and isolator 2308 can be used before the power amplifier 2304. The output of the power amplifier can be coupled to the SC fiber 2309 to generate the SC output 2310. This is just one exemplary configuration for an SC source, and other configurations or elements may be used consistent with this disclosure.

In yet another embodiment, the bottom of FIG. 23 illustrates a block diagram for an SC source 2350 capable of generating light between approximately 1900 and 2500 nm or broader. As an example, the seed laser diode 2351 can comprise a DFB or DBR laser that generates, for example, several milliwatts of power around 1542 or 1553 nm. The fiber pre-amplifier 2352 can comprise an erbium-doped fiber amplifier or an erbium/ytterbium doped double clad fiber. In this example a mid-stage amplifier 2353 can be used, which can comprise an erbium/ytterbium doped double-clad fiber. A bandpass filter 2355 and isolator 2356 may be used between the pre-amplifier 2352 and mid-stage amplifier 2353. The power amplifier stage 2354 can comprise a thulium doped double-clad fiber, and another isolator 2357 can be used before the power amplifier 2354. Note that the output of the mid-stage amplifier 2353 can be approximately near 1550 nm, while the thulium-doped fiber amplifier 2354 can amplify wavelengths longer than approximately 1900 nm and out to about 2100 nm. Therefore, for this configuration wavelength shifting may be required between 2353 and 2354. In one embodiment, the wavelength shifting can be accomplished using a length of standard single-mode fiber 2358, which can have a length between approximately 5 and 50 meters, for example. The output of the power amplifier 2354 can be coupled to the SC fiber 2359 to generate the SC output 2360. This is just one exemplary configuration for an SC source, and other configurations or elements can be used consistent with this disclosure. For example, the various amplifier stages can comprise different amplifier types, such as erbium doped fibers, ytterbium doped fibers, erbium/ytterbium co-doped fibers and thulium doped fibers. One advantage of the SC lasers illustrated in FIGS. 20-23 are that they may use all-fiber components, so that the SC laser can be all-fiber, monolithically integrated with no moving parts. The all-integrated configuration can consequently be robust and reliable.

FIGS. 20-23 are examples of SC light sources that may be advantageously used for SWIR light generation in various medical diagnostic and therapeutic applications. However, many other versions of the SC light sources may also be made that are intended to also be covered by this disclosure. For example, the SC generation fiber could be pumped by a mode-locked laser, a gain-switched semiconductor laser, an optically pumped semiconductor laser, a solid state laser, other fiber lasers, or a combination of these types of lasers. Also, rather than using a fiber for SC generation, either a liquid or a gas cell might be used as the nonlinear medium in which the spectrum is to be broadened.

Even within the all-fiber versions illustrated such as in FIG. 21, different configurations could be used consistent with the disclosure. In an alternate embodiment, it may be desirous to have a lower cost version of the SWIR SC laser of FIG. 21. One way to lower the cost could be to use a single stage of optical amplification, rather than two stages, which may be feasible if lower output power is required or the gain fiber is optimized. For example, the pre-amplifier stage 2102 might be removed, along with at least some of the mid-stage elements. In yet another embodiment, the gain fiber could be double passed to emulate a two stage amplifier. In this example, the pre-amplifier stage 2102 might be removed, and perhaps also some of the mid-stage elements. A mirror or fiber grating reflector could be placed after the power amplifier stage 2106 that may preferentially reflect light near the wavelength of the seed laser 2101. If the mirror or fiber grating reflector can transmit the pump light near 940 nm, then this could also be used instead of the pump combiner 2113 to bring in the pump light 2112. The SC fiber 2115 could be placed between the seed laser 2101 and the power amplifier stage 2106 (SC is only generated after the second pass through the amplifier, since the power level may be sufficiently high at that time). In addition, an output coupler may be placed between the seed laser diode 2101 and the SC fiber, which now may be in front of the power amplifier 2106. In a particular embodiment, the output coupler could be a power coupler or divider, a dichroic coupler (e.g., passing seed laser wavelength but outputting the SC wavelengths), or a wavelength division multiplexer coupler. This is just one further example, but a myriad of other combinations of components and architectures could also be used for SC light sources to generate SWIR light that are intended to be covered by this disclosure.

Wireless Link to the Cloud

The non-invasive blood constituent or analytes measurement device may also benefit from communicating the data output to the "cloud" (e.g., data servers and processors in the web remotely connected) via wired and/or wireless communication strategies. The non-invasive devices may be part of a series of biosensors applied to the patient, and collectively these devices form what might be called a body area network or a personal area network. The biosensors and non-invasive devices may communicate to a smart phone, tablet, personal data assistant, computer, and/or other microprocessor-based device, which may in turn wirelessly or over wire and/or fiber optically transmit some or all of the signal or processed data to the internet or cloud. The cloud or internet may in turn send the data to doctors or health care providers as well as the patients themselves. Thus, it may be possible to have a panoramic, high-definition, relatively comprehensive view of a patient that doctors can use to assess and manage disease, and that patients can use to help maintain their health and direct their own care.

In a particular embodiment 2400, the physiological measurement device or non-invasive blood constituent measurement device 2401 may comprise a transmitter 2403 to communicate over a first communication link 2404 in the body area network or personal area network to a receiver in a smart phone, tablet cell phone, PDA, or computer 2405. For the measurement device 2401, it may also be advantageous to have a processor 2402 to process some of the physiological data, since with processing the amount of data to transmit may be less (hence, more energy efficient). The first communication link 2404 may operate through the use of one of many wireless technologies such as Bluetooth, Zigbee, WiFi, IrDA (infrared data association), wireless USB, or Z-wave, to name a few. Alternatively, the communication link 2404 may occur in the wireless medical band between 2360 and 2390 MHz, which the FCC allocated for medical body area network devices, or in other designated medical device or WMTS bands. These are examples of devices that can be used in the body area network and surroundings, but other devices could also be used and are included in the scope of this disclosure.

The personal device 2405 may store, process, display, and transmit some of the data from the measurement device 2401. The device 2405 may comprise a receiver, transmitter, display, voice control and speakers, and one or more control buttons or knobs and a touch screen. Examples of the device 2405 include smart phones such as the Apple iPhones® or phones operating on the Android or Microsoft systems. In one embodiment, the device 2405 may have an application, software program, or firmware to receive and process the data from the measurement device 2401. The device 2405 may then transmit some or all of the data or the processed data over a second communication link 2406 to the internet or "cloud" 2407. The second communication link 2406 may advantageously comprise at least one segment of a wireless transmission link, which may operate using WiFi or the cellular network. The second communication link 2406 may additionally comprise lengths of fiber optic and/or communication over copper wires or cables.

The internet or cloud 2407 may add value to the measurement device 2401 by providing services that augment the physiological data collected. In a particular embodiment, some of the functions performed by the cloud include: (a) receive at least a fraction of the data from the device 2405; (b) buffer or store the data received; (c) process the data using software stored on the cloud; (d) store the resulting processed data; and (e) transmit some or all of the data either upon request or based on an alarm. As an example, the data or processed data may be transmitted 2408 back to the originator (e.g., patient or user), it may be transmitted 2409 to a health care provider or doctor, or it may be transmitted 2410 to other designated recipients.

The cloud 2407 may provide a number of value-add services. For example, the cloud application may store and process the physiological data for future reference or during a visit with the healthcare provider. If a patient has some sort of medical mishap or emergency, the physician can obtain the history of the physiological parameters over a specified period of time. In another embodiment, if the physiological parameters fall out of acceptable range, alarms may be delivered to the user 2408, the healthcare provider 2409, or other designated recipients 2410. These are just some of the features that may be offered, but many others may be possible and are intended to be covered by this disclosure. As an example, the device 2405 may also have a GPS sensor, so the cloud 2407 may be able to provide time, data and position along with the physiological parameters. Thus, if there is a medical emergency, the cloud 2407 could provide the location of the patient to the healthcare provider 2409 or other designated recipients 2410. Moreover, the digitized data in the cloud 2407 may help to move toward what is often called "personalized medicine." Based on the physiological parameter data history, medication or medical therapies may be prescribed that are customized to the particular patient.

Beyond the above benefits, the cloud application 2407 and application on the device 2405 may also have financial value for companies developing measurement devices 2401 such as a non-invasive blood constituent monitor. In the case of glucose monitors, the companies make the majority of their revenue on the measurement strips. However, with a non-invasive monitor, there is no need for strips, so there is less of an opportunity for recurring costs (e.g., the razor/razor blade model does not work for non-invasive devices). On the other hand, people may be willing to pay a periodic fee for the value-add services provided on the cloud 2407. Diabetic patients, for example, would probably be willing to pay a periodic fee for monitoring their glucose levels, storing the history of the glucose levels, and having alarm warnings when the glucose level falls out of range. Similarly, patients taking ketone bodies supplement for treatment of disorders characterized by impaired glucose metabolism (e.g., Alzheimer's, Parkinson's, Huntington's or ALS) may need to monitor their ketone bodies level. These patients would also probably be willing to pay a periodic fee for the value-add services provided on the cloud 2407. Thus, by leveraging the advances in wireless connectivity and the widespread use of handheld devices such as smart phones that can wirelessly connect to the cloud, businesses can build a recurring cost business model even using non-invasive measurement devices.

Described herein are just some examples of the beneficial use of near-infrared or SWIR lasers for non-invasive monitoring of glucose, ketones, HbA1c and other blood constituents. However, many other medical procedures can use the near-infrared or SWIR light consistent with this disclosure and are intended to be covered by the disclosure.

Although the present disclosure has been described in several embodiments, a myriad of changes, variations, alterations, transformations, and modifications may be suggested to one skilled in the art, and it is intended that the present disclosure encompass such changes, variations, alterations, transformations, and modifications as falling within the spirit and scope of the appended claims.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. The embodiments described herein that are described as less desirable than other embodiments or prior art implementations with respect to one or more characteristics are not outside the scope of the disclosure and may be desirable for particular applications.

What is claimed is:

1. A smart phone or tablet, comprising:
one or more laser diodes configured to be pulsed and to generate light having one or more optical wavelengths, wherein at least a portion of the one or more optical wavelengths is a near-infrared wavelength between 700 nanometers and 2500 nanometers;
a first one or more lenses configured to receive at least a portion of the light from the one or more laser diodes and to direct at least some of the received light to tissue comprising skin;
an array of laser diodes configured to be pulsed and to generate light having one or more optical wavelengths, wherein at least a portion of the one or more optical wavelengths is a near-infrared wavelength between 700 nanometers and 2500 nanometers;
a second one or more lenses configured to receive at least a portion of the light from the array of laser diodes, the array of laser diodes and the second one or more lenses configured to form a plurality of spots and to direct at least some of the plurality of spots to the tissue;
an infrared camera configured to be synchronized to the one or more laser diodes, and to receive at least a portion of light from the one or more laser diodes that is reflected from the tissue, wherein the infrared camera generates data based at least in part on the received light, and wherein
the infrared camera is further configured to be synchronized to the array of laser diodes;
the infrared camera further configured to:
generate a first signal responsive to light received while the one or more laser diodes and the array of laser diodes are off; and
generate a second signal responsive to light received while at least some of the one or more laser diodes or some of the array of laser diodes are on, the light received while at least some of the laser diodes are on including at least some light reflected from the tissue from either the one or more laser diodes, or the array of laser diodes;
wherein the smart phone or tablet is configured to generate a two-dimensional or three-dimensional image using a difference between the first signal and the second signal, and using at least part of the data from the infrared camera;
wherein the two-dimensional or three-dimensional image is used in part to identify one or more features corresponding to the skin; and
the smart phone or tablet further comprising a wireless receiver, a wireless transmitter, a display, a voice input module, and a speaker.

2. The smart phone or tablet of claim 1, further comprising an assembly in front of the array of laser diodes configured to form at least in part the plurality of spots.

3. The smart phone or tablet of claim 1, wherein the one or more features corresponding to the skin include veins, arteries, or capillaries in the tissue.

4. The smart phone or tablet of claim 1, wherein at least a portion of the one or more laser diodes or at least a portion of the array of laser diodes comprises one or more distributed Bragg reflectors.

5. The smart phone or tablet of claim 1, wherein the at least one of the one or more laser diodes or at least one portion of the array of laser diodes has a modulation frequency, and wherein the infrared camera is configured to use a lock-in technique that detects the modulation frequency.

6. The smart phone or tablet of claim 5, wherein the infrared camera is configured to perform filtering at the modulation frequency, wherein the modulation frequency has a phase, and wherein the infrared camera is configured to lock onto the phase.

7. A smart phone or tablet, comprising:
one or more laser diodes comprising at least one laser diode configured to be pulsed and to generate light having one or more optical wavelengths, wherein at least a portion of the one or more optical wavelengths is a near-infrared wavelength between 700 nanometers and 2500 nanometers;
a first one or more lenses configured to receive at least a portion of the light from the one or more laser diodes and to direct at least some portion of the received light to tissue comprising skin;
an array of laser diodes configured to be pulsed and to generate light having one or more optical wavelengths, wherein at least a portion of the one or more optical wavelengths is a near-infrared wavelength between 700 nanometers and 2500 nanometers;
a second one or more lenses configured to receive at least a portion of the light from the array of laser diodes, the array of laser diodes and the second one or more lenses configured to form the light into a plurality of spots and to direct at least some of the spots to the tissue;
an infrared camera configured to be synchronized to the at least one laser diode of the one or more laser diodes and to receive at least a portion of light reflected from the tissue from the one or more laser diodes, wherein the infrared camera generates data based at least in part on the received light, and wherein
the infrared camera is further configured to be synchronized to the array of laser diodes;
wherein the smart phone or tablet is configured to generate a two-dimensional or three-dimensional image using at least part of the data from the infrared camera; and
the smart phone or tablet further comprising a wireless receiver, a wireless transmitter, a display, a voice input module, and a speaker.

8. The smart phone or tablet of claim 7, wherein the infrared camera is further configured to:
generate a first signal while the one or more laser diodes and the array of laser diodes are off; and
generate a second signal while at least one of the one or more laser diodes or at least one of the array of laser diodes are on, in response to received light including at least some light from the at least one of the one or more laser diodes reflected from the tissue, or at least some light from the array of laser diodes reflected from the tissue;
wherein the smart phone or tablet is further configured to use a difference between the first signal and the second signal to at least in part generate the two-dimensional or three-dimensional image.

9. The smart phone or tablet of claim 7, wherein the second one or more lenses comprises a cylindrical lens in front of at least a portion of the array of laser diodes, and wherein the plurality of spots is formed at least in part by using an assembly in front of the array of laser diodes.

10. The smart phone or tablet of claim 7, wherein at least a portion of the one or more laser diodes or at least a portion of the array of laser diodes comprises one or more distributed Bragg reflectors.

11. The smart phone or tablet of claim 7, wherein the at least one of the one or more laser diodes or at least one portion of the array of laser diodes has a modulation frequency, and wherein the infrared camera is configured to use a lock-in technique that detects the modulation frequency.

12. The smart phone or tablet of claim 11, wherein the infrared camera is configured to perform filtering at the modulation frequency, and wherein the modulation frequency has a phase, and wherein the infrared camera is further configured to lock onto the phase.

13. The smart phone or tablet of claim 7, wherein the two-dimensional or three-dimensional image is used in part to identify one or more features corresponding to the skin.

14. The smart phone or tablet of claim 13 wherein the one or more features corresponding to the skin include veins, arteries, or capillaries in the tissue.

15. A smart phone or tablet, comprising:
one or more laser diodes comprising at least one laser diode configured to be pulsed and to generate light having one or more optical wavelengths, wherein at least a portion of the one or more optical wavelengths is a near-infrared wavelength between 700 nanometers and 2500 nanometers;
a first one or more lenses configured to receive at least a portion of the light from the one or more laser diodes and to direct at least some of the received light to tissue comprising skin;
an array of laser diodes configured to be pulsed and to generate light having one or more optical wavelengths, wherein at least a portion of the one or more optical wavelengths is a near-infrared wavelength between 700 nanometers and 2500 nanometers;
a second one or more lenses configured to receive at least a portion of the light from the array of laser diodes, the array of laser diodes and the second one or more lenses configured to form a plurality of spots at least in part by using an assembly in front of the array of laser diodes, and to direct at least some of the plurality of spots to the tissue;
an infrared camera configured to be synchronized to the at least one of the one or more laser diodes and to receive at least a portion of light reflected from the tissue from at least one of the one or more laser diodes, wherein the infrared camera generates data based at least in part on the received light, and wherein
the infrared camera is further configured to be synchronized to the array of laser diodes;
wherein the smart phone or tablet is configured to generate a two-dimensional or three-dimensional image using at least part of the data from the infrared camera; and
the smart phone or tablet further comprising a wireless receiver, a wireless transmitter, a display, a voice input module, and a speaker.

16. The smart phone or tablet of claim 15, wherein at least some of the one or more laser diodes or at least a portion of the array of laser diodes comprises one or more distributed Bragg reflectors.

17. The smart phone or tablet of claim 16, wherein the two-dimensional or three-dimensional image is used in part to identify one or more features corresponding to the skin.

18. The smart phone or tablet of claim 17, wherein the at least one of the one or more laser diodes, or at least a portion of the array of laser diodes, has a modulation frequency, and wherein the infrared camera is configured to use a lock-in technique that detects the modulation frequency.

19. The smart phone or tablet of claim 18 wherein the infrared camera is configured to perform filtering at the modulation frequency, wherein the modulation frequency has a phase, and wherein the infrared camera is configured to lock onto the phase.

20. The smart phone or tablet of claim 19, wherein the infrared camera is further configured to:
generate a first signal in response to light received while the one or more laser diodes and the array of laser diodes are off; and
generate a second signal in response to light received while at least one of the one of more laser diodes or at least one laser diode of the array of laser diodes are on, the received light including at least some light from the at least one of the one or more laser diodes reflected from the tissue or at least some light from the array of laser diodes reflected from the tissue;
wherein the smart phone or tablet is further configured to use a difference between the first signal and the second signal to, at least in part, generate the two-dimensional or three-dimensional image.

* * * * *